(12) United States Patent
Passanti et al.

(10) Patent No.: US 8,084,434 B2
(45) Date of Patent: Dec. 27, 2011

(54) RUNX2 ISOFORMS IN ANGIOGENESIS

(75) Inventors: Antonino Passanti, White Hall, MD (US); Lixin Sun, Frederick, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 919 days.

(21) Appl. No.: 11/587,344

(22) PCT Filed: Apr. 26, 2005

(86) PCT No.: PCT/US2005/014137
§ 371 (c)(1),
(2), (4) Date: Nov. 21, 2007

(87) PCT Pub. No.: WO2005/117971
PCT Pub. Date: Dec. 15, 2005

(65) Prior Publication Data
US 2008/0095779 A1    Apr. 24, 2008

Related U.S. Application Data

(60) Provisional application No. 60/564,979, filed on Apr. 26, 2004.

(51) Int. Cl.
*A61K 31/70*  (2006.01)
*A61K 39/395* (2006.01)
*A61K 38/00*  (2006.01)
*C12N 5/00*   (2006.01)

(52) U.S. Cl. ...... 514/44 A; 514/44 R; 514/2; 424/130.1; 530/387.1; 536/24.5

(58) Field of Classification Search ................. None
See application file for complete search history.

(56) References Cited

OTHER PUBLICATIONS

Jadwiga et al. Med Sci Monit vol. 10(4):RA89-98, 2004.*
International Search Report of Jan. 23, 2008 for International Application No. PCT/US05/14137 filed on Apr. 26, 2005.
Sun et al., "Regulation of TGFbeta1-Medicated Growth Inhibition and Apoptosis by RUNX2 Isoforms in Endothelial Cells," Oncogene, vol. 23, Apr. 26, 2004, pp. 4722-4734.

* cited by examiner

*Primary Examiner* — Sean McGarry
(74) *Attorney, Agent, or Firm* — Evans & Molinelli PLLC; Judith Evans

(57) ABSTRACT

The present invention relates to RUNX2 and RUNXdelta8, and their use in modulating conditions and diseases associated with angiogenesis and cell proliferation. For example, RUNX2delta8 can be utilized to inhibit tumor growth and to prevent or inhibit angiogenesis. The present invention also relates to antibodies which specifically recognize RUNX2delta8, and distinguish it from RUNX2.

5 Claims, 13 Drawing Sheets

A FIGURE 3 A

RUNX2Δ8 350bp PCR product
5'GCACAGACAGAAGCTTGATGACTCTAAACCTAGTTTGTTCTCTGACCGCCTCAGTGATTTAGGGCGCATTCCT
CATCCCAGTATGAGAGTAGGTGTCCCGCCTCAGAACCCACGGCCCTCCCTGAACTCTGCACCAAGTCCTTTTA
ATCCACAAGGACAGAGTCAGATTACAGACCCCAGACAGGCACAGTCTTCCCCGCCGTGGTCCTATGACCAGTC
TTACCCGTCCTACCTGAGCCAGATGACATCCCCGTCCATTCACTCCACCACCCCGCTGTCTTCCACGCGGGGC
ACGGGGCTTCCTGCCATCACCGACGTGCCCAGGCGCATTTCAGGTGCTTCAGAACTGGG-3'

H R Q K L D D S K P S L F S D R L S D L G R I P H P S Met R V G V P P Q N
P R P S L N S A P S P F N P Q G Q S Q I T D P R Q A Q S S P P W S Y D Q S
Y P S Y L S Q Met T S P S I H S T T P L S S T R G T G L P A I T D V P R R
I S G A S E L

RUNX2 416bp PCR product
5'GCACAGACAGAAGCTTGATGACTCTAAACCTAGTTTGTTCTCTGACCGCCTCAGTGATTTAGGGCGCATTCCT
CATCCCAGTATGAGAGTAGGTGTCCCGCCTCAGAACCCACGGCCCTCCCTGAACTCTGCACCAAGTCCTTTTA
ATCCACAAGGACAGAGTCAGATTACAGACCCCAGACAGGCACAGTCTTCCCCGCCGTGGTCCTATGACCAGTC
TTACCCGTCCTACCTGAGCCAGATGACATCCCCGTCCATTCACTCCACCACCCCGCTGTCTTCCACGCGGGGC
ACGGNGCTTCCTGCCATCACCGACGTGCCCAGGCGCATTTCA GATGATGACACTGCCACCTCTGACTTCTGCC
TCTGGCCTTCCACTCTCAGTAAGAAGAGCCAGGCA GGTGCTTCAGAACTGGG-3'

H R Q K L D D S K P S L F S D R L S D L G R I P H P S Met R V G V P P Q N
P R P S L N S A P S P F N P Q G Q S Q I T D P R Q A Q S S P P W S Y D Q S
Y P S Y L S Q Met T S P S I H S T T P L S S T R G T G L P A I T D V P R R
I S D D D T A T S D F C L W P S T L S K K S Q A G A S E L

FIGURE 3 B

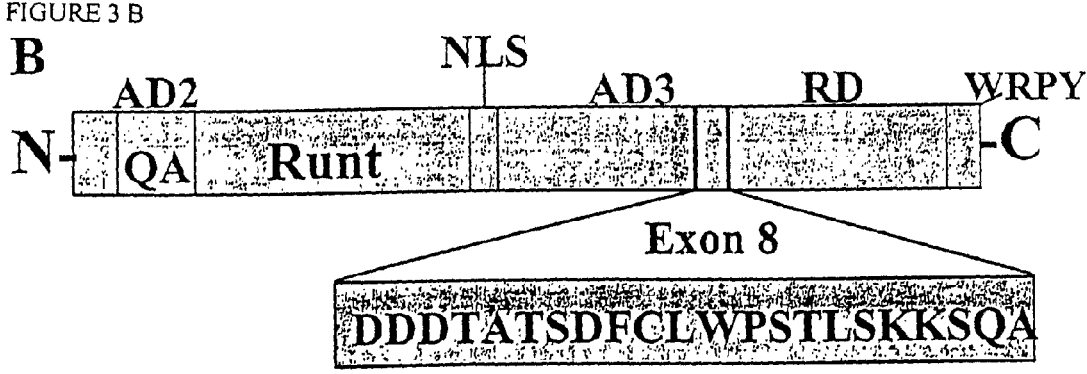

5'-CGTATTAACCACAATACTCG-3'
3'-AATTGGTGTTATGAGCATGC-5'  RUNX-binding oligo

FIG. 9

A. RUNX1
MASDSIFESFPSYPQCFMRECILGMNPSRDVHDASTSRRFTPPSTALSPGKMSEALP
LGAPDAGAALAGKLRSGDRSMVEVLADHPGELVRTDSPNFLCSVLPTHWRCNKTLPI
AFKVVALGDVPDGTLVTVMAGNDENYSAELRNATAAMKNQVARFNDLRFVGRSGRGK
SFTLTITVFTNPPQVATYHRAIKITVDGPREPRRHRQKLDDQTKPGSLSFSERLSEL
EQLRRTAMRVSPHHPAPTPNPRASLNHSTAFNPQPQSQMQDTRQIQPSPPWSYDQSY
QYLGSIASPSVHPATPISPGRASGMTTLSAELSSRLSTAPDLTAFSDPRQFPALPSI
SDPRMHYPGAFTYSPTPVTSGIGIGMSAMGSATRYHTYLPPPYPGSSQAQGGPFQAS
SPSYHLYYGASAGSYQFSMVGGERSPPRILPPCTNASTGSALLNPSLPNQSDVVEAE
GSHSNSPTNMAPSARLEEAVWRPY (SEQ ID NO:1)

B. RUNX2
MRIPVDPSTSRRFSPPSSSLQPGKMSDVSPVVAAQQQQQQQQQQQQQQQQQQQQQQ
EAAAAAAAAAAAAAAAAAVPRLRPPHDNRTMVEIIADHPAELVRTDSPNFLCSVLPS
HWRCNKTLPVAFKVVALGEVPDGTVVTVMAGNDENYSAELRNASAVMKNQVARFNDL
RFVGRSGRGKSFTLTITVFTNPPQVATYHRAIKVTVDGPREPRRHRQKLDDSKPSLF
SDRLSDLGRIPHPSMRVGVPPQNPRPSLNSAPSPFNPQGQSQITDPRQAQSSPPWSY
DQSYPSYLSQMTSPSIHSTTPLSSTRGTGLPAITDVPRRISDDDTATSDFCLWPSTL
SKKSQAGASELGPFSDPRQFPSISSLTESRFSNPRMHYPATFTYTPPVTSGMSLGMS
ATTHYHTYLPPPYPGSSQSQSGPFQTSSTPYLYYGTSSGSYQFPMVPGGDRSPSRML
PPCTTTSNGSTLLNPNLPNQNDGVDADGSHSSSPTVLNSSGRMDESVWRPY (SEQ
ID NO:35)

C. RUNX2Δ8
MRIPVDPSTSRRFSPPSSSLQPGKMSDVSPVVAAQQQQQQQQQQQQQQQQQQQQQQ
EAAAAAAAAAAAAAAAAAVPRLRPPHDNRTMVEIIADHPAELVRTDSPNFLCSVLPS
HWRCNKTLPVAFKVVALGEVPDGTVVTVMAGNDENYSAELRNASAVMKNQVARFNDL
RFVGRSGRGKSFTLTITVFTNPPQVATYHRAIKVTVDGPREPRRHRQKLDDSKPSLF
SDRLSDLGRIPHPSMRVGVPPQNPRPSLNSAPSPFNPQGQSQITDPRQAQSSPPWSY
DQSYPSYLSQMTSPSIHSTTPLSSTRGTGLPAITDVPRRISGASELGPFSDPRQFPS
ISSLTESRFSNPRMHYPATFTYTPPVTSGMSLGMSATTHYHTYLPPPYPGSSQSQSG
PFQTSSTPYLYYGTSSGSYQFPMVPGGDRSPSRMLPPCTTTSNGSTLLNPNLPNQND
GVDADGSHSSSPTVLNSSGRMDESVWRPY (SEQ ID NO:3)

D. RUNX3
MRIPVDPSTSRRFTPPSPAFPCGGGGKMGENSGALSAQAAVGPGGRARPEVRSMVD
VLADHAGELVRTDSPNFLCSVLPSHWRCNKTLPVAFKVVALGDVPDGTVVTVMAGND
ENYSAELRNASAVMKNQVARFNDLRFVGRSGRGKSFTLTITVFTNPTQVATYHRAIK
VTVDGPREPRRHRQKLEDQTKPFPDRFGDLERLRMRVTPSTPSPRGSLTTSHFSSQ
PQTPIQGTSELNPFSDPRQFDRSFPTLPTLTESRFPDPRMHYPGAMSAAFPYSATPS
GTSISSLSVAGMPATSRFHHTYLPPPYPGAPQNQSGPFQANPSPYHLYYGTSSGSYQ
FSMVAGSSSGGDRSPTRMLASCTSSAASVAAGNLMNPSLGGQSDGVEADGSHSNSPT
ALSTPGRMDEAVWRPY (SEQ ID NO: 2)

FIG 10A

```
  1 atgcgtattcctgtagatccgagcaccagccggcgcttcagcccc
    M  R  I  P  V  D  P  S  T  S  R  R  F  S  P
 46 ccctccagcagcctgcagcccggcaaaatgagcgacgtgagcccg
    P  S  S  S  L  Q  P  G  K  M  S  D  V  S  P
 91 gtggtggctgcgcaacagcagcagcaacagcagcagcagcaacag
    V  V  A  A  Q  Q  Q  Q  Q  Q  Q  Q  Q  Q
136 cagcagcagcagcagcaacagcagcagcagcagcaggaggcggcg
    Q  Q  Q  Q  Q  Q  Q  Q  Q  Q  Q  E  A  A
181 gcggcggctgcggcggcagcggcggctgcggcggcggcagctgca
    A  A  A  A  A  A  A  A  A  A  A  A  A  A
226 gtgccccggttgcggccgccccacgacaaccgcaccatggtggag
    V  P  R  L  R  P  P  H  D  N  R  T  M  V  E
271 atcatcgccgaccacccggccgaactcgtccgcaccgacagcccc
    I  I  A  D  H  P  A  E  L  V  R  T  D  S  P
316 aacttcctgtgctcggtgctgccctcgcactggcgctgcaacaag
    N  F  L  C  S  V  L  P  S  H  W  R  C  N  K
361 accctgcccgtggccttcaaggtggtagccctcggagaggtacca
    T  L  P  V  A  F  K  V  V  A  L  G  E  V  P
406 gatgggactgtggttactgtcatggcgggtaacgatgaaaattat
    D  G  T  V  V  T  V  M  A  G  N  D  E  N  Y
451 tctgctgagctccggaatgcctctgctgttatgaaaaaccaagta
    S  A  E  L  R  N  A  S  A  V  M  K  N  Q  V
496 gcaaggttcaacgatctgagatttgtgggccggagtggacgaggc
    A  R  F  N  D  L  R  F  V  G  R  S  G  R  G
541 aagagtttcaccttgaccataaccgtcttcacaaatcctccccaa
    K  S  F  T  L  T  I  T  V  F  T  N  P  P  Q
586 gtagctacctatcacagagcaattaaagttacagtagatggacct
    V  A  T  Y  H  R  A  I  K  V  T  V  D  G  P
631 cgggaacccagaaggcacagacagaagcttgatgactctaaacct
    R  E  P  R  R  H  R  Q  K  L  D  D  S  K  P
676 agtttgttctctgaccgcctcagtgatttagggcgcattcctcat
    S  L  F  S  D  R  L  S  D  L  G  R  I  P  H
721 cccagtatgagagtaggtgtcccgcctcagaacccacggccctcc
    P  S  M  R  V  G  V  P  P  Q  N  P  R  P  S
766 ctgaactctgcaccaagtcctttaatccacaaggacagagtcag
    L  N  S  A  P  S  P  F  N  P  Q  G  Q  S  Q
811 attacagaccccaggcaggcacagtcttccccgccgtggtcctat
    I  T  D  P  R  Q  A  Q  S  S  P  P  W  S  Y
856 gaccagtcttacccctcctacctgagccagatgacgtccccgtcc
    D  Q  S  Y  P  S  Y  L  S  Q  M  T  S  P  S
901 atccactctaccacccctgctgtcttccacacggggcactgggctt
    I  H  S  T  T  P  L  S  S  T  R  G  T  G  L
946 cctgccatcaccgatgtgcctaggcgcatttcagatgatgacact
    P  A  I  T  D  V  P  R  R  I  S  <u>D  D  D  T</u>
```

FIG 10B

```
 991 gccacctctgacttctgcctctggccttccactctcagtaagaag
      A  T  S  D  F  C  L  W  P  S  T  L  S  K  K
1036 agccaggcaggtgcttcagaactgggccttttcagaccccagg
      S  Q  A  G  A  S  E  L  G  P  F  S  D  P  R
1081 cagttcccaagcatttcatccctcactgagagccgcttctccaac
      Q  F  P  S  I  S  S  L  T  E  S  R  F  S  N
1126 ccacgaatgcactatccagccacctttacttacaccccgccagtc
      P  R  M  H  Y  P  A  T  F  T  Y  T  P  P  V
1171 acctcaggcatgtcctcggtatgtccgccaccactcactaccac
      T  S  G  M  S  L  G  M  S  A  T  T  H  Y  H
1216 acctacctgccaccaccctaccccggctcttcccaaagccagagt
      T  Y  L  P  P  P  Y  P  G  S  S  Q  S  Q  S
1261 ggacccttccagaccagcagcactccatatctctactatggcact
      G  P  F  Q  T  S  S  T  P  Y  L  Y  Y  G  T
1306 tcgtcaggatcctatcagtttcccatggtgccggggggagaccgg
      S  S  G  S  Y  Q  F  P  M  V  P  G  G  D  R
1351 tctccttccagaatgcttccgccatgcaccaccacctcgaatggc
      S  P  S  R  M  L  P  P  C  T  T  T  S  N  G
1396 agcacgctattaaatccaaatttgcctaaccagaatgatggtgtt
      S  T  L  L  N  P  N  L  P  N  Q  N  D  G  V
1441 gacgctgatggaagccacagcagttccccaactgttttgaattct
      D  A  D  G  S  H  S  S  S  P  T  V  L  N  S
1486 agtggcagaatggatgaatctgtttggcgaccatattga 1524
      S  G  R  M  D  E  S  V  W  R  P  Y  *
```

FIG. 11A

```
  1  atggatcccgggcagcagccgccgcctcaaccggccccccagggc
     M  D  P  G  Q  Q  P  P  P  Q  P  A  P  Q  G
 46  caagggcagccgccttcgcagccccgcaggggcagggcccgccg
     Q  G  Q  P  P  S  Q  P  P  Q  G  Q  G  P  P
 91  tccggacccgggcaaccggcacccgcggcgacccaggcggcgccg
     S  G  P  G  Q  P  A  P  A  A  T  Q  A  A  P
136  caggcacccccgccgggcatcagatcgtgcacgtccgcggggac
     Q  A  P  P  A  G  H  Q  I  V  H  V  R  G  D
181  tcggagaccgacctggaggcgctcttcaacgccgtcatgaacccc
     S  E  T  D  L  E  A  L  F  N  A  V  M  N  P
226  aagacggccaacgtgccccagaccgtgcccatgaggctccggaag
     K  T  A  N  V  P  Q  T  V  P  M  R  L  R  K
271  ctgcccgactccttcttcaagccgccggagcccaaatcccactcc
     L  P  D  S  F  F  K  P  P  E  P  K  S  H  S
316  cgacaggccagtactgatgcaggcactgcaggagccctgactcca
     R  Q  A  S  T  D  A  G  T  A  G  A  L  T  P
361  cagcatgttcgagctcattcctctccagcttctctgcagttggga
     Q  H  V  R  A  H  S  S  P  A  S  L  Q  L  G
406  gctgtttctcctgggacactgacccccactggagtagtctctggc
     A  V  S  P  G  T  L  T  P  T  G  V  V  S  G
451  ccagcagctacacccacagctcagcatcttcgacagtcttctttt
     P  A  A  T  P  T  A  Q  H  L  R  Q  S  S  F
496  gagatacctgatgatgtacctctgccagcaggttgggagatggca
     E  I  P  D  D  V  P  L  A  G  W  E  M  A
541  aagacatcttctggtcagagatacttcttaaatcacatcgatcag
     K  T  S  S  G  Q  R  Y  F  L  N  H  I  D  Q
586  acaacaacatggcaggaccccaggaaggccatgctgtcccagatg
     T  T  T  W  Q  D  P  R  K  A  M  L  S  Q  M
631  aacgtcacagcccccaccagtccaccagtgcagcagaatatgatg
     N  V  T  A  P  T  S  P  P  V  Q  Q  N  M  M
676  aactcggcttcagccatgaaccagagaatcagtcagagtgctcca
     N  S  A  S  A  M  N  Q  R  I  S  Q  S  A  P
721  gtgaaacagccaccaccctggctccccagagcccacagggaggc
     V  K  Q  P  P  P  L  A  P  Q  S  P  Q  G  G
766  gtcatgggtggcagcaactccaaccagcagcaacagatgcgactg
     V  M  G  G  S  N  S  N  Q  Q  Q  M  R  L
811  cagcaactgcagatggagaaggagaggctgcggctgaaacagcaa
     Q  Q  L  Q  M  E  K  E  R  L  R  L  K  Q  Q
856  gaactgcttcggcaggtgaggccacaggagttagccctgcgtagc
     E  L  L  R  Q  V  R  P  Q  E  L  A  L  R  S
901  cagttaccaacactggagcaggatggtgggactcaaaatccagtg
     Q  L  P  T  L  E  Q  D  G  G  T  Q  N  P  V
946  tcttctcccgggatgtctcaggaattgagaacaatgacgaccaat
     S  S  P  G  M  S  Q  E  L  R  T  M  T  T  N
```

FIG. 11B

```
 991 agctcagatcctttccttaacagtggcacctatcactctcgagat
       S  S  D  P  F  L  N  S  G  T  Y  H  S  R  D
1036 gagagtacagacagtggactaagcatgagcagctacagtgtccct
       E  S  T  D  S  G  L  S  M  S  S  Y  S  V  P
1081 cgaaccccagatgacttcctgaacagtgtggatgagatggataca
       R  T  P  D  D  F  L  N  S  V  D  E  M  D  T
1126 ggtgatactatcaaccaaagcaccctgccctcacagcagaaccgt
       G  D  T  I  N  Q  S  T  L  P  S  Q  Q  N  R
1171 ttcccagactaccttgaagccattcctgggacaaatgtggacctt
       F  P  D  Y  L  E  A  I  P  G  T  N  V  D  L
1216 ggaacactggaaggagatggaatgaacatagaaggagaggagctg
       G  T  L  E  G  D  G  M  N  I  E  G  E  E  L
1261 atgccaagtctgcaggaagctttgagttctgacatccttaatgac
       M  P  S  L  Q  E  A  L  S  S  D  I  L  N  D
1306 atggagtctgttttggctgccaccaagctagataaagaaagcttt
       M  E  S  V  L  A  A  T  K  L  D  K  E  S  F
1351 cttacatggttatag 1365
       L  T  W  L  *
```

RUNX2 ISOFORMS IN ANGIOGENESIS

This application claims the benefit of U.S. Provisional Application Ser. No. 60/564,979, filed Apr. 26, 2004, which is hereby incorporated by reference in its entirety.

STATEMENT REGARDING GOVERNMENT RIGHTS

This invention was made with government support under NIH Grant Nos. CA95350 awarded by the National Institute of Health. The government has certain rights in the invention.

BACKGROUND OF THE INVENTION

Neovascularization is an essential developmental process that is activated under pathological conditions and controlled by the expression of growth-promoting and growth-suppressing angiogenesis factors (Beck & D'Amore, 1997; Ferrara, 2000; Folkman, 1995; Kerbel, 2000; Li, 2000). During the initial activation stage, tumor or epithelial cells secrete angiogenic factors such as VEGF, FGF, and angiopoietins that alter cell cycle kinetics and stimulate EC proliferation or migration (Carmeliet & Collen, 2000; Hanahan, 1997; Maisonpierre et al., 1997). In later stages, tube formation and vessel maturation lead to vessel remodeling and apoptosis, which are regulated by TGFβ$_1$ and mesenchymal cells in the absence of EC proliferation (Beck & D'Amore, 1997; Pepper et al., 1990; Taipale & Keski-Oja, 1997). This complex process of gene expression is regulated by a variety of transcription factors whose functions in angiogenesis have been deduced from targeted gene disruption studies in vivo or in cultured cells (Sato, 2000).

The Runx genes are a conserved family of DNA binding proteins containing a unique Runt homology domain (RHD) originally described in *Drosophila* (Ito, 1999). The RUNX proteins are members of the Ig-loop DNA binding family of proteins that include Stat1, p53, and NFkB (Bravo et al., 2001). Runx proteins are phosphorylated (Selvamurugan et al., 2000; Xiao et al., 2000) and associate with the core-binding factor-β (Cbfβ) in the nucleus to bind a specific nucleotide sequence. Several key observations support a role for Runx genes in angiogenesis including the finding that mice in which either the Runx1 or Runx2 genes have been disrupted die in utero or soon after birth with vascular abnormalities (Li et al., 2002; Lund & Van Lohuizen, 2002). Runx1 negative mice fail to recruit hematopoiefic stem cells for angiogenesis and exhibit defective vessel formation in the pericardium and head (Takakura et al., 2000). In Runx2-deficient mice, there is no vascular or mesenchymal cell invasion in cartilage, no evidence of VEGF expression in hypertrophic chondrocytes, and consequently no bone formation (Komori et al., 1997; Otto et al., 1997; Zelzer et al., 2001). The absence of VEGF may be a direct consequence of reduced Runx2 binding to the VEGF promoter (Zelzer et al., 2001). Conversely, VEGF, along with several angiogenic factors including FGF-1 and IGF-1, stimulate RUNX2 expression and migration of EC in vitro and in vivo (Namba et al., 2000; Sun et al., 2001). Reports of RUNX1 expression in human vascular EC and brain tumor cells in vivo also indicate that Runx genes are upregulated in highly-vascularized malignant tumors (Perry et al., 2002).

RUNX2 contains two domains not shared by other Runx family proteins: a QA-rich domain important in regulating transcription and a domain of unknown function encoded in exon 8 (Westendorf & Hiebert, 1999). Alternatively-spliced Runx2 isoforms have been reported (Stewart et al., 1997), including alternatively spliced exon 8 (Zhang et al., 1997), which exhibited reduced transactivation relative to RUNX2 (Geoffroy a al., 1998), as well as isoforms arising from alternative transcriptional start sites (Xiao et al., 1998).

BRIEF DESCRIPTION OF THE DRAWINGS

FIG. 3 (A-B). Nucleotide sequence of a natural, alternative splice variant and RUNX2 functional domains. (A) Sequence of RUNX2 isoforms from HBME cells. Shown are the sequences for the 416 bp (RUNX2) (SEQ ID NOS 40-41, respectively, in order or appearance) and 350 by (RUNX2Δ8) (SEQ ID NOS 38-39, respectively, in order or appearance) PCR products. Sequence analysis of these PCR products showed that both were contained within human RUNX2 with the 416 bp band encompassing exons 6, 7, and 8 while the 350 bp band was the result of an exact 66 bp deletion of exon 8. The PCR primers used are shown in large type and the exon 8 nucleotides are underlined with the exon boundaries shown in vertical lines. Also shown are the amino acid sequences for RUNX2 and RUNX2Δ8 with the exon 8 peptide underlined. The N-terminal Asp residue within exon 8 is encoded by GAT while the C-terminal Ala residue is encoded by GCA. (B) Exon and functional map of RUNX2. Shown are the relative locations of the QA activation domain (AD2), the Runt DNA binding domain, the NLS nuclear localization signal, activation domain 3 (AD3) and the transcriptional repression domains RD and WRPY (SEQ ID NO: 45). The location of exon 8 within the RUNX2 functional domains and the predicted amino acid sequence (SEQ ID NO: 42) are shown.

Figure 1:
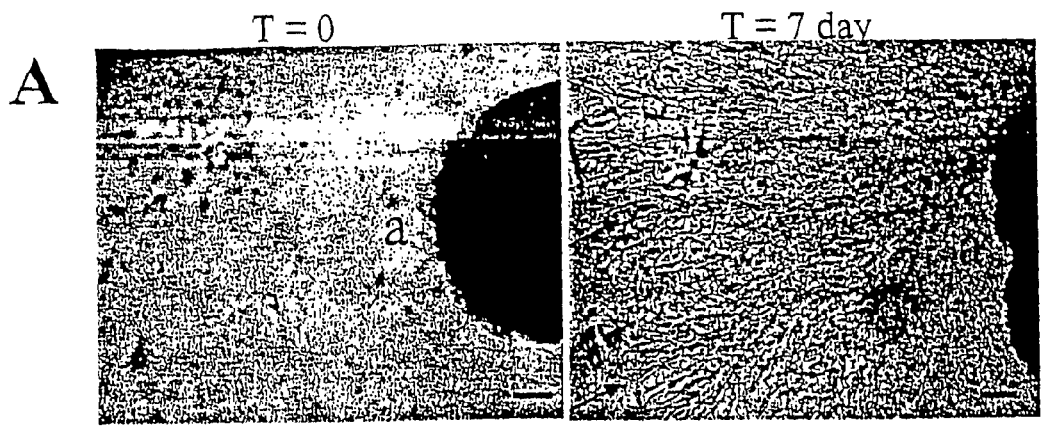
FIG. 1 (A-B). Expression of Runx2 in the rat aortic ring vascular sprouting assay. (A) Freshly dissected rat aorta were sectioned and cultured within clotted fibrin gels. Shown are aortic vessels (a) at the beginning of the incubation, time=0 and 7 days later. Arrows indicate vascular sprouts. Bar (1 cm)=200 um. (B) Runx2, urokinase (uPA), VEGF, and membrane-type metalloproteinase (MT1MMP) expression. Total RNA was extracted from fresh aortic vessels (T=0, lane 1) or vessels incubated in fibrin gel for 7 days (T=7, lane 3) and RT-PCR was performed with gene-specific primers. Cyclophilin expression was used to control for gel loading and the presence of RNA. For controls, fibrin gel (FG) adjacent to vascular sprouts was extracted under identical conditions (FG, lane 2; no cyclophilin RNA detectable). Data are representative of 3 separate experiments.
Figure 1:
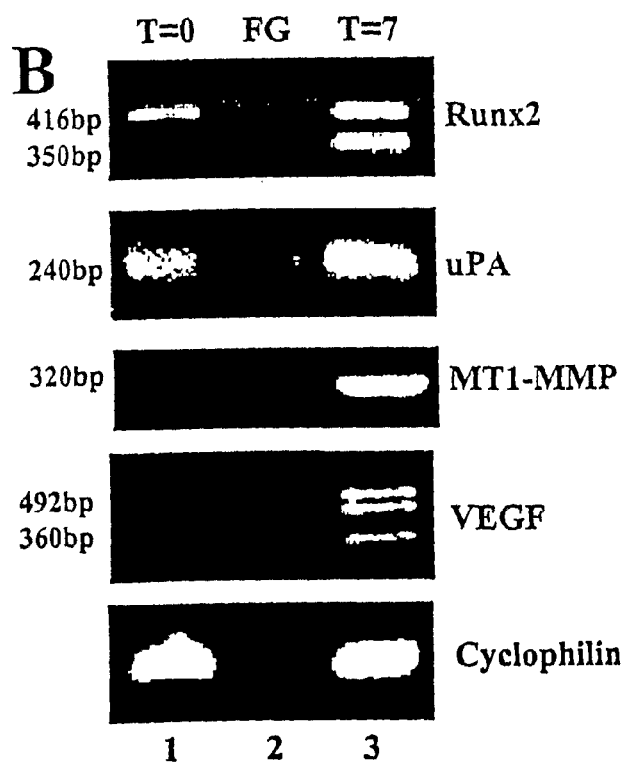

Mean and standard deviation are shown. Statistical significance between RUNX2 and NEO transfected cells (p<0.05) is indicated by the asterisk.

FIG. 9 (A-D) shows amino acid sequences of RUNX polypeptides. RUNX1 is SEQ ID NO: 1, RUNX2 is SEQ ID NO: 35; RUNX2delta8 is SEQ ID NO: 3; and RUNX3 is SEQ ID NO:2.

FIG. 10 (A and B) shows the nucleotide (SEQ ID NO: 34) and amino acid sequence (SEQ ID NO: 35) of RUNX2. The amino acid and nucleotide sequences of exon 8 are underlined. The nucleotide sequence of RUNXdelta8 contains nucleotide positions 1-979 and 1045-1486 (i.e., where the coding sequence for exon 8 are deleted). See, NCBI Accession numbers NM_004348 and NP_004339.

FIG. 11 (and B) show the nucleotide (SEQ ID NO: 36) and amino acid sequence (SEQ ID NO: 37) of YAP (yes-associated protein). NCBI Accession No. X80507.

DESCRIPTION OF THE INVENTION

The present invention relates to all facets of the RUNX, including the RUNX2delta8 isoform, polynucleotides thereof, polypeptides encoded by them, antibodies and specific binding partners thereto, and their applications to research, diagnosis, drug discovery, therapy, clinical medicine, forensic science and medicine, etc. The polynucleotides, polypeptides, and antibodies are useful in variety of ways, including, but not limited to, as molecular markers for angiogenesis, as drug targets, and for detecting, diagnosing, staging, monitoring, prognosticating, preventing or treating, determining predisposition to, etc., diseases and conditions relating to angiogenesis, cell proliferation, and cell cycle control of endothelial and tumor cells. Agents of the present invention can be used to regulate cancer, heart disease, stroke, diabetic retinopathy, and macular degeneration.

Nucleic Acids

A mammalian polynucleotide, or fragment thereof, of the present invention is a polynucleotide having a nucleotide sequence obtainable from a natural source. When the species name is used, e.g., human RUNX2deltaA8, it indicates that the polynucleotide or polypeptide is obtainable from a natural source. It therefore includes naturally-occurring normal, naturally-occurring mutant, and naturally-occurring polymorphic alleles (e.g., SNPs), differentially-spliced transcripts, splice-variants, etc. By the term "naturally-occurring," it is meant that the polynucleotide is obtainable from a natural source, e.g., animal tissue and cells, body fluids, tissue culture cells, forensic samples. Natural sources include, e.g., living cells obtained from tissues and whole organisms, tumors, cultured cell lines, including primary and immortalized cell lines.

Naturally-occurring mutations can include deletions (e.g., a truncated amino- or carboxy-terminus), substitutions, inversions, or additions of nucleotide sequence. These genes can be detected and isolated by polynucleotide hybridization according to methods which one skilled in the art would know, e.g., as discussed below.

A polynucleotide according to the present invention can be obtained from a variety of different sources. It can be obtained from DNA or RNA, such as polyadenylated mRNA or total RNA, e.g., isolated from tissues, cells, or whole organism. The polynucleotide can be obtained directly from DNA or RNA, from a cDNA library, from a genomic library, etc. The polynucleotide can be obtained from a cell or tissue (e.g., from an embryonic or adult tissues) at a particular stage of development, having a desired genotype, phenotype, disease status, etc. A polynucleotide which "codes without interruption" refers to a polynucleotide having a continuous open reading frame ("ORF") as compared to an ORF which is interrupted by introns or other noncoding sequences.

Polynucleotides and polypeptides (including any part of RUNX2 DBLTA8) can be excluded as compositions from the present invention if, e.g., listed in a publicly available databases on the day this application was filed and/or disclosed in a patent application having an earlier filing or priority date than this application and/or conceived and/or reduced to practice earlier than a polynucleotide in this application.

Specific Polynucleotide Probes

A polynucleotide of the present invention can comprise any continuous nucleotide sequence of SEQ ID NO:3, sequences which share sequence identity thereto, or complements thereof. The term "probe" refers to any substance that can be used to detect, identify, isolate, etc., another substance. A polynucleotide probe is comprised of nucleic acid can be used to detect, identify, etc., other nucleic acids, such as DNA and RNA.

These polynucleotides can be of any desired size that is effective to achieve the specificity desired. For example, a probe can be from about 7 or 8 nucleotides to several thousand nucleotides, depending upon its use and purpose. For instance, a probe used as a primer PCR can be shorter than a probe used in an ordered array of polynucleotide probes. Probe sizes vary, and the invention is not limited in any way by their size, e.g., probes can be from about 7-2000 nucleotides, 7-1000, 8-700, 8-600, 8-500, 8-400, 8-300, 8-150, 8-100, 8-75, 7-50, 10-25, 14-16, at least about 8, at least about 10, at least about 15, at least about 25, etc. The polynucleotides can have non-naturally-occurring nucleotides, e.g., inosine, AZT, 3TC, etc. The polynucleotides can have 100% sequence identity or complementarity to a sequence of SEQ ID NO:3, or it can have mismatches or nucleotide substitutions, e.g., 1, 2, 3, 4, or 5 substitutions.

In accordance with the present invention, a polynucleotide can be present in a kit, where the kit includes, e.g., one or more polynucleotides, a desired buffer (e.g., phosphate, tris, etc.), detection compositions, RNA or cDNA from different tissues to be used as controls, libraries, etc. The polynucleotide can be labeled or unlabeled, with radioactive or non-radioactive labels as known in the art. Kits can comprise one or more pairs of polynucleotides for amplifying nucleic acids specific for RUNX2DELTAA8. These include both sense and anti-sense orientations. For instance, in PCR-based methods (such as RT-PCR), a pair of primers are typically used, one having a sense sequence and the other having an antisense sequence.

Another aspect of the present invention is a nucleotide sequence that is specific to, or for, a selective polynucleotide. The phrases "specific for" or "specific to" a polynucleotide have a functional meaning that the polynucleotide can be used to identify the presence of one or more target genes in a sample and distinguish them from non-target genes. It is specific in the sense that it can be used to detect polynucleotides above background noise ("non-specific binding"). A specific sequence is a defined order of nucleotides (or amino acid sequences, if it is a polypeptide sequence) which occurs in the polynucleotide, e.g., in the nucleotide sequences of SEQ ID NO:3, and which is characteristic of that target sequence, and substantially no non-target sequences. A probe or mixture of probes can comprise a sequence or sequences that are specific to a plurality of target sequences, e.g., where the sequence is a consensus sequence, a functional domain, etc., e.g., capable of recognizing a family of related genes. Such sequences can be used as probes in any of the methods described herein or incorporated by reference. Both sense and antisense nucleotide sequences are included. A specific polynucleotide according to the present invention can be determined routinely.

A polynucleotide comprising a specific sequence can be used as a hybridization probe to identify the presence of, e.g., human polynucleotide, in a sample comprising a mixture of polynucleotides, e.g., on a Northern blot. Hybridization can be performed under high stringent conditions (see, above) to select polynucleotides (and their complements which can contain the coding sequence) having at least 90%, 95%, 99%, etc., identity (i.e., complementarity) to the probe, but less stringent conditions can also be used. A specific polynucleotide sequence can also be fused in-frame, at either its 5' or 3' end, to various nucleotide sequences as mentioned throughout the patent, including coding sequences for enzymes, detectable markers, GFP, etc, expression control sequences, etc.

A polynucleotide probe, especially one that is specific to a polynucleotide of the present invention, can be used in gene detection and hybridization methods as already described. In one embodiment, a specific polynucleotide probe can be used to detect whether a particular tissue or cell-type is present in a target sample. To carry out such a method, a selective polynucleotide can be chosen which is characteristic of the desired target tissue. Such polynucleotide is preferably chosen so that it is expressed or displayed in the target tissue, but not in other tissues which are present in the sample. For instance, if detection of endothelial cells is desired, it may not matter whether the selective polynucleotide is expressed in other tissues. Starting from the selective polynucleotide, a specific polynucleotide probe can be designed which hybridizes (if hybridization is the basis of the assay) under the hybridization conditions to the selective polynucleotide, whereby the presence of the selective polynucleotide can be determined.

Probes which are specific for polynucleotides of the present invention can also be prepared using involve transcription-based systems, e.g., incorporating an RNA polymerase promoter into a selective polynucleotide of the present invention, and then transcribing anti-sense RNA using the polynucleotide as a template. See, e.g., U.S. Pat. No. 5,545,522.

Nucleic Acid Detection Methods

Another aspect of the present invention relates to methods and processes for detecting RUNX2deltaA8. Detection methods have a variety of applications, including for diagnostic, prognostic, forensic, and research applications. To accomplish gene detection, a polynucleotide in accordance with the present invention can be used as a "probe." The term "probe" or "polynucleotide probe" has its customary meaning in the art, e.g., a polynucleotide which is effective to identify (e.g., by hybridization), when used in an appropriate process, the presence of a target polynucleotide to which it is designed. Identification can involve simply determining presence or absence, or it can be quantitative, e.g., in assessing amounts of a gene or gene transcript present in a sample. Probes can be useful in a variety of ways, such as for diagnostic purposes, to identify homologs, and to detect, quantitate, or isolate a polynucleotide of the present invention in a test sample.

Assays can be utilized which permit quantification and/or presence/absence detection of a target nucleic acid in a sample. Assays can be performed at the single-cell level, or in a sample comprising many cells, where the assay is "averaging" expression over the entire collection of cells and tissue present in the sample. Any suitable assay format can be used, including, but not limited to, e.g., Southern blot analysis, Northern blot analysis, polymerase chain reaction ("PCR") (e.g., Saiki et al., *Science,* 241:53, 1988; U.S. Pat. Nos. 4,683, 195, 4,683,202, and 6,040,166; *PCR Protocols: A Guide to Methods and Applications,* Innis et al., eds., Academic Press, New York, 1990), reverse transcriptase polymerase chain reaction ("RT-PCR"), anchored PCR, rapid amplification of cDNA ends ("RACE") (e.g., Schaefer in *Gene Cloning and Analysis: Current Innovations,* Pages 99-115, 1997), ligase chain reaction ("LCR") (EP 320 308), one-sided PCR (Ohara et al., *Proc. Natl. Acad. Sci.,* 86:5673-5677, 1989), indexing methods (e.g., U.S. Pat. No. 5,508,169), in situ hybridization, differential display (e.g., Liang et al., *Nucl. Acid. Res.,* 21:3269-3275, 1993; U.S. Pat. Nos. 5,262,311, 5,599,672 and 5,965,409; WO97/18454; Prashar and Weissman, *Proc. Natl. Acad. Sci.,* 93:659-663, and U.S. Pat. Nos. 6,010,850 and 5,712,126; Welsh et al., *Nucleic Acid Res.,* 20:4965-4970, 1992, and U.S. Pat. No. 5,487,985) and other RNA fingerprinting techniques, nucleic acid sequence based amplification ("NASBA") and other transcription based amplification systems (e.g., U.S. Pat. Nos. 5,409,818 and 5,554,527; WO 88/10315), polynucleotide arrays (e.g., U.S. Pat. Nos. 5,143, 854, 5,424,186; 5,700,637, 5,874,219, and 6,054,270; PCT WO 92/10092; PCT WO 90/15070), Qbeta Replicase (PCT/US87/00880), Strand Displacement Amplification ("SDA"), Repair Chain Reaction ("RCR"), nuclease protection assays, subtraction-based methods, Rapid-Scan™, etc. Additional useful methods include, but are not limited to, e.g., template-based amplification methods, competitive PCR (e.g., U.S. Pat. No. 5,747,251), redox-based assays (e.g., U.S. Pat. No. 5,871,918), Taqman-based assays (e.g., Holland et al., *Proc. Natl. Acad, Sci.,* 88:7276-7280, 1991; U.S. Pat. Nos. 5,210, 015 and 5,994,063), real-time fluorescence-based monitoring (e.g., U.S. Pat. No. 5,928,907), molecular energy transfer labels (e.g., U.S. Pat. Nos. 5,348,853, 5,532,129, 5,565,322, 6,030,787, and 6,117,635; Tyagi and Kramer, *Nature Biotech.,* 14:303-309, 1996). Any method suitable for single cell analysis of gene or protein expression can be used, including in situ hybridization, immunocytochemistry, MACS, FACS, flow cytometry, etc. For single cell assays, expression products can be measured using antibodies, PCR, or other types of nucleic acid amplification (e.g., Brady et al., *Methods Mol. & Cell. Biol.* 2, 17-25, 1990; Eberwine et al., 1992, *Proc. Natl. Acad. Sci.,* 89, 3010-3014, 1992; U.S. Pat. No. 5,723,290). These and other methods can be carried out conventionally, e.g., as described in the mentioned publications.

Many of such methods may require that the polynucleotide is labeled, or comprises a particular nucleotide type useful for detection. The present invention includes such modified polynucleotides that are necessary to carry out such methods. Thus, polynucleotides can be DNA, RNA, DNA:RNA hybrids, PNA, etc., and can comprise any modification or substituent which is effective to achieve detection.

Detection can be desirable for a variety of different purposes, including research, diagnostic, prognostic, and forensic. For diagnostic purposes, it may be desirable to identify the presence or quantity of a polynucleotide sequence in a sample, where the sample is obtained from tissue, cells, body fluids, etc. In a preferred method as described in more detail below, the present invention relates to a method of detecting a polynucleotide comprising, contacting a target polynucleotide in a test sample with a polynucleotide probe under conditions effective to achieve hybridization between the target and probe; and detecting hybridization.

Any test sample in which it is desired to identify a polynucleotide or polypeptide thereof can be used, including, e.g., blood, urine, saliva, stool (for extracting nucleic acid, see, e.g., U.S. Pat. No. 6,177,251), swabs comprising tissue, biopsied tissue, tissue sections, cultured cells, etc.

Detection can be accomplished in combination with polynucleotide probes for other genes, e.g., genes which are expressed in other disease states, tissues, cells, such as brain, heart, kidney, spleen, thymus, liver, stomach, small intestine, colon, muscle, lung, testis, placenta, pituitary, thyroid, skin, adrenal gland, pancreas, salivary gland, uterus, ovary, prostate gland, peripheral blood cells (T-cells, lymphocytes, etc.), embryo, normal breast fat, adult and embryonic stem cells, specific cell-types, such as endothelial, epithelial, myocytes, adipose, luminal epithelial, basoepithelial, myoepithelial, stromal cells, etc.

Polynucleotides can be used in wide range of methods and compositions, including for detecting, diagnosing, staging, grading, assessing, prognosticating, etc. diseases and disorders associated with RUNX2delta8, for monitoring or assessing therapeutic and/or preventative measures, in ordered arrays, etc. Any method of detecting genes and polynucleotides of SEQ ID NO:3 can be used; certainly, the present invention is not to be limited how such methods are implemented.

Along these lines, the present invention relates to methods of detecting RUNX2delta8 in a sample comprising nucleic acid. Such methods can comprise one or more the following steps in any effective order, e.g., contacting said sample with a polynucleotide probe under conditions effective for said probe to hybridize specifically to nucleic acid in said sample, and detecting the presence or absence of probe hybridized to nucleic acid in said sample, wherein said probe is, e.g., a polynucleotide which is SEQ ID NO:3, a polynucleotide having, e.g., about 70%, 80%, 85%, 90%, 95%, 99%, or more sequence identity thereto, effective or specific fragments thereof, or complements thereto. The detection method can be applied to any sample, e.g., cultured primary, secondary, or established cell lines, tissue biopsy, blood, urine, stool, cerebral spinal fluid, and other bodily fluids, for any purpose.

Contacting the sample with probe can be carried out by any effective means in any effective environment. It can be accomplished in a solid, liquid, frozen, gaseous, amorphous, solidified, coagulated, colloid, etc., mixtures thereof, matrix. For instance, a probe in an aqueous medium can be contacted with a sample which is also in an aqueous medium, or which is affixed to a solid matrix, or vice-versa.

Generally, as used throughout the specification, the term "effective conditions" means, e.g., the particular milieu in which the desired effect is achieved. Such a milieu, includes, e.g., appropriate buffers, oxidizing agents, reducing agents, pH, co-factors, temperature, ion concentrations, suitable age and/or stage of cell (such as, in particular part of the cell cycle, or at a particular stage where particular genes are being expressed) where cells are being used, culture conditions (including substrate, oxygen, carbon dioxide, etc.). When hybridization is the chosen means of achieving detection, the probe and sample can be combined such that the resulting conditions are functional for said probe to hybridize specifically to nucleic acid in said sample.

The phrase "hybridize specifically" indicates that the hybridization between single-stranded polynucleotides is based on nucleotide sequence complementarity. The effective conditions are selected such that the probe hybridizes to a preselected and/or definite target nucleic acid in the sample. For instance, if detection of a polynucleotide set forth in SEQ ID NO:3 is desired, a probe can be selected which can hybridize to such target gene under high stringent conditions, without significant hybridization to other genes in the sample. To detect homologs of a polynucleotide set forth in SEQ ID NO:3, the effective hybridization conditions can be less stringent, and/or the probe can comprise codon degeneracy, such that a homolog is detected in the sample.

As already mentioned, the methods can be carried out by any effective process, e.g., by Northern blot analysis, polymerase chain reaction (PCR), reverse transcriptase PCR, RACE PCR, in situ hybridization, etc., as indicated above. When PCR based techniques are used, two or more probes are generally used. One probe can be specific for a defined sequence which is characteristic of a selective polynucleotide, but the other probe can be specific for the selective polynucleotide, or specific for a more general sequence, e.g., a sequence such as polyA which is characteristic of mRNA, a sequence which is specific for a promoter, ribosome binding site, or other transcriptional features, a consensus sequence (e.g., representing a functional domain). For the former aspects, 5' and 3' probes (e.g., polyA, Kozak, etc.) are preferred which are capable of specifically hybridizing to the ends of transcripts. When PCR is utilized, the probes can also be referred to as "primers" in that they can prime a DNA polymerase reaction.

In addition to testing for the presence or absence of polynucleotides, the present invention also relates to determining the amounts at which polynucleotides of the present invention are expressed in sample and determining the differential expression of such polynucleotides in samples. Such methods can involve substantially the same steps as described above for presence/absence detection, e.g., contacting with probe, hybridizing, and detecting hybridized probe, but using more quantitative methods and/or comparisons to standards.

The amount of hybridization between the probe and target can be determined by any suitable methods, e.g., PCR, RT-PCR, RACE PCR, Northern blot, polynucleotide microarrays, Rapid-Scan, etc., and includes both quantitative and qualitative measurements. For further details, see the hybridization methods described above and below. Determining by such hybridization whether the target is differentially expressed (e.g., up-regulated or down-regulated) in the sample can also be accomplished by any effective means. For instance, the target's expression pattern in the sample can be compared to its pattern in a known standard, such as in a normal tissue, or it can be compared to another gene in the same sample. When a second sample is utilized for the comparison, it can be a sample of normal tissue that is known not to contain diseased cells. The comparison can be performed on samples which contain the same amount of RNA (such as polyadenylated RNA or total RNA), or, on RNA extracted from the same amounts of starting tissue. Such a second sample can also be referred to as a control or standard. Hybridization can also be compared to a second target in the same tissue sample. Experiments can be performed that determine a ratio between the target nucleic acid and a second nucleic acid (a standard or control), e.g., in a normal tissue. When the ratio between the target and control are substantially the same in a normal and sample, the sample is determined or diagnosed not to contain cells. However, if the ratio is different between the normal and sample tissues, the sample is determined to contain endothelial cells. The approaches can be combined, and one or more second samples, or second targets can be used. Any second target nucleic acid can be used as a comparison, including "housekeeping" genes, such as beta-actin, alcohol dehydrogenase, or any other gene whose expression does not vary depending upon the disease status of the cell.

Polynucleotide Expression and Polypeptides Produced Thereby Thereto

A polynucleotide according to the present invention can be expressed in a variety of different systems, in vitro and in vivo, according to the desired purpose. For example, a polynucleotide can be inserted into an expression vector, introduced into a desired host, and cultured under conditions effective to achieve expression of a polypeptide coded for by the polynucleotide, to search for specific binding partners. Effective conditions include any culture conditions which are suitable for achieving production of the polypeptide by the host cell, including effective temperatures, pH, medium, additives to the media in which the host cell is cultured (e.g., additives which amplify or induce expression such as butyrate, or methotrexate if the coding polynucleotide is adjacent to a dhfr gene), cycloheximide, cell densities, culture dishes, etc. A polynucleotide can be introduced into the cell by any effective method including, e.g., naked DNA, calcium phosphate precipitation, electroporation, injection, DEAE-Dextran mediated transfection, fusion with liposomes, association with agents which enhance its uptake into cells, viral transfection. A cell into which a polynucleotide of the present invention has been introduced is a transformed host cell. The polynucleotide can be extrachromosomal or integrated into a chromosome(s) of the host cell. It can be stable or transient. An expression vector is selected for its compatibility with the host cell. Host cells include, mammalian cells, e.g., COS, CV1, BHK, CHO, HeLa, LTK, NIH 3T3, 293, endothelial, epithelial, muscle, embryonic and adult stem cells, ectodermal, mesenchymal, endodermal, neoplastic, blood, bovine CPAE (CCL-209), bovine FBHE (CRL-1395), human HUV-EC-C(CRL-1730), mouse SVEC4-10EHR1 (CRL-2161), mouse MS1 (CRL-2279), mouse MS1 VEGF (CRL-2460), insect cells, such as Sf9 (*S. frugipeda*) and *Drosophila*, bacteria, such as *E. coli, Streptococcus, bacillus*, yeast, such as *Sacharomyces, S. cerevisiae*, fungal cells, plant cells, embryonic or adult stem cells (e.g., mammalian, such as mouse or human).

Expression control sequences are similarly selected for host compatibility and a desired purpose, e.g., high copy number, high amounts, induction, amplification, controlled expression. Other sequences which can be employed include enhancers such as from SV40, CMV, RSV, inducible promoters, cell-type specific elements, or sequences which allow selective or specific cell expression. Promoters that can be used to drive its expression, include, e.g., the endogenous promoter, MMTV, SV40, trp, lac, tac, or T7 promoters for bacterial hosts; or alpha factor, alcohol oxidase, or PGH promoters for yeast. RNA promoters can be used to produced RNA transcripts, such as T7 or SP6. See, e.g., Melton et al., *Polynucleotide Res.*, 12(18):7035-7056, 1984; Dunn and Studier. *J. Mol. Bio.*, 166:477-435, 1984; U.S. Pat. No. 5,891, 636; Studier et al., *Gene Expression Technology, Methods in Enzymology*, 85:60-89, 1987. In addition, as discussed above, translational signals (including in-frame insertions) can be included.

When a polynucleotide is expressed as a heterologous gene in a transfected cell line, the gene is introduced into a cell as described above, under effective conditions in which the gene is expressed. The term "heterologous" means that the gene has been introduced into the cell line by the "hand-of-man." Introduction of a gene into a cell line is discussed above. The transfected (or transformed) cell expressing the gene can be lysed or the cell line can be used intact.

For expression and other purposes, a polynucleotide can contain codons found in a naturally-occurring gene, transcript, or cDNA, for example, as set forth in SEQ ID NO:3, or it can contain degenerate codons coding for the same amino acid sequences. For instance, it may be desirable to change the codons in the sequence to optimize the sequence for expression in a desired host. See, e.g., U.S. Pat. Nos. 5,567,600 and 5,567,862.

A polypeptide according to the present invention can be recovered from natural sources, transformed host cells (culture medium or cells) according to the usual methods, including, detergent extraction (e.g., non-ionic detergent, Triton X-100, CHAPS, octylglucoside, Igepal CA-630), ammonium sulfate or ethanol precipitation, acid extraction, anion or cation exchange chromatography, phosphocellulose chromatography, hydrophobic interaction chromatography, hydroxyapatite chromatography, lectin chromatography, gel electrophoresis. Protein refolding steps can be used, as necessary, in completing the configuration of the mature protein. Finally, high performance liquid chromatography (HPLC) can be employed for purification steps. Another approach is express the polypeptide recombinantly with an affinity tag (Flag epitope, HA epitope, myc epitope, 6×His (SEQ ID NO: 46), maltose binding protein, chitinase, etc) and then purify by anti-tag antibody-conjugated affinity chromatography.

Antibodies and Specific-Binding Partners to RUNX

The present invention also relates to polypeptides of RUNX2delta8, e.g., an isolated mammalian (e.g. human) RUNX2delta8 polypeptide comprising or having the amino acid sequence set forth in FIG. 3, an isolated human RUNX2delta8 polypeptide comprising an amino acid sequence having 90%, 92%, 93%, 94%, 95%, 96%, 97%, 98%, 99% or more amino acid sequence identity to the amino acid sequence set forth in SEQ ID NO 2, and optionally having one or more of RUNX2delta8 activities. Fragments specific to RUNX2delta8 can also used, e.g., to produce antibodies or other immune responses, as competitors or agonists, etc. These fragments can be referred to as being "specific for" RUNX2delta8. The latter phrase, as already defined, indicates that the peptides are characteristic of RUNX2delta8, and that the defined sequences are substantially absent from all other protein types. Such polypeptides can be of any size which is necessary to confer specificity, e.g., 5, 8, 10, 12, 15, 20, etc.

The present invention also relates to antibodies, and other specific-binding partners, that are specific for polypeptides encoded by RUNX2delta8. Preferred antibodies span the epitope created by the deletion of exon 8, comprising at least amino acids SG or ISGA (SEQ ID NO: 4) at amino acid positions 333-336 of SEQ ID NO:3. Table I discloses examples of additional peptides that can be used to generate antibodies which are specific to RUNX2delta8. A core peptide comprising amino acids ISGA (SEQ ID NO: 4) at the 7/9 splice junction can comprise 1, 2, 3, 4, 5, 6, 7, 8, 9, 10, 11, 12, 13, 14, 15, 16, 17, 18, 19, 20, 25, 30, 35, 40, 50, etc or more amino acids at either the N- or C-terminus can be prepared to generate antibodies which specifically recognize RUNX2delta8, without recognizing the RUNX2 form.

Antibodies can also be generated against the other RUNX isoforms. Table I provides examples of peptides that be used to create isoform specific antibodies. Suitable fragments of the peptides can also be used.

Peptides that are used to generate antibodies can contain additional sequences at their N- or C-terminal ends that are unrelated to RUNX, but which are useful for coupling and to enhance immunogenicity. For example, an N-terminal cysteine can be included to facilitate the peptide's coupling to a carrier. Additional glycine residues can also be included in the linker region to provide flexibility to the peptide.

Antibodies, e.g., polyclonal, monoclonal, recombinant, chimeric, humanized, single-chain, Fab, and fragments thereof, can be prepared according to any desired method.

See, also, screening recombinant immunoglobulin libraries (e.g., Orlandi et al., *Proc. Natl. Acad. Sci.,* 86:3833-3837, 1989; Huse et al., *Science,* 256:1275-1281, 1989); in vitro stimulation of lymphocyte populations; Winter and Milstein, *Nature,* 349: 293-299, 1991. The antibodies can be IgM, IgG, subtypes, IgG2a, IgG1, etc. Antibodies, and immune responses, can also be generated by administering naked DNA See, e.g., U.S. Pat. Nos. 5,703,055; 5,589,466; 5,580, 859. Antibodies can be used from any source, including, goat, rabbit, mouse, chicken (e.g., IgY; see, Duan, W0/029444 for methods of making antibodies in avian hosts, and harvesting the antibodies from the eggs). An antibody specific for a polypeptide means that the antibody recognizes a defined sequence of amino acids within or including the polypeptide. Other specific binding partners include, e.g., aptamers and PNA.

The preparation of polyclonal antibodies is well-known to those skilled in the art. See, for example, Green et al., Production of Polyclonal Antisera, in IMMUNOCHEMICAL PROTOCOLS (Manson, ed.), pages 1-5 (Humana Press 1992); Coligan et al., Production of Polyclonal Antisera in Rabbits, Rats, Mice and Hamsters, in CURRENT PROTOCOLS IN IMMUNOLOGY, section 2.4.1 (1992). The preparation of monoclonal antibodies likewise is conventional. See, for example, Kohler & Milstein, Nature 256:495 (1975); Coligan et al., sections 2.5.1-2.6.7; and Harlow et al., ANTIBODIES: A LABORATORY MANUAL, page 726 (Cold Spring Harbor Pub. 1988).

Antibodies can also be humanized, e.g., where they are to be used therapeutically. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat. Acad. Sci.,* 86:3833 (1989), which is hereby incorporated in its entirety by reference. Techniques for producing humanized monoclonal antibodies are described, for example, in U.S. Pat. No. 6,054,297, Jones et al., Nature 321: 522 (1986); Riechmann et al., Nature 332: 323 (1988); Verhoeyen et al., Science 239: 1534 (1988); Carter et al., Proc. Nat'l Acad. Sci. USA 89: 4285 (1992); Sandhu, Crit. Rev. Biotech. 12: 437 (1992); and Singer et al., J. Immunol. 150: 2844 (1993).

Antibodies of the invention also may be derived from human antibody fragments isolated from a combinatorial immunoglobulin library. See, for example, Barbas et al., METHODS: A COMPANION TO METHODS IN ENZYMOLOGY, VOL. 2, page 119 (1991); Winter et al., Ann. Rev. Immunol. 12: 433 (1994). Cloning and expression vectors that are useful for producing a human immunoglobulin phage library can be obtained commercially, for example, from STRATAGENE Cloning Systems (La Jolla, Calif.).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens and can be used to produce human antibody-secreting hybridomas. Methods for obtaining human antibodies from transgenic mice are described, e.g., in Green et al., Nature Genet. 7:13 (1994); Lonberg et al., Nature 368:856 (1994); and Taylor et al., Int. Immunol. 6:579 (1994).

Antibody fragments of the present invention can be prepared by proteolytic hydrolysis of the antibody or by expression in *E. coli* of nucleic acid encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab').sub.2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. No. 4,036,945 and No. 4,331,647, and references contained therein. These patents are hereby incorporated in their entireties by reference. See also Nisoiihoff et al., Arch. Biochem. Biophys. 89:230 (1960); Porter, Biochem. J. 73:119 (1959); Edelman et al, METHODS IN ENZYMOLOGY, VOL. 1, page 422 (Academic Press 1967); and Coligan et al. at sections 2.8.1-2.8.10 and 2.10.1-2.10.4.

Other methods of cleaving antibodies, such as separation of heavy chains to form monovalent light-heavy chain fragments, further cleavage of fragments, or other enzymatic, chemical, or genetic techniques can also be used. For example, Fv fragments comprise an association of V.sub.H and V.sub.L chains. This association may be noncovalent, as described in Inbar et al., Proc. Nat'l Acad. Sci. USA 69:2659 (1972). Alternatively, the variable chains can be linked by an intermolecular disulfide bond or cross-linked by chemicals such as glutaraldehyde. See, e.g., Sandhu, supra. Preferably, the Fv fragments comprise V.sub.H and V.sub.L chains connected by a peptide linker. These single-chain antigen binding proteins (sFv) are prepared by constructing a structural gene comprising nucleic acid sequences encoding the V.sub.H and V.sub.L domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al., METHODS: A COMPANION TO METHODS IN ENZYMOLOGY, VOL. 2, page 97 (1991); Bird et al., Science 242:423-426 (1988); Ladner et al., U.S. Pat. No. 4,946, 778; Pack et al., Bio/Technology 11: 1271-77 (1993); and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., METHODS: A COMPANION TO METHODS IN ENZYMOLOGY, VOL. 2, page 106 (1991).

The term "antibody" as used herein includes intact molecules as well as fragments thereof, such as Fab, F(ab')2, and Fv which are capable of binding to an epitopic determinant present in Bin1 polypeptide. Such antibody fragments retain some ability to selectively bind with its antigen or receptor. The term "epitope" refers to an antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics. Antibodies can be prepared against specific epitopes or polypeptide domains, such as, for example, the SG or the ISGA (SEQ ID NO:4) epitope domains of RUNX2delta8.

Antibodies which bind to RUNX2 polypeptides of the present invention can be prepared using an intact polypeptide or fragments containing small peptides of interest as the immunizing antigen. See, Table 1 for examples of peptide fragments. The polypeptide used to immunize an animal can obtained through chemical synthesis or through recombinant methods. The peptides can be conjugated to carriers, such as proteins. Commonly used carriers which are chemically coupled to the immunizing peptide include keyhole limpet hemocyanin (KLH), thyroglobulin, bovine serum albumin (BSA), and tetanus toxoid.

Polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, *Current Protocols in Immunology*, Wiley Interscience, 1994, incorporated by reference).

Methods of Detecting Polypeptides

RUNX2 polypeptides of the present invention can be detected, visualized, determined, quantitated, etc. according to any effective method. useful methods include, e.g., but are not limited to, immunoassays, RIA (radioimmunassay), ELISA, (enzyme-linked-immunosorbent assay), immunoflourescence, flow cytometry, histology, electron microscopy, light microscopy, in situ assays, immunoprecipitation, Western blot, etc.

Immunoassays may be carried in liquid or on biological support. For instance, a sample (e.g., blood, stool, urine, cells, tissue, cerebral spinal fluid, body fluids, etc.) can be brought in contact with and immobilized onto a solid phase support or carrier such as nitrocellulose, or other solid support that is capable of immobilizing cells, cell particles or soluble proteins. The support may then be washed with suitable buffers followed by treatment with the detectably labeled RUNX2delta8 specific antibody. The solid phase support can then be washed with a buffer a second time to remove unbound antibody. The amount of bound label on solid support may then be detected by conventional means.

A "solid phase support or carrier" includes any support capable of binding an antigen, antibody, or other specific binding partner. Supports or carriers include glass, polystyrene, polypropylene, polyethylene, dextran, nylon, amylases, natural and modified celluloses, polyacrylamides, and magnetite. A support material can have any structural or physical configuration. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads One of the many ways in which gene peptide-specific antibody can be detectably labeled is by linking it to an enzyme and using it in an enzyme immunoassay (EIA). See, e.g., Voller, A., "The Enzyme Linked Immunosorbent Assay (ELISA)," 1978, Diagnostic Horizons 2, 1-7, Microbiological Associates Quarterly Publication, Walkersville, Md.); Voller, A. et al., 1978, J. Clin. Pathol. 31, 507-520; Butler, J. E., 1981, Meth. Enzymol. 73, 482-523; Maggio, E. (ed.), 1980, Enzyme Immunoassay, CRC Press, Boca Raton, Fla.

The enzyme which is bound to the antibody will react with an appropriate substrate, preferably a chromogenic substrate, in such a manner as to produce a chemical moiety that can be detected, for example, by spectrophotometric, fluorimetric or by visual means. Enzymes that can be used to detectably label the antibody include, but are not limited to, malate dehydrogenase, staphylococcal nuclease, delta-5-steroid isomerase, yeast alcohol dehydrogenase, .alpha.-glycerophosphate, dehydrogenase, triose phosphate isomerase, horseradish peroxidase, alkaline phosphatase, asparaginase, glucose oxidase, .beta.-galactosidase, ribonuclease, urease, catalase, glucose-6-phosphate dehydrogenase, glucoamylase and acetylcholinesterase. The detection can be accomplished by colorimetric methods that employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect RUNX2delta8 peptides through the use of a radioimmunoassay (RIA). See, e.g., Weintraub, B., Principles of Radioimmunoassays, Seventh Training Course on Radioligand Assay Techniques, The Endocrine Society, March, 1986. The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine. The antibody can also be detectably labeled using fluorescence emitting metals such as those in the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Identifying Agents which Modulate RUNX2delta8 Activity and Expression

The present invention also relates to methods of identifying agents, and the agents themselves, which modulate RUNX2delta8. These agents can be used to modulate the biological activity of the polypeptide encoded for the gene, or the gene, itself. Agents which regulate the gene or its product are useful in variety of different environments, including as medicinal agents to treat or prevent disorders associated with RUNX2delta8 and as research reagents to modify the function of tissues and cell.

Methods of identifying agents generally comprise steps in which an agent is placed in contact with the gene, transcription product, translation product, or other target, and then a determination is performed to assess whether the agent "modulates" the target. The specific method utilized will depend upon a number of factors, including, e.g., the target (i.e., is it the gene or polypeptide encoded by it), the environment (e.g., in vitro or in vivo), the composition of the agent, etc.

For modulating the expression of RUNX2delta8 gene, a method can comprise, in any effective order, one or more of the following steps, e.g., contacting a RUNX2delta88 gene (e.g., in a cell population) with a test agent under conditions effective for said test agent to modulate the expression of RUNX2delta8, and determining whether said test agent modulates said RUNX2 RUNX2delta8. An agent can modulate expression of RUNX2delta8 at any level, including transcription, translation, and/or perdurance of the nucleic acid (e.g., degradation, stability, etc.) in the cell.

For modulating the biological activity of RUNX2delta8 polypeptides, a method can comprise, in any effective order, one or more of the following steps, e.g., contacting a RUNX2delta8 polypeptide (e.g., in a cell, lysate, or isolated) with a test agent under conditions effective for said test agent to modulate the biological activity of said polypeptide, and determining whether said test agent modulates said biological activity.

Contacting RUNX2delta8 with the test agent can be accomplished by any suitable method and/or means that places the agent in a position to functionally control expression or biological activity of RUNX2delta8 present in the sample. Functional control indicates that the agent can exert its physiological effect on RUNX2DELTA8 through whatever mechanism it works. The choice of the method and/or means can depend upon the nature of the agent and the condition and type of environment in which the RUNX2DELTA8 is presented, e.g., lysate, isolated, or in a cell population (such as, in vivo, in vitro, organ explants, etc.). For instance, if the cell population is an in vitro cell culture, the agent can be contacted with the cells by adding it directly into the culture medium. If the agent cannot dissolve readily in an aqueous medium, it can be incorporated into liposomes, or another lipophilic carrier, and then administered to the cell culture. Contact can also be facilitated by incorporation of agent with carriers and delivery molecules and complexes, by injection, by infusion, etc.

After the agent has been administered in such a way that it can gain access to RUNX2delta8, it can be determined whether the test agent modulates RUNX2delta8 expression or biological activity. Modulation can be of any type, quality, or quantity, e.g., increase, facilitate, enhance, up-regulate, stimulate, activate, amplify, augment, induce, decrease, down-regulate, diminish, lessen, reduce, etc. The modulatory quantity can also encompass any value, e.g., 1%, 5%, 10%, 50%, 75%, 1-fold, 2-fold, 5-fold, 10-fold, 100-fold, etc. To modulate RUNX2delta8 expression means, e.g., that the test agent has an effect on its expression, e.g., to effect the amount of transcription, to effect RNA splicing, to effect translation of the RNA into polypeptide, to effect RNA or polypeptide stability, to effect polyadenylation or other processing of the RNA, to effect post-transcriptional or post-translational processing, etc. To modulate biological activity means, e.g., that a functional activity of the polypeptide is changed in comparison to its normal activity in the absence of the agent. This effect includes, increase, decrease, block, inhibit, enhance, etc. Biological activities of RUNX2delta8 include, e.g., ability to compete with RUNX2, ability to inhibit angiogenesis, ability to produce apoptosis of endothelial cells, and/or ability to produce apoptosis of tumor cells.

A test agent can be of any molecular composition, e.g., chemical compounds, biomolecules, such as polypeptides, lipids, nucleic acids (e.g., antisense to a polynucleotide sequence selected from SEQ ID NO:3), carbohydrates, antibodies, ribozymes, double-stranded RNA, aptamers, etc. For example, if a polypeptide to be modulated is a cell-surface molecule, a test agent can be an antibody that specifically recognizes it and, e.g., causes the polypeptide to be internalized, leading to its down regulation on the surface of the cell. Such an effect does not have to be permanent, but can require the presence of the antibody to continue the down-regulatory effect. Antibodies can also be used to modulate the biological activity a polypeptide in a lysate or other cell-free form.

Antisense RUNX2delta8 can also be used as test agents to modulate gene expression. Antisense polynucleotide (e.g., RNA) can also be prepared from a polynucleotide according to the present invention, preferably an anti-sense to a sequence of SEQ ID NO:3. Antisense polynucleotide can be used in various ways, such as to regulate or modulate expression of the polypeptides they encode, e.g., inhibit their expression, for in situ hybridization, for therapeutic purposes, for making targeted mutations (in vivo, triplex, etc.) etc. For guidance on administering and designing anti-sense, see, e.g., U.S. Pat. Nos. 6,200,960, 6,200,807, 6,197,584, 6,190,869, 6,190,661, 6,187,587, 6,168,950, 6,153,595, 6,150,162, 6,133,246, 6,117,847, 6,096,722, 6,087,343, 6,040,296, 6,005,095, 5,998,383, 5,994,230, 5,891,725, 5,885,970, and 5,840,708. An antisense polynucleotides can be operably linked to an expression control sequence. A total length of about 35 by can be used in cell culture with cationic liposomes to facilitate cellular uptake, but for in vivo use, preferably shorter oligonucleotides are administered, e.g. 25 nucleotides.

Antisense polynucleotides can comprise modified, nor-maturally-occurring nucleotides and linkages between the nucleotides (e.g., modification of the phosphate-sugar backbone; methyl phosphonate, phosphorothioate, or phosphorodithioate linkages; and 2'-O-methyl ribose sugar units), e.g., to enhance in vivo or in vitro stability, to confer nuclease resistance, to modulate uptake, to modulate cellular distribution and compartmentalization, etc. Any effective nucleotide or modification can be used, including those already mentioned, as known in the art, etc., e.g., disclosed in U.S. Pat. Nos. 6,133,438; 6,127,533; 6,124,445; 6,121,437; 5,218,103 (e.g., nucleoside thiophosphoramidites); 4,973,679; Sproat et al., "2'-O-Methyloligoribonucleotides: synthesis and applications," Oligonucleotides and Analogs A Practical Approach, Eckstein (ed.), IRL Press, Oxford, 1991, 49-86; Iribarren et al., "2'O-Alkyl Oligoribonucleotides as Antisense Probes," Proc. Natl. Acad. Sci. USA, 1990, 87, 7747-7751; Cotton et al., "2'-O-methyl, 2'-O-ethyl oligoribonucleotides and phosphorothioate oligodeoxyribonucleotides as inhibitors of the in vitro U7 snRNP-dependent mRNA processing event," Nucl. Acids Res., 1991, 19, 2629-2635.

Methods and Agents for Modulating Endothelial Cell Proliferation and Angiogenesis The present invention relates to methods for identifying agents which modulate endothelial cell proliferation and angiogenesis, methods for modulating endothelial cell proliferation and angiogenesis, and the agents themselves.

For example, the present invention relates to methods for screening agents that modulate an endothelial cell's responsiveness to TGF-beta1, comprising one or more of the following steps, in any effective disorder:

a) contacting a transfected host cell with effective amounts of an agent, and optionally TGF-beta1, wherein said transfected cell comprises: a polynucleotide comprising an expressible RUNX2delta8 polynucleotide and a p21CIP1 promoter operably linked to a polynucleotide sequence coding for a detectable product; and b) identifying whether the agent represses promoter activity as measured by the amount measured of said detectable product.

A transfected cell is a host cell which has been engineered to express the RUNX2 isoform and the reporter gene. Transfection can be accomplished routinely. An "expressible" RUNX2delta8 polynucleotide comprises the polynucleotide sequences which enable the RUNX2delta8 isoform to be transcribed into RNA and translated into polypeptide. These sequences include, e.g., promoter, enhancer, transcription terminator sites, etc. In addition to the RUNX2 isoform, the cell can also be engineered to contain a p21 promoter operably linked to a polynucleotide sequence coding for a detectable product. As explained in the examples, the p21 promoter is regulated by RUNX2. In its presence, the p21 promoter is repressed. The RUNX2delta8 isoform is able to bind to the promoter, and compete with RUNX2, but it does not substantially repress it.

Methods of the present invention can be used to identify agents which restore the ability of the RUNX2delta8 isoform to repress p21. This effect can be monitored by assaying for the appearance of the detectable product. The p21-detectable product construct can also be referred to as a reporter gene. In the examples, luciferase is used as the detectable product, but others can be used as well, e.g., beta-galactosidase, etc. Agents identified in this method can be used, e.g., to restore a cell's ability to respond to inhibition of endothelial cell proliferation by TGFbeta1. This can be used to treat diseases associated with aberrant revascularization, such as cancer.

The present invention also relates to methods of identifying modulators of RUNX2delta8 in a cell population capable of forming blood vessels, comprising, one or more of the following steps in any effective order, e.g., contacting the cell population with a test agent under conditions effective for said test agent to modulate its expression or biological activity. These methods are useful, e.g., for drug discovery in identifying and confirming the angiogenic activity of agents, for identifying molecules in the normal pathway of angiogenesis, etc.

Any cell population capable of forming blood vessels can be utilized. Useful models, included those mentioned above, e.g., in vivo Matrigel-type assays, tumor neovascularization assays, CAM assays, BCE assays, migration assays, HUVEC growth inhibition assays, animal models (e.g., tumor growth in athymic mice), models involving hybrid cell and electronic-based components, etc. Cells can include, e.g., endothelial, epithelial, muscle, embryonic and adult stem cells, ectodermal, mesenchymal, endodermal, neoplastic, blood, bovine CPAE (CCL-209), bovine FBHE (CRL-1395), human HUV-EC-C(CRL-1730), mouse SVEC4-10EHR1 (CRL-2161), mouse MS1 (CRL-2279), mouse MS1 VEGF (CRL-2460), stem cells, etc. The phrase "capable of forming blood vessels" does not indicate a particular cell-type, but simply that the cells in the population are able under appropriate conditions to form blood vessels. In some circumstances, the population may be heterogeneous, comprising more than one cell-type, only some which actually differentiate into blood vessels, but others which are necessary to initiate, maintain, etc., the process of vessel formation.

The cell population can be contacted with the test agent in any manner and under any conditions suitable for it to exert an effect on the cells, and to modulate the differentially-expressed gene or polypeptide. The means by which the test agent is delivered to the cells may depend upon the type of test agent, e.g., its chemical nature, and the nature of the cell population. Generally, a test agent must have access to the cell population, so it must be delivered in a form (or pro-form) that the population can experience physiologically, i.e., to put in contact with the cells. For instance, if the intent is for the agent to enter the cell, if necessary, it can be associated with any means that facilitate or enhance cell penetrance, e.g., associated with antibodies or other reagents specific for cell-surface antigens, liposomes, lipids, chelating agents, targeting moieties, etc. Cells can also be treated, manipulated, etc., to enhance delivery, e.g., by electroporation, pressure variation, etc.

A purpose of administering or delivering the test agents to cells capable of forming blood vessels is to determine whether they modulate the RUNX2delta8 expression or polypeptide. By the phrase "modulate," it is meant that the gene or polypeptide affects the polypeptide or gene in some way. Modulation includes effects on transcription, RNA splicing, RNA editing, transcript stability and turnover, translation, polypeptide activity, and, in general, any process involved in the expression and production of the gene and gene product. The modulatory activity can be in any direction, and in any amount, including, up, down, enhance, increase, stimulate, activate, induce, turn on, turn off, decrease, block, inhibit, suppress, prevent, etc.

Any type of test agent can be used, comprising any material, such as chemical compounds, biomolecules, such as polypeptides (including polypeptide fragments and mimics), lipids, nucleic acids, carbohydrates, antibodies, small molecules, fusion proteins, etc. Test agents include, e.g., protamine (Taylor et al., Nature, 297:307, 1982), heparins, steroids, such as tetrahydrocortisol, which lack gluco- and mineral-corticoid activity (e.g., Folkman et al., Science, 221: 719, 1983 and U.S. Pat. Nos. 5,001,116 and 4,994,443), angiostatins (e.g., WO 95/292420), triazines (e.g., U.S. Pat. No. 6,150,362), thrombospondins, endostatins, platelet factor 4, fumagillin-derivate AGH 1470, alpha-interferon, quinazolinones (e.g., U.S. Pat. No. 6,090,814), substituted dibenzothiophenes (e.g., U.S. Pat. No. 6,022,307), deoxytetracyclines, cytokines, chemokines, FGFs, antisense or siRNA to RUNX2delta8, antibodies specific for RUNX2delta8.

Whether the test agent modulates a gene or polypeptide can be determined by any suitable method. These methods include, detecting gene transcription, detecting mRNA, detecting polypeptide and activity thereof. The detection methods includes those mentioned herein, e.g., PCR, RT-PCR, Northern blot, ELISA, Western, RIA, yeast two-hybrid system (e.g., for identifying natural and synthetic nucleic acids and their products which regulated RUNX2). In addition, further downstream targets can be used to assess the effects of modulators, including, the presence or absence of neoangiogenesis (e.g., using any of the mentioned test systems, such as CAM, BCE, in vivo Matrigel-type assays) as modulated by a test agent.

The present invention also relates to methods of regulating angiogenesis in a system comprising cells, comprising administering to the system an effective amount of a modulator of RUNX2 or RUNX2delta8, whereby angiogenesis is regulated. A system comprising cells can be an in vivo system, such as a heart or limb present in a patient (e.g., angiogenic therapy to treat myocardial infarction), isolated organs, tissues, or cells, in vitro assays systems (CAM, BCE, etc), animal models (e.g., in vivo, subcutaneous, chronically ischemic lower limb in a rabbit model, cancer models), hosts in need of treatment (e.g., hosts suffering from angiogenesis related diseases, such as cancer, ischemic syndromes, arterial obstructive disease, to promote collateral circulation, to promote vessel growth into bioengineered tissues, etc.

A modulator useful in such method are those mentioned already, e.g., nucleic acid (such as an anti-sense to a gene to disrupt transcription or translation of the gene), antibodies (e.g., to inhibit a cell-surface protein, such as an antibody specific-for the extracellular domain). Antibodies and other agents which target a polypeptide can be conjugated to a cytotoxic or cytostatic agent, such as those mentioned already. A modulator can also be a differentially-expressed gene, itself, e.g., when it is desired to deliver the polypeptide to cells analogously to gene therapy methods. A complete gene, or a coding sequence operably linked to an expression control sequence (i.e., an expressible gene) can be used to produce polypeptide in the target cells.

By the phrase "regulating angiogenesis," it is meant that angiogenesis is effected in a desired way by the modulator. This includes, inhibiting, blocking, reducing, stimulating, inducing, etc., the formation of blood vessels. For instance, in cancer, where the growth of new blood vessels is undesirable, modulators of a differentially-expressed can be used to inhibit their formation, thereby treating the cancer. Such inhibitory modulators include, e.g., antibodies to the extracellular regions of a differentially-expressed polypeptide, and, anti-sense RNA to inhibit translation of a differentially-expressed mRNA into polypeptide (for guidance on administering and designing anti-sense, see, e.g., U.S. Pat. Nos. 6,153,595, 6,133,246, 6,117,847, 6,096,722, 6,087,343, 6,040,296, 6,005,095, 5,998,383, 5,994,230, 5,891,725, 5,885,970, and 5,840,708). On the other hand, angiogenesis can be stimulated to treat ischemic syndromes and arterial obstructive disease, to promote collateral circulation, and to promote vessel growth into bio-engineered tissues, etc., by administering the a differentially-expressed gene or polypeptide to a target cell population.

The present invention also relates to compositions comprising RUNX2delta8 polypeptide or polynucleotide for treating disorders or conditions associated with neovascularization and/or excessive vascularization. As indicated in the examples below, expression of RUNX2delta8 in endothelial cells results in apoptosis. Thus, the polypeptide, or a polynucleotide encoding it, can be introduced into endothelial cells to treat or prevent excessive vascularization, e.g., to treat cancer. The polynucleotide can be introduced routinely into cells, e.g., injected directly into the tumor using naked polynucleotide which comprises the RUNX2delta8 coding sequence. The sequence can be injected alone, or associated with expression control sequences. The polypeptide can be similarly administered by direct injection into the target, e.g., into a tumor. The composition can also further comprise effective amounts of TGFbeta1, e.g., 1 microgram, 10 micrograms, 100 micrograms, etc.

Reducing or knocking down the expression of RUNX2 can also be utilized to treat cell proliferation disorders, including cancers associated with angiogenesis. Any cancer can be treated included, breast cancer. As shown in the examples, siRNA targeting of RUNX2 can be used to treat cell proliferation disorders.

Compositions for Increasing Cell Proliferation, Survival, and Angiogenesis

The present invention also relates to compositions for increasing cell proliferation or promoting survival of stem cells, comprising: RUNX2 polypeptide or polynucleotide, and/or YAP polypeptide or polynucleotide. As shown in the examples, the combination of RUNX2 and YAP (also known as YAP65 or Yes-associated protein) can increase cell proliferation. As explained above, either the polynucleotide or polypeptide can be administered. The compositions are useful in diseases or conditions where neo-vascularization is desired, such as heart disease. For example, in diseased hearts where vascular blockage is observed, the composition can be directly injected into the heart muscle (other locations) to stimulate angiogenesis. The gene or polypeptide can also be utilized to promote the survival of stem cells and other primary cell cultures.

Similarly, RUNX2 can also be administered for the purpose of stimulating angiogenesis. It can be administered either as polynucleotide or as polypeptide. Any condition that would benefit from increase vascularization can be treated, e.g., myocardial infarction, ischemic syndromes, arterial obstructive disease, to promote collateral circulation, to promote vessel growth into bioengineered tissues, etc.

Methods of Detecting Angiogenesis Using RUNX2delta8

The present invention also relates to detecting the presence and/or extent of blood vessels in a sample. The detected blood vessels can be established or pre-existing vessels, newly formed vessels, vessels in the process of forming, or combinations thereof. A blood vessel includes any biological structure that conducts blood, including arteries, veins, capillaries, microvessels, vessel lumen, endothelial-lined sinuses, etc. These methods are useful for a variety of purposes. In cancer, for instance, the extent of vascularization can be an important factor in determining the clinical behavior of neoplastic cells. See, e.g., Weidner et al., *N. Engl. J. Med.,* 324:1-8, 1991. Thus, the presence and extent of blood vessels, including the angiogenic process itself, can be useful for the diagnosis, prognosis, treatment, etc., of cancer and other neoplasms. Detection of vessels can also be utilized for the diagnosis, prognosis, treatment, of any diseases or conditions associated with vessel growth and production, to assess agents which modulate angiogenesis, to assess angiogenic gene therapy, etc.

An example of a method of detecting the presence or extent of blood vessels in a sample is determining an angiogenic index of a tissue or cell sample comprising, e.g., assessing in a sample, the expression levels of RUNX2 or RUNX2delta8, whereby said levels are indicative of the angiogenic index. As shown in the Examples below, RUNX2delta8 is expressed in tissues undergoing angiogenesis (e.g., vascular sprouting) and in endothelial cells. By the phrase "angiogenic index," it is meant the extent or degree of vascularity of the tissue, e.g., the number or amount of blood vessels in the sample of interest. Amounts of nucleic acid or polypeptide can be assessed (e.g., determined, detected, etc.) by any suitable method. There is no limitation on how detection is performed.

For instance, if nucleic acid is to be assessed, e.g., an mRNA corresponding to a differentially-expressed gene, the methods for detecting it, assessing its presence and/or amount, can be determined by any the methods mentioned above, e.g., nucleic acid based detection methods, such as Northern blot analysis, RT-PCR, RACE, differential display, NASBA and other transcription based amplification systems, polynucleotide arrays, etc. If RT-PCR is employed, cDNA can be prepared from the mRNA extracted from a sample of interest. Once the cDNA is obtained, PCR can be employed using oligonucleotide primer pairs that are specific for a differentially-expressed gene. The specific probes can be of a single sequence, or they can be a combination of different sequences. A polynucleotide array can also be used to assess nucleic, e.g., where the RNA of the sample of interest is labeled (e.g., using a transcription based amplification method, such as U.S. Pat. No. 5,716,785) and then hybridized to probe fixed to a solid substrate.

Polypeptide detection can also be carried out by any available method, e.g., by Western blots, ELISA, dot blot, immunoprecipitation, RIA, immunohistochemistry, etc. For instance, a tissue section can be prepared and labeled with a specific antibody (indirect or direct), visualized with a microscope, and then the number of vessels in a particular field of view counted, where staining with antibody is used to identify and count the vessels. Amount of a polypeptide can be quantitated without visualization, e.g., by preparing a lysate of a sample of interest, and then determining by ELISA or Western the amount of polypeptide per quantity of tissue. Again, there is no limitation on how detection is performed.

In addition to assessing the angiogenic index using an antibody or polynucleotide probe specific for RUNX2delta8, other methods of determining tissue vascularity can be applied. Tissue vascularity is typically determined by assessing the number and density of vesssels present in a given sample. For example, microvessel density (MVD) can be estimated by counting the number of endothelial clusters in a high-power microscopic field, or detecting a marker specific for microvascular endothelium or other markers of growing or established blood vessels, such as CD31 (also known as platelet-endothelial cell adhesion molecule or PECAM). A CD31 antibody can be employed in conventional immuno-histological methods to immunostain tissue sections as described by, e.g., Penfold et al., *Br. J. Oral and Maxill. Surg.*, 34: 37-41; U.S. Pat. No. 6,017,949; Dellas et al., *Gyn. Oncol.*, 67:27-33, 1997; and others.

In addition to RUNX2delta8, other genes and their corresponding products can be detected. For instance, it may be desired to detect a gene which is expressed ubiquitously in the sample. A ubiquitously expressed gene, or product thereof, is present in all cell types, e.g., in about the same amount, e.g., beta-actin. Similarly, a gene or polypeptide that is expressed selectively in the tissue or cell of interest can be detected. A selective gene or polypeptide is characteristic of the tissue or cell-type in which it is made. This can mean that it is expressed only in the tissue or cell, and in no other tissue- or cell-type, or it can mean that it is expressed preferentially, differentially, and more abundantly (e.g., at least 5-fold, 10-fold, etc., or more) when compared to other types. The expression of the ubiquitous or selective gene or gene product can be used as a control or reference marker to compare to the expression of differentially-expression genes. Typically, expression of the gene can be assessed by detecting mRNA produced from it. Other markers for blood vessels and angiogenesis can also be detected, such as angiogenesis-related genes or polypeptides. By the phrase "angiogenesis-related," it is meant that it is associated with blood vessels and therefore indicative of their presence. There are a number of different genes and gene products that are angiogenesis-related, e.g., Vezf1 (e.g., Xiang et al., Dev. Bio., 206:123-141, 1999), VEGF, VEGF receptors (such as KDR/Flk-1), angiopoietin, Tie-1 and Tie-2 (e.g., Sato et al., Nature, 376:70-74, 1995), PECAM-1 or CD31 (e.g., DAKO, Glostrup. Denmark), CD34, factor VIII-related antigen (e.g., Brustmann et al., Gyn. Oncol., 67:20-26, 1997).

The topic headings set forth above are meant as guidance where certain information can be found in the application, but are not intended to be the only source in the application where information on such topic can be found. For other aspects of the polynucleotides, reference is made to standard textbooks of molecular biology. See, e.g., Hames et al., *Polynucleotide Hybridization*, IL Press, 1985; Davis et al., *Basic Methods in Molecular Biology*, Elsevir Sciences Publishing, Inc., New York, 1986; Sambrook et al., *Molecular Cloning*, CSH Press, 1989; Howe, *Gene Cloning and Manipulation*, Cambridge University Press, 1995; Ausubel et al., *Current Protocols in Molecular Biology*, John Wiley & Sons, Inc., 1994-1998.

The entire disclosure of all applications, patents and publications, cited above and in the figures are hereby incorporated by reference in their entirety, including U.S. Provisional Application Ser. No. 60/564,979, filed Apr. 26, 2004, which is hereby incorporated by reference in its entirety.

EXAMPLES

Example 1

Expression of the Runx2 Transcription Factor in Aortic Vascular Sprouts

Runx2 is a member of the family of Runx/AML transcription factors containing a Runt DNA-binding domain, a nuclear-localization signal, and several activation and repression domains (Westendorf & Hiebert, 1999). Runx genes have been shown to be expressed during angiogenesis in mouse neovasculature after treatment with FGF-2 (Namba et al., 2000; Sun et al., 2001). Rat aortic tissue was used to determine whether the Runx2 gene was also expressed during vascular sprouting in a physiologically relevant angiogenesis assay. This model recapitulates several steps in angiogenesis, such as expansion of the EC number, formation of cell-cell contacts, and subsequent growth arrest that are important in the formation of neovessels (Nicosia & Ottinetti, 1990). Runx2 expression was analyzed with Runx2-specific oligonucleotide primers corresponding to position 645 (upstream) and 1061 (downstream) in the C-terminal domain of the mouse and human Runx2 gene (Sun et al., 2001). These primers do not detect Runx1 or Runx3 expression (data not shown). Rat aortic explants were cultured within fibrin gels (FIG. 1A) under conditions that induce vascular sprouting (Hiraoka et al., 1998; Nicosia & Tuszynski, 1994), expression of VEGF (Nicosia et al., 1994; Nicosia & Tuszynski, 1994), and the expression of ECM-degrading proteases such as urokinase plasminogen activator, uPA (Rabbani, 1998) and membrane-type metalloproteinase, MT1-MMP (Hiraoka et al., 1998). A characteristic halo of vascular outgrowth was apparent 7 days after incubation of dissected rings at 37° C. (FIG. 1A). Expression of uPA was elevated 10-fold (normalized to cyclophilin) after 7 day culture in fibrin while MT1-MMP and VEGF increased by 7 days from undetectable levels (FIG. 1B, compare lanes 1 and 3). Expression of the expected 416 bp Runx2 product increased 3-fold (normalized to cyclophilin) in vascular sprouts relative to freshly dissected tissue. Interestingly, another PCR product (350 bp), which was not evident in freshly dissected tissue, was highly expressed in vascular sprouts by day 7 (FIG. 1B, lane 3). As control, mRNA was not detectable in fibrin gel (FG) without sprouts (FIG. 1B, lane 2).

Example 2

An Alternatively Spliced Variant of RUNX2 Lacking Exon 8 is Expressed in EC

RT-PCR amplification of RUNX2 in human bone marrow EC (HBME) also generated two products, one of the expected 416 bp size and a second of 350 bp in size (FIG. 2A, lane 1) as shown for aortic sprouts (FIG. 1). To verify that the 416 bp and 350 bp PCR products were authentic RUNX2, bands corresponding to these products from HBME cells were sequenced (FIG. 3). Sequence comparison showed that the 416 bp product was identical to the expected RUNX2 mRNA, while the 350 bp product was identical to RUNX2 except for a deletion of 66 bp near the 3'-end of the sequence (FIG. 3A). Comparison of the sequence of the smaller product with the published exon map (GenBank nucleotide sequence database (accession number NM_004348.1/GI:10863884) and the published intron/exon boundaries for RUNX2 (Geoffroy et al., 1998) revealed that the 350 bp PCR product corresponded to a RUNX2 mRNA with exon 8 deleted (designated RUNX2Δ8). Exon 8 encodes a peptide of 22 amino acids (FIG. 3B) that is unique to RUNX2 (Westendorf & Hiebert, 1999).

Figure 2:
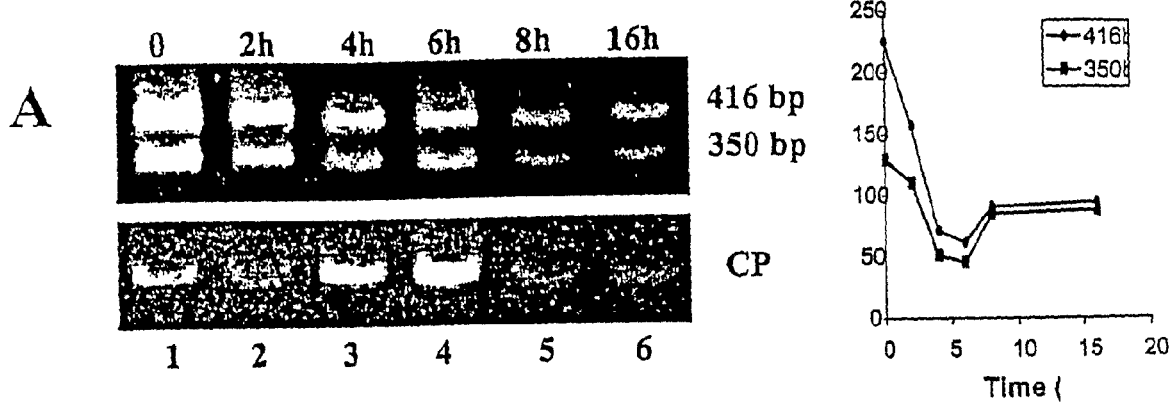
FIG. 2 (A-B). RUNX2 expression and mRNA stability in human EC. (A) Reduced RUNX2 levels in the absence of serum. RNA was isolated as described in the Methods section and expression determined with specific primers. Cyclophilin (CP) was used to normalize the RT-PCR reactions. HBME cells were grown to subconfluence, incubated in the absence of FBS for 0 to 16 hours (lanes 1-6) and RNA prepared as described in the Methods. RT-PCR was performed using RUNX2-specific primers. Band intensities were calculated by densitometry normalized to cyclophilin control and show a $t_{1/2}$=3 hr (A, right panel). Data are representative of 3 separate experiments. (B) HBME cells that were incubated in the absence of FBS for 16 hours were harvested with trypsin/EDTA and 5×10$^5$ cells/well were transferred to uncoated wells of a 6-well plate (PL; lanes 1,2), wells coated with EHS matrix gel (MG; lanes 3,4) or wells coated with fibrin gel (FG; lanes 5,6) in the presence of 10% FBS (lanes 1,3,5) or 0.1% BSA (lanes 2,4,6). Cells were incubated for 6 hours and RNA was prepared for RT-PCR with RUNX2-specific primers.
Figure 2:
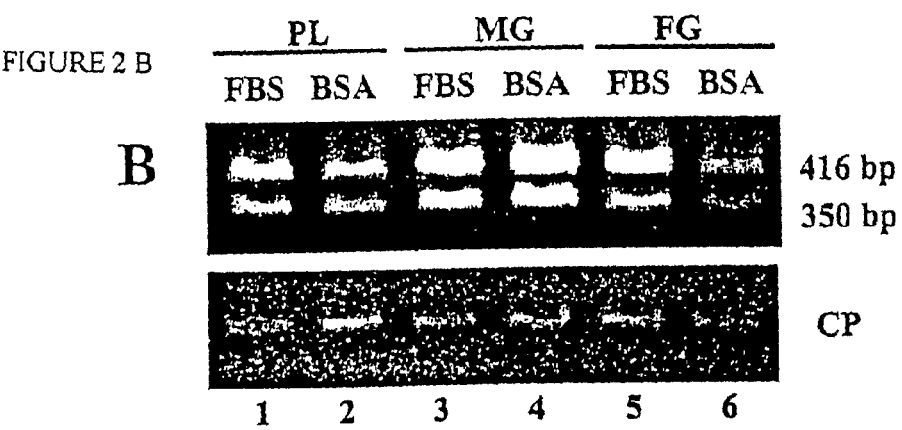

Previous data had shown that serum withdrawal results in rapid loss of expression of RUNX2 and that extracellular matrix proteins (ECM) mediate HBME differentiation, tube formation, and increased RUNX2 expression (Sun et al., 2001). The alternatively spliced RUNX2 isoform, RUNX2Δ8, also displayed a short half-life of 3 hr, relative to cyclophilin control in the absence of serum (FIG. 2A). Starved HBME cells were harvested and transferred to culture plates (PL) or to culture plates coated with two different ECM substrates: either fibrin gel (FG) or Matrigel (MG) in the presence (FBS) or absence (BSA) of serum (FIG. 2B). Culture on MG increased RUNX2 and RUNX2Δ8 mRNA expression about 1.8-fold and 1.6-fold, respectively, relative to PL and was independent of the presence of serum (FIG. 2C, compare lanes 1,2 and 3,4). However, cells cultured on a fibrin gel coating showed 1.4-fold elevated RUNX2 levels relative to PL only in the presence of serum (FIG. 2B, compare lanes 5 and 6). In other experiments, treatment of serum-starved cells with IGF-1 as before (Sun et al., 2001) stimulated comparable increases in expression of both RUNX2 isoforms, while RUNX2 isoforms in post-confluent cells were undetectable (data not shown).

Example 3

RUNX2 DNA-Binding Activity and EC Proliferation

Figure 4:
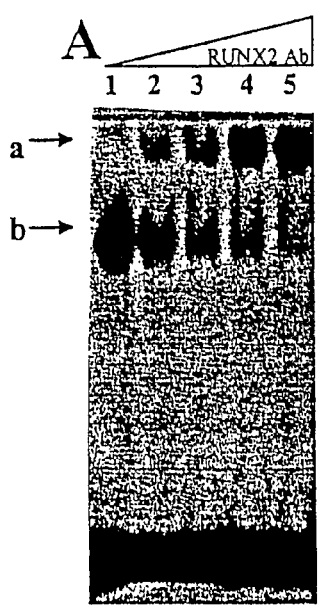
FIG. 4 (A-C). RUNX2 DNA-binding activity and EC proliferation. (A) Gel-shift assay to detect RUNX2 DNA-binding activity. Nuclear extracts prepared from HBME cells, which express endogenous RUNX2, were incubated without (lane 1) or with (lanes 2-5) increasing amounts of RUNX2-specific antibody and with the consensus RUNX2-binding oligonucleotide (SEQ ID NOS 43-44, respectively, in order or appearance) to verify the presence of RUNX2 in the binding complex. (B) RUNX2 DNA-binding activity in quiescent and proliferative EC. Nuclear extracts from subconfluent (lanes 1-4) or postconfluent (lanes 5-8) HBME cells were incubated with Runx2 antibody (lanes 2,6), with 100-fold excess unlabeled specific RUNX2-binding oligos (lanes 3,7), with 100-fold excess non-specific STAT-binding oligos (lanes 4,8), or were left untreated (lanes 1,5). (C) RUNX2 DNA-binding activity was determined in serum-starved HBME cells (lane 1), serum-starved HBME treated with 20 ng/ml IGF-1 (lane 2), or HEK293 cells transfected with Flag.tag RUNX2 (lane 3), or Flag.tag RUNX2Δ8 expressing plasmid (lane 4). Panel a represents EMSA, panel b represents Western blot of nuclear extracts for endogenous RUNX2 and RUNX2Δ8 (lanes 1,2) or Flag.tag RUNX2 or RUNX2Δ8 (lanes 3,4), and panel c is the Western blot loading control (total Akt). All samples were resolved on TBE-acrylamide DNA retardation gels. Arrows (A,B) indicate the RUNX2-specific shifted complex (b) and the RUNX2 antibody super-shifted complex (a). Similar results were obtained in three additional experiments.
Figure 4:
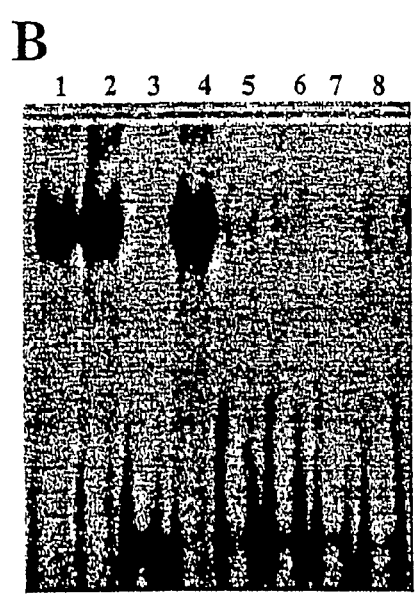
Figure 4:
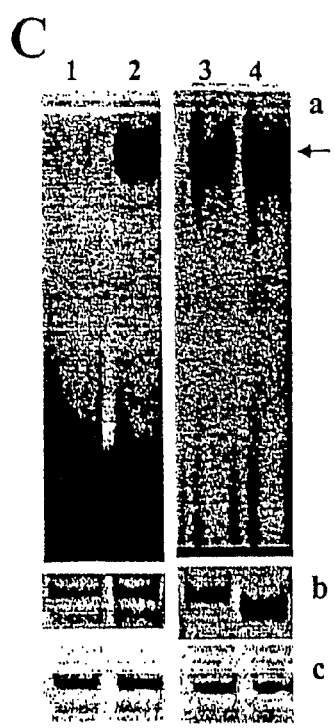

RUNX2 is a DNA-binding transcription factor that interacts with the promoters of specific target genes (Ito, 1999; Zelzer et al., 2001). To determine whether RUNX2 activity was involved in EC proliferation, endogenous RUNX2 DNA-binding was measured by EMSA in proliferating (subconfluent) and growth-arrested (postconfluent) EC (FIG. 4A, 4B). Nuclear extracts from HBME cells incubated with a consensus RUNX2-binding site oligonucleotide from the osteocalcin promoter (Duey et al., 1997) exhibited a shifted complex (FIG. 4A, lane1) that became super-shifted in the presence of RUNX2-specific antibody (FIG. 4A, lanes 2-5), suggesting that the predominant RUNX protein in these cells is RUNX2. Non-specific γ-tubulin antibody did not affect the shifted complex (data not shown). Subconfluent HBME cells expressed more intense DNA-binding activity than postconfluent cells (FIG. 4B, compare lanes 1,2 and 5,6). The shifted complex could be competed with excess, cold oligonucleotide (FIG. 4B, lanes 3,7), but not with a non-specific oligonucleotide (FIG. 4B, lanes 4,8). Our previous data had shown that the angiogenic growth factor, IGF-1, increases RUNX2 mRNA and protein levels in HBME cells (Sun et al., 2001). Consistent with a role for RUNX2 in EC proliferation, IGF-1 treated HBME cells also exhibited increased RUNX2 DNA-binding activity (FIG. 4C, lane 2) relative to cells cultured in the absence of serum but not treated with IGF-1 (FIG. 4C, lane 1). IGF-1 treatment also increased expression of endogenous RUNX2 and RUNX2Δ8 proteins (FIG. 4C, lane 2, panel b).

Figure 5:
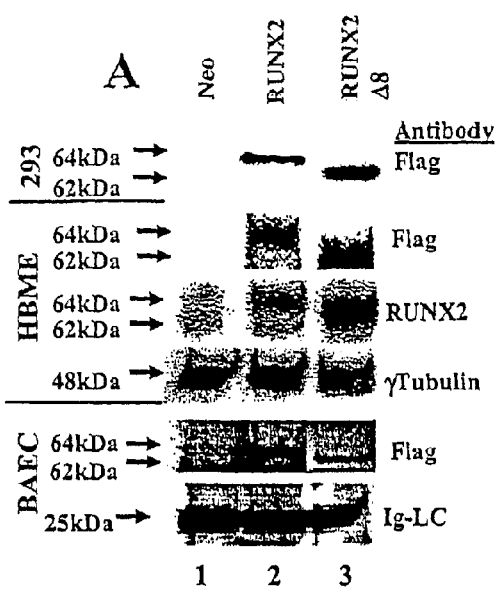
FIG. 5 (A-D). Ectopic expression of RUNX2 isoforms and EC proliferation. (A) Protein expression in HEK293, HBME, or BAEC cells transfected with Flag-tagged vectors encoding RUNX2 isoforms was detected by Western blots using M2 (Flag-tag; for HBME and BAEC) or AML3 (RUNX2; for HBME) antibodies. The blots were re-probed with γ-tubulin specific antibodies to verify equal loading. Flag-tag proteins from transfected BAEC were immunoprecipitated with M2 antibody and subjected to Western blotting. Ig-LC=immunoglobulin light chain. Data for BAEC are representative of 4 different sets of stable, polyclonal transfectants. (B) Stable transfectants of BAEC (Neo, RUNX2 and RUNX2Δ8) were grown to confluence, harvested, and re-cultured in 96-well plates ($1 \times 10^4$ cells/well). Cells were incubated for 4, 24, 48 or 72 hours at 37° C. MTT dye was used to detect viable cells. Absorbance at 540 nm was measured and expressed as the mean and SD from n=4-6 per point. (Bars=SD; *p<0.01 versus RUNX2Δ8 or neo at 72 hr). (C) Stable transfectants of BAEC (Neo, RUNX2 and RUNX2Δ8) were re-plated after confluence in a 96-well plate in serum-containing medium for 4 h, 8 h, 24 h, 48 h or 72 h, with ($^3$H)-thymidine added to the medium for the final 1 hour. Total cellular protein was determined from duplicate cultures and incorporation of label was normalized to cell protein content. n=3 for each experimental group. (p<0.01 versus RUNX2Δ8 or neo at 24 or 48 hr). (D) BAEC cells were transfected with 0.6 ug of the indicated cDNA and 6 ul lipofectin for 4 hr in serum-free media. Serum (10%) was added for 18 hr and the cells were serum starved for 48 hr prior to treatment with 10% FBS for 0, 3, or 6 hr as indicated. Western blotting with anti-Rb and γ-tubulin control antibodies is shown.
Figure 5:
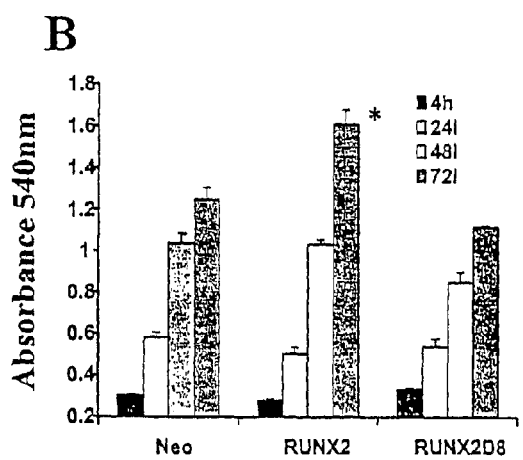
Figure 5:
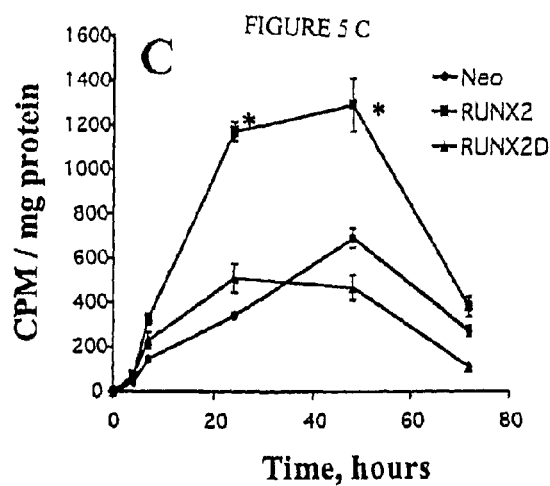
Figure 5:
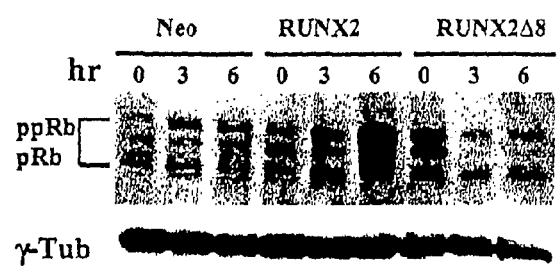

To determine whether RUNX2 or RUNX2Δ8 might regulate EC proliferation, vectors were prepared that would allow independent overexpression of each of these isoforms. Ectopic expression of RUNX2 and RUNX2Δ8 FLAG-tagged proteins was confirmed in transiently-transfected HEK293 cells (FIG. 4C, lanes 3,4). Nuclear extracts from HEK293 cells transfected with either RUNX2 (lane 3) or RUNX2Δ8 (lane 4) expressed similar levels of RUNX protein (FIG. 4C, panel b) and exhibited similar RUNX2 DNA-binding activity (FIG. 4C, panel a). Pooled, stably transfected HBME and bovine aortic EC (BAEC) also expressed ectopic RUNX2 by immunoblotting (FIG. 5A, lanes 2 and 3). Primary BAEC, which express low levels of endogenous Runx2, were used in subsequent growth assays. Confluent (synchronized) BAEC transfectants were harvested, replated in serum-containing medium for 4, 24, 48, or 72 h and examined for growth rate using the MIT dye reduction assay. Over 3 days in culture, RUNX2 transfectants exhibited a greater increase in cell number (5.3-fold) than neo control (4.2-fold) or RUNX2Δ8 (3.6-fold) transfectants (FIG. 5B). Analysis of DNA synthesis rates, determined using thymidine incorporation assays, were consistent with these results. RUNX2 transfectants exhibited 2-fold higher thymidine incorporation by 24 and 48 hours in culture than neo or RUNX2Δ8 transfectants (FIG. 5C). By 72 hr, cells had reached confluence and became growth arrested. In addition, treatment of serum-starved RUNX2-transfected cells with serum for 3 or 6 hr resulted in a dramatic increase in phosphorylated retinoblastoma (pRb) protein, indicative of progression into the cell cycle. pRb levels in RUNX2Δ8-transfectants declined under the same conditions, while Neo transfectants showed a modest increase in pRb. These data suggest that RUNX2 is involved in the regulation of EC growth.

Example 4

TGFβ$_1$-Mediated Growth Inhibition and Apoptosis

TGFβ$_1$ functions as an angiogenic modulator by inhibiting the growth of EC and stimulating matrix protein synthesis and EC migration (Kalluri & Sukhatme, 2000; Taipale & Keski-Oja, 1997). To determine if BAEC cells expressing the RUNX2 isoforms retained their sensitivity to TGFβ$_1$ growth modulation, post-confluent cells were harvested, replated, and cultured in the presence or absence of TGFβ$_1$ for 48 hours (FIG. 6A). Treatment of BAEC control (neo) transfectants with as little as 0.2 ng/ml TGFβ$_1$ resulted in 50% inhibition of cell growth and 80% inhibition when cells were treated with 20 ng/ml TGFβ$_1$ (FIG. 6B). RUNX2Δ8 transfectants treated with TGFβ$_1$ responded similarly. However, treatment of RUNX2-transfected cells with 0.2 or 2.0 ng/ml TGFβ$_1$ did not affect cell growth while treatment with 20 ng/ml inhibited growth by only 40%. Previous data from our laboratory had shown that expression of the dominant negative Runt DNA-binding domain of RUNX2 could inhibit EC migration (Sun et al., 2001). To determine whether RUNX2 expression could regulate EC migration in the presence of TGFβ$_1$, BAEC transfectants were spot cultured with a collagen overlay, treated with 10 ng/ml TGFβ, and sprouting from the central cell mass was examined (FIG. 6C, left panels). RUNX2-transfected cells showed a more robust sprouting response than NEO transfectants. RUNX2Δ8 transfected cells also exhibited a sprouting response, although the cells appeared more condensed and the nuclei more fragmented than NEO or RUNX2 transfectants (FIG. 6C, right panels).

Figure 6:
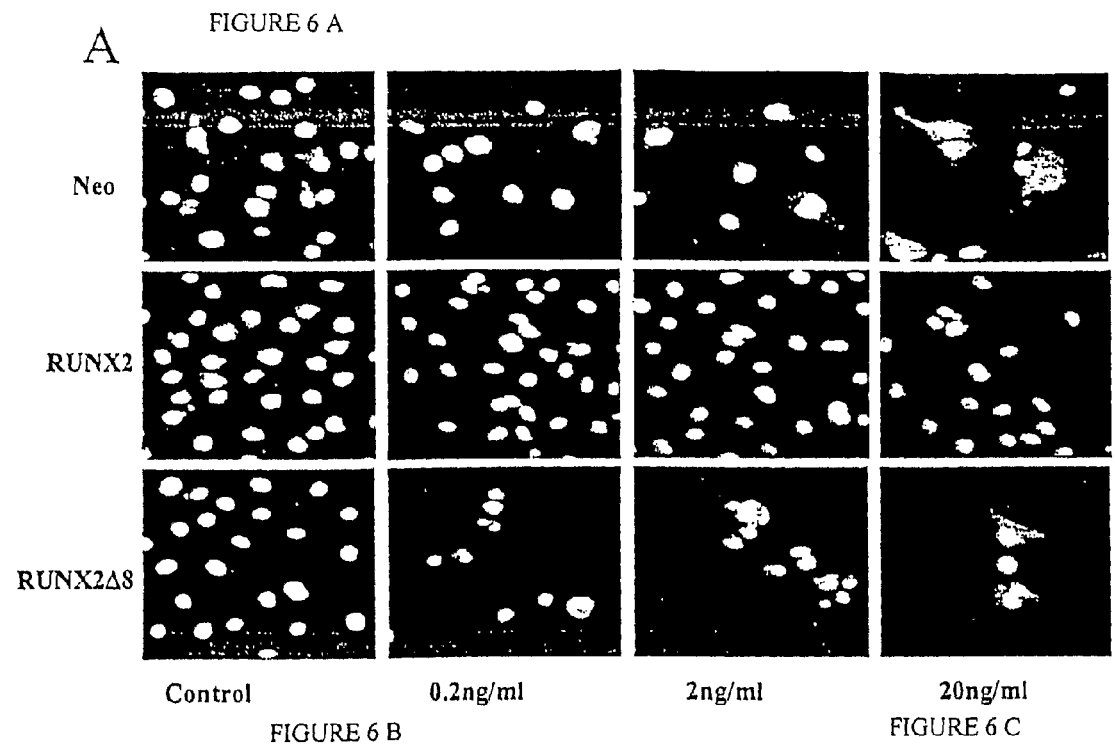
FIG. 6 (A-C). RUNX2 suppresses the $TGF\beta_1$-mediated inhibition of EC proliferation. (A) BAEC transfectants were cultured in 6-well plates ($5 \times 10^5$/well) and treated with $TGF\beta_1$ (0, 0.2, 2.0, 20 ng/ml) for 48 hours. Cells were fixed with PBS-buffered formalin and stained with DAPI to visualize nuclei at 320× magnification. (B) For each treatment condition, cells in the fluorescent images were counted (four fields/well) and expressed as the number of cells/field versus $TGF\beta_1$ concentration. The data represent the mean and standard deviations (bars) with * indicating statistically significant differences between RUNX2 and neo or RUNX2Δ8 transfectants (p<0.01 at 0.2 ng/ml; p<0.05 at 2.0 and 20 ng/ml). (C) BAEC transfected with control (NEO), RUNX2, or RUNX2Δ8 were spot cultured in 6-well plates and overlayered with collagen gel (3 mg/ml) in the presence of TGFβ (10 ng/ml) for 48 hr (left panels). Higher magnification shows a representative cell from each well indicating DNA fragmentation in RUNX2Δ8 transfectants (right panel).
Figure 6:
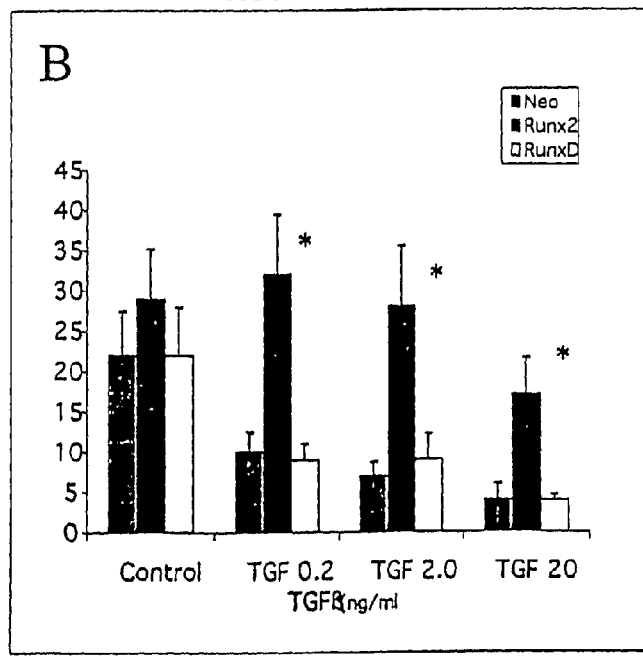
Figure 6:
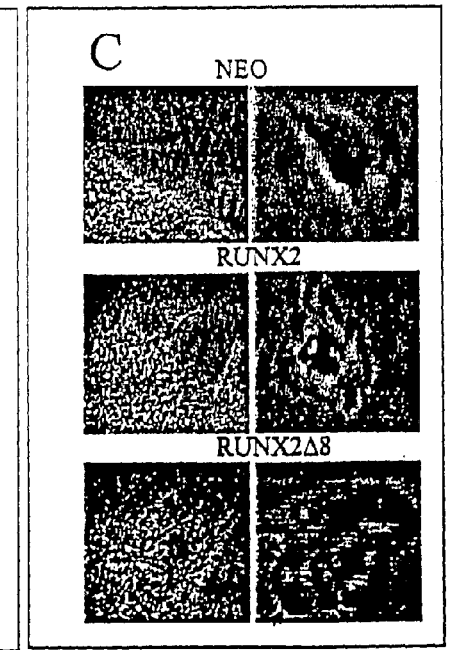
Figure 7:
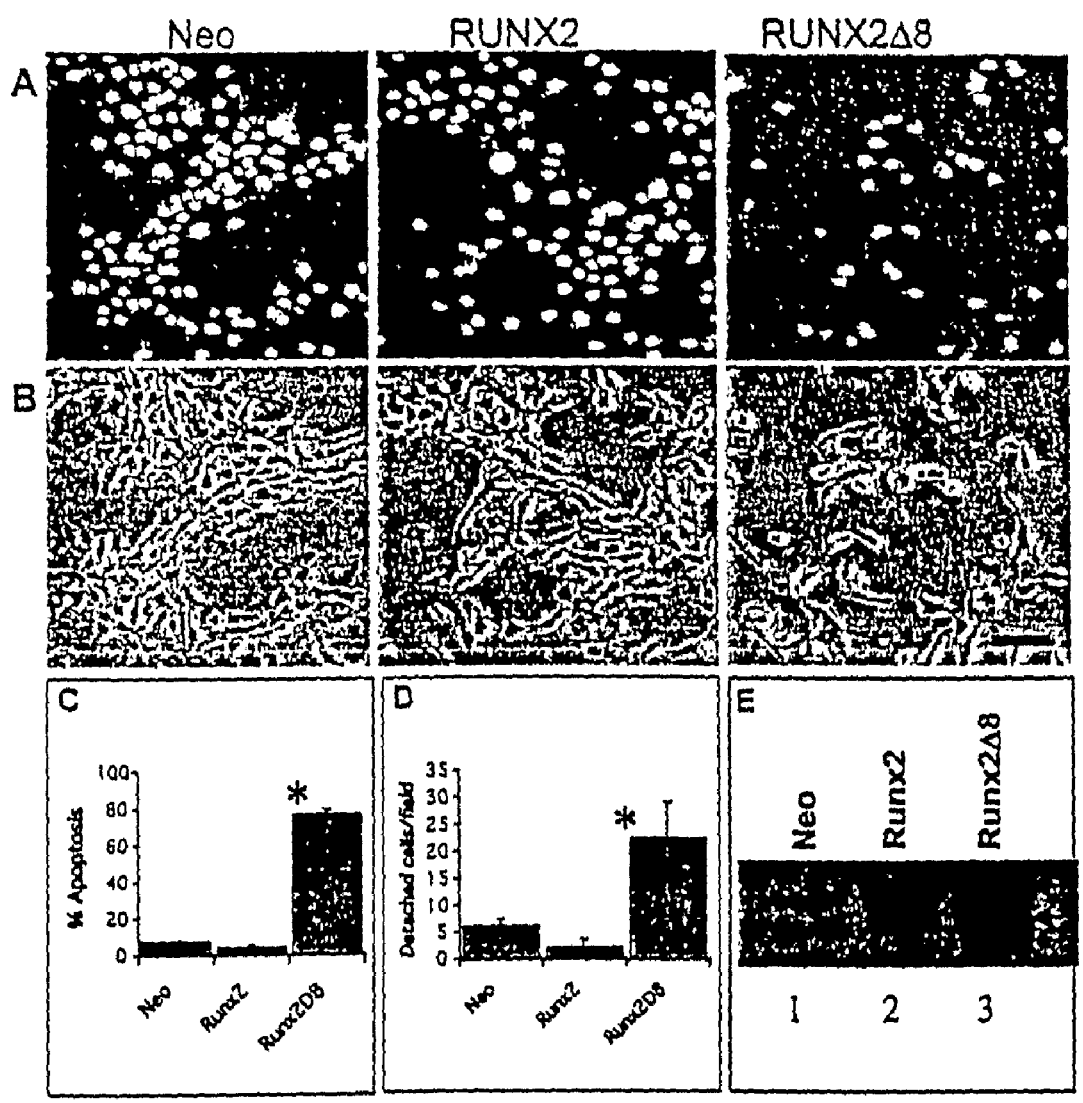
FIG. 7 (A-E). RUNX2Δ8 reduces survival in $TGF\beta_1$-treated EC. (A,B) BAEC ($5 \times 10^5$/well) were cultured in 6-well plates in the presence of 0.2% FBS and $TGF\beta_1$ (2 ng/ml) for 28 hours. Cells were then fixed with PBS-buffered formalin, stained with DAPI to detect nuclei and photographed with an epifluorescence microscope. Neo, RUNX2, and RUNX2Δ8 transfectants were compared under fluorescence (A) or phase contrast (B). (Bars, 1 cm, =100 um). (C) The degree of apoptosis is expressed as the % of total cells in a given photographic field whose nuclei display the morphologic features of apoptosis. At least 3 photographic fields for each transfectant were used for quantitation. (D) Detached, DAPI-stained cell nuclei were counted under low power and the number of detached cells per field (a minimum of 3 fields per transfectant) were quantitated. All detached cells exhibited condensed nuclei characteristic of apoptosis. Statistical significance was calculated using Student's t-test from the means±SD. (*p<0.01 versus neo or RUNX2) (E) Representative Western blot of neo (lane 1), RUNX2 (lane 2), and RUNX2Δ8 (lane 3) transfected EC after $TGF\beta_1$ treatment. Anti-Parp antibodies were used to confirm the presence of caspase activity. Arrows indicate uncleaved and cleaved Parp substrate.

Cell growth is a balance of positive (proliferation) and negative (apoptosis) events and RUNX2 transfectants continued to grow past confluence, while RUNX2Δ8-transfected cells did not (FIG. 5) with some evidence of apoptosis when treated with TGFβ$_1$ (FIG. 6C). To determine whether RUNX2Δ8 expression contributed to apoptosis, post-confluent BAEC transfectants were harvested and replated in low serum in the presence of 2 ng/ml TGFβ$_1$. After 28 hours, cells were fixed with formaldehyde and stained with DAN to detect apoptotic nuclei (FIG. 7A). While neo and RUNX2 transfectants remained attached (FIG. 7B) and exhibited low levels of apoptosis (FIG. 7C), RUNX2Δ8 transfectants appeared more loosely attached (note rounded cells in FIG. 7B) with a higher percentage of apoptotic cells (FIG. 7C). Nuclei were condensed and in many cases fragmented, consistent with apoptosis. In addition, more detached RUNX2Δ8 transfected cells were evident relative to neo or RUNX2 transfectants (FIG. 7D) and increased cleavage of the caspase substrate, PARP, was observed in RUNX2Δ8 transfectants (FIG. 7E). By morphological criteria, approximately 8-fold more RUNX2Δ8 transfectants were apoptotic than were neo or RUNX2 transfectants (FIG. 7C). The number of RUNX2Δ8 detached cells was 4 to 8-fold higher than neo or RUNX2 transfectants, respectively (FIG. 7D). However, RUNX2Δ8 transfectants did not exhibit any evidence of reduced proliferation in the absence of TGFβ$_1$ (FIG. 6). These results suggest that RUNX2, and more specifically its exon8 domain, is involved in antagonizing TGFβ$_1$-mediated growth inhibition and in reducing TGFβ$_1$-mediated EC apoptosis.

Example 5

Figure 8:
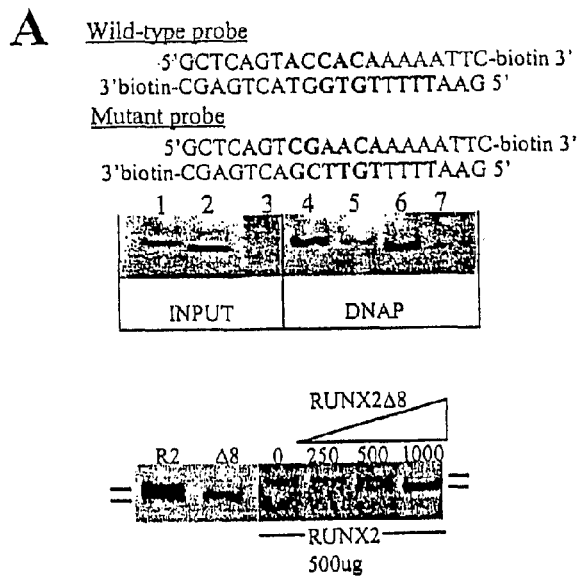
FIG. 8 (A-D). Regulation of the $p21^{CIP1}$ promoter by RUNX2 and RUNX2Δ8. (A) RUNX2 and RUNX2Δ8 binding to a $p21^{CIP1}$ promoter RUNX-binding element. HEK293 cells were transfected with Flag.tag RUNX2 (lane 1), RUNX2Δ8 (lane 2), or control (lane 3) vectors, nuclear extracts were prepared, and Flag.tag proteins were detected by Western blotting. Nuclear extracts were incubated with biotin-labeled wild-type (lanes 4,6) or mutant (lanes 5,7) double-stranded oligonucleotides, the protein-DNA complexes were isolated with Streptavidin beads, and the Flag.tag RUNX2 (lanes 4,5) or RUNX2Δ8 (lanes 6,7) proteins were detected by Western blotting. The lower panel indicates the ability of RUNX2Δ8 (Δ8) to compete with RUNX2 (R2) for the DNA binding site. Increasing amounts of nuclear protein from RUNX2Δ8-transfected cells were incubated with 500 ug of protein from RUNX2-transfected cells and RUNX2 or RUNX2Δ8 bound to DNA was detected by Western blotting. Arrows indicate positions of each isoform. Figure discloses SEQ ID NOS 19-22, respectively, in order or appearance (B,C,D) NIH3T3 cells ($2 \times 10^5$/well) were transfected with the Mirus LT1 reagent and the $p21^{CIP1}$-promoter luciferase plasmid in the presence of TK-Renilla plasmid as control. The neo, RUNX2, or RUNX2Δ8 plasmids were co-transfected for 42 hours and cells were left untreated (B) or treated (C) with $TGF\beta_1$ (2 ng/ml) for an additional 6 h prior to preparation of the lysates for analysis with the Dual-Luciferase system. For competition experiments (D), basal levels of RUNX2 (0.25 ug), Alk5TD (0.05 ug), and Smad3 (0.05 ug) plasmids were co-transfected with RUNX2Δ8 plasmid (0.05 ug) as indicated. Each transfection was performed in triplicate and measurements were recorded two separate times. For detection of $p21^{CIP1}$ protein (D, inset), cells were treated with 0.1 uM doxorubicin for 24 hr prior to analysis of nuclear extracts by Western blotting. Each experiment was repeated four (B) or three (C,D) times. Firefly luciferase activity relative to *Renilla luciferase* (B, D) or the fold-change in repression or activation (C) was calculated relative to untransfected cells.
Figure 8:
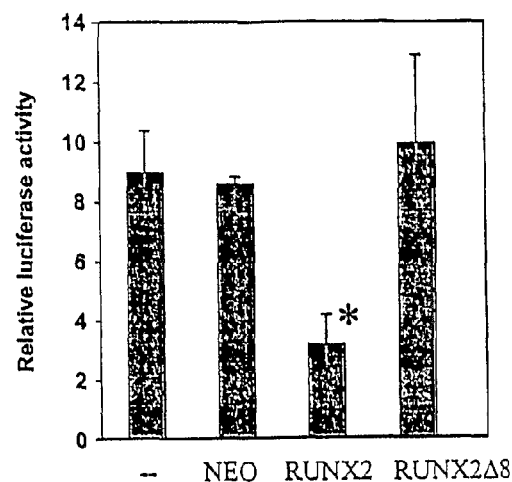
Figure 8:
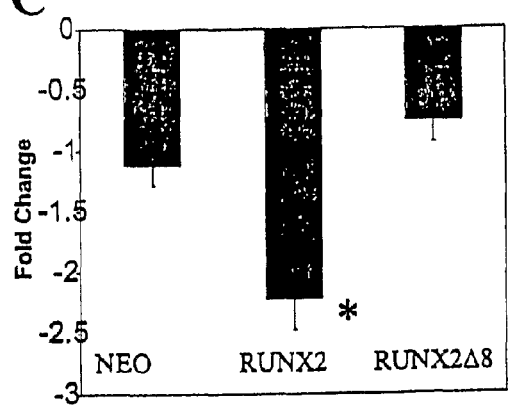
Figure 8:
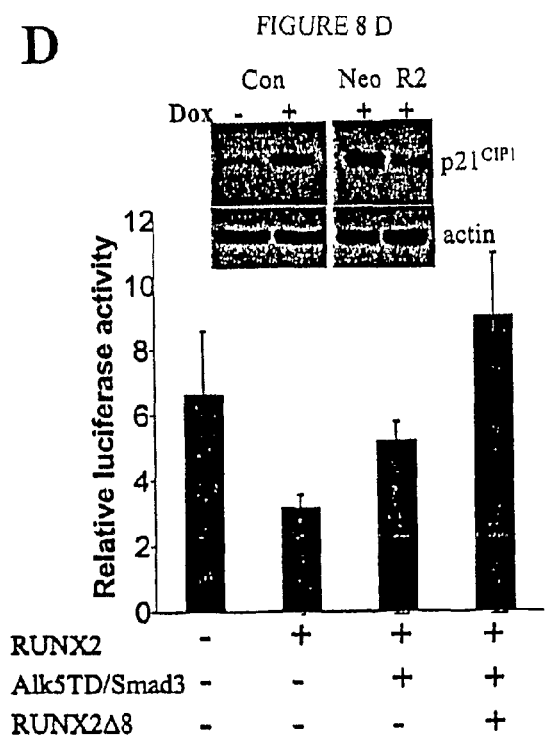

Regulation of the Promoter of the Cyclin-Dependent Kinase Inhibitor p21$^{CIP1}$ by RUNX2 Isoforms Inhibition of EC proliferation by TGFβ$_1$ is mediated through activation of the p21$^{CIP1}$ promoter via a p53-independent mechanism (Datto et al., 1995) whereas RUNX2 is a strong transcriptional repressor of the p21$^{CIP1}$ promoter (Westendorf et al., 2002). To determine whether deletion of the exon8 domain would alter RUNX2 transcriptional regulation of the p21$^{CIP1}$ promoter, RUNX2Δ8 DNA binding and transactivation functions were evaluated. EMSA using the RUNX-binding element in the osteocalcin promoter (FIG. 4) or a DNA precipitation assay with a biotin-labeled RUNX-consensus binding site oligonucleotide from the p21$^{CIP1}$ promoter (FIG. 8A, lanes 4,6) indicated no differences in relative DNA binding between RUNX2 and RUNX2Δ8 isoforms. Control mutant oligonucleotide (FIG. 8A, lanes 5,7) did not interact with RUNX2 or RUNX2Δ8. In addition, RUNX2Δ8 was able to displace RUNX2 from the p21$^{CIP1}$ promoter target oligonucleotide (FIG. 8A, lower panel). Therefore, the ability of RUNX2Δ8 to repress the p21$^{CIP1}$ promoter was examined (FIG. 8 B,C,D). Co-transfection of the p21$^{CIP1}$-promoter-Luciferase vector with RUNX2 in NIH3T3 cells resulted in 3-fold repression of endogenous p21$^{CIP1}$ promoter activity (FIG. 8B), while the same dose of RUNX2Δ8 or control plasmid (neo) did not inhibit basal activity. In cells treated with TGFβ$_1$ (2 ng/ml), RUNX2 overexpression also repressed the p21$^{CIP1}$ promoter (FIG. 8C) by 2.2-fold, while neo and RUNX2Δ8 expression vectors did not. In the presence of Smad3 and constitutively-active TGFβ receptor (Alk5TD), RUNX2Δ8 was able to compete with RUNX2 to inhibit RUNX2-mediated repression of the p21$^{CIP1}$ promoter and to increase p21$^{CIP1}$ promoter-Luciferase activity above baseline (FIG. 8D). Consistent with these data, RUNX2 could also inhibit the induction of p21$^{CIP1}$ protein in cells treated with doxorubicin, a chemotherapeutic agent that increases p21$^{CIP1}$ expression (FIG. 8D, inset). These results indicate that the antagonism of RUNX2 for TGFβ$_1$-induced growth inhibition in EC may be mediated, in part, by its ability to repress the cyclin-dependent kinase inhibitor p21$^{CIP1}$ and that the presence of exon 8 is important for this effect.

Materials and Methods for Examples 1-5

Reagents

Flag-M2 monoclonal, β-tubulin, and γ-tubulin antibodies were obtained from Sigma (St. Louis, Mo.). The pRb antibody, which recognizes unphosphorylated and phosphorylated forms of Rb was from BD Biosciences (cat# 554136). Human TGF-β$_1$ was from R&D Systems, (Minneapolis, Minn.) and the AML3/Cbfa1/RUNX2 antibody was from Oncogene Research Products (Cambridge, Mass.). Parp-specific antibody was from Roche Diagnostics Corp. (Indianapolis, Ind.). p21$^{CIP1}$-specific antibody was obtained from Santa Cruz, Inc. (cat# sc-397). The RUNX2 cDNA clone (PEBP2aA) was obtained from Dr. Yoshiaki Ito (Institute of Molecular and Cell Biology, Singapore) (Ogawa et al., 1993), the p21$^{CIP1}$-promoter-Luciferase vector, WWP-Luc, (el-Deiry et al., 1993) from Dr. Bert Vogelstein (Johns Hopkins University, Baltimore, Md.), the Smad3 expression vector from Drs. Mark de Caestecker (Vanderbilt University) and Anne-Christine Poncelet (Northwestern University), and the constitutively active TGFβ receptor, Alk5TD, from Dr. Mitsuyasu Kato (University of Tsukuba, Japan).

Cell Culture

Human bone marrow EC, HBME-1, (Lehr & Pienta, 1998), a gift from Dr. Kenneth Pienta (University of Michigan Comprehensive Cancer Center) and bovine aortic endothelial cells (BAEC), purchased from the Coriell Cell Repository (Camden, N.J.), were maintained in Dulbecco's modified Eagle's medium (DMEM) containing 10% FBS and antibiotics (Penicillin, Streptomycin, AmphotericinB) from Life Technologies Inc. (Rockville, Md.). BAEC cells were used at passage 8 or less. HBME-1 were used between passage 14 and 24. The human embryonic kidney 293T cells were provided by Dr. Robert Fenton, University of Maryland School of Medicine and cultured in DMEM containing 10% FBS.

Angiogenesis Assays

Vascular sprouting was performed using aortas from 2-month old Sprague-Dawley rats (Harlan, Indianapolis, Ind.). Tissue was dissected and sections were implanted in fibrin gels as described (Nicosia & Ottinetti, 1990; Nicosia & Tuszynski, 1994). After culturing for one week at 37° C., vascular sprouts were photographed and extracted with Trizol reagent (Invitrogen, Carlsbad, Calif.) to isolate RNA. BAEC sprouting in vitro was determined by plating 5×10$^4$ cells in 50 ul of complete medium (DMEM containing 10% FBS) for 6 hr, removing the medium, and overlaying the attached cells ("spot culture") with a 3 mg/ml solution of neutralized type I collagen gel (Nicosia & Ottinetti, 1990; Nicosia & Tuszynski, 1994). Complete medium was added to the cultures, cells were incubated for 3 days and sprouting from the central spots was documented with a video camera attached to a Zeiss microscopy and analyzed with image analysis software (Oncor Image, Inc.).

RT-PCR

Expression of Runx2, the protease genes uPA and MT1MMP, and the angiogenic factor, VEGF, was determined after RNA extraction using standard PCR methods and the following primers: 5'-GCACAGACAGAAGCTTGAT-3' (SEQ ID NO: 5) and 5'-CCCAGTTCTGAAGCACCT-3' (SEQ ID NO:6) (RUNX2/416/350 bp); 5'-CCGGACTATA- CAGACCATCT-3' (SEQ ID NO: 7) and 5'-AGTGT-GAGACTCTCGTGTAG-3' (SEQ ID NO: 8) (uPA/367 bp); 5'-GCATTGGGTGTTTGATGAGG-3' (SEQ ID NO:9) and 5'-GTTCTACCTTCAGCTTCTGG-3' (SEQ ID NO: 10) (MT1MMP/327 bp); 5'-TGCACCCATGGCAGAAG-GAGG-3' (SEQ ID NO: 11) and 5'-TCACCGCCTCGGCT-TGTCACA-3' (SEQ ID NO: 12) (VEGF/564-360 bp); 5'-CATCCTGAAGCATACAGGTC-3' (SEQ ID NO:13) and 5'-CAGAAGGAATGGTTTGATGG-3' (SEQ ID NO: 14) (Cyclophilin/276 bp). Amplification of all genes was performed on a PTC-100 programmable thermal controller (MJ Research Inc., Watertown, Mass.), as described (Sun et al., 2001). For VEGF amplification, PCR was carried out using conditions as described previously (Burchardt et al., 1999). Linear conditions were established by varying the levels of input cDNA. Relative inducible levels of expression were calculated after scanning densitometry using cyclophilin gene expression to normalize for loading. All PCR products were sub-cloned into the pGEM-T vector (Promega Corporation, Madison, Wis.) and sequenced at the UMB Biopolymer Core Facility to verify gene identity.

Preparation of Expression Vectors

PCR sub-cloning with the FLAG-pCMV-Tag epitope mammalian expression vector pCMV-Tag2 (Stratagene, La Jolla, Calif.) and the full-length PEBP2aA cDNA vector, pEFBoSαA1, (Ogawa et al., 1993) were used to construct the RUNX2 and RUNX2Δ8 expression plasmids (pCMV-Tag-RUNX2 and pCMV-Tag-RUNX2Δ8, respectively). PCR sub-cloning and the following RUNX2-specific primers were used. Full-length RUNX2: 5'-AGATCTGATGCGTATTCCTGTAGATCCG-3' (SEQ ID NO: 15) (N-terminal with end of BglII site); 5'-CT CTCGAGTCAATATGGTCGCCAAACAG-3' (SEQ ID NO: 16) (C-terminal with end of XhoI site). RUNX2Δ8: 5'-CAG-TATGAGAGTAGGTGTCC-3' (SEQ ID NO: 17) (N-terminal; BsgI 778)(722-741); 5'-AAGGGTCCACTCTG-GCTTTG-3' (SEQ ID NO: 18) (C-terminal; XcmI 1255; 1248-1268). The full-length RUNX2 primers were used to amplify the full coding cDNA of RUNX2 with the pEF-BOSαA1 plasmid as template. The amplified fragment was purified and subcloned into pGEM-T vector (Promega Corporation, Madison, Wis.). After sequencing to verify the RUNX2 gene, the insert was subcloned in-frame into the BglI and XhoI sites of the pCMV-Tag epitope mammalian expression vector pCMV-Tagg (Stratagene, La Jolla, Calif.). RUNX2Δ8 expression plasmid pCMV-Tag-RUNX2Δ8 was constructed using HBME cDNA as template and PCR amplification using the RUNX2Δ8 primers above. The resulting fragment of 486 base pair was subcloned into the pGEM-T vector. Sequence analysis confirmed the identity of this short fragment to encompass the exon 8 deletion. The exon 8 deletion fragment was released from pGEM-T and subcloned into the BsgI and XcmI sites of the pCMV-Tag-RUNX2 vector.

Cell Transfection

Transfection of HBME-1 or BAEC was carried out with Superfect transfection reagent according to the protocol provided by the manufacturer (Qiagen Inc., Valencia, Calif.) or with Lipofectin (Gibco/BRL, Rockville, Md.) or Mirus TransIT LT1 (Mirus Corporation, Madison, Wis.). Approximately 2ug DNA were used for each 12 ul of transfection reagent. Two days after transfection, stable transfectants (polyclonal) were selected with 0.8 mg/ml (HBME) or 0.4 mg/ml (BAEC) of geneticin (Life Technologies Inc., Rockville, Md.) for two weeks. Western blotting was used to confirm the expression of RUNX2 and RUNX2Δ8 using the M2 anti-Flag-Tag antibodies as described below. For experimental results described in the text, four independent sets of selected polyclonal BAEC transfectants were used after fresh transfection with the RUNX plasmids, with essentially similar results from each set. Since BAEC are primary cells with a limited life-span, experiments were carried out within two weeks of selection. HEK293 cells were transfected using the calcium phosphate method (Gibco/BRL, Rockville, Md.).

DNA Synthesis

Thymidine incorporation into acid-insoluble DNA was determined in BAEC cultured as described above. Cells were incubated for 48 h until confluent and sub-cultured into 96-well microliter plates. A total of $1 \times 10^4$ cells per well were seeded in triplicate. Following incubation at 37° C. for 4, 8, 24, 48 or 72 h, in a humidified atmosphere with 5% $CO_2$, $^3$H-thymidine (1 uCi/well) was added and the incubation was continued for an additional 1 h. Cells were washed with cold Phosphate-Buffered Saline (PBS) and fixed in ice-cold 5% trichloroacetic acid to extract unincorporated radionucleotide. Acid-insoluble material from BAEC was dissolved in 100 ul of 1N sodium hydroxide and neutralized with 100 ul of 1N HCl. $^3$H-thymidine incorporation was quantitated with a liquid scintillation counter (Beckman Model LS5801). Incorporation of label was normalized to cell protein content. Results are expressed as $^3$H-thymidine dpm incorporated per ug protein with n=3 for each experimental group.

Cell Proliferation and Apoptosis Assays

BAEC cell growth was quantitated using the MTT dye reduction assay (Wang & Passaniti, 1999). Cells were cultured in 96-well plates ($1 \times 10^4$ cells/well) for 4, 24, 48 or 72 hours at 37° C. in 100 ul DMEM containing 10% FBS. MTT dye (10 ul of a 5 mg/ml stock in PBS) was added per well. After incubation at 37° C. for 4 hours, the crystalline formazan product was solubilized in 100 ul of 10% SDS+0.01N HCl for 16 hours and absorbance at 540 nm was measured with a BioRad Model 5450 plate reader. Mean and SD from the mean were calculated from n=4-6 per point. To measure the effect of $TGF\beta_1$ treatment on BAEC proliferation, post-confluent cells were harvested and $1 \times 10^5$ cells were replated per well of a 6-well plate. Cells were cultured in growth media in the presence or absence of $TGF\beta_1$ (0.2, 2.0, 20 ng/ml) for 48 hours and fixed with 3.7% PBS-buffered formaldehyde. DAPI stain (1 ug/ml; Molecular Probes, Inc., Eugene, Oreg.) was added to formaldehyde-fixed cells to visualize nuclei and representative fields from each well were photographed. Cell number was calculated by counting individual nuclei from at least three fields of each well. To measure the effect of $TGF\beta_1$ on BAEC apoptosis, post-confluent cells were harvested and replated in 0.2% FBS in the presence of 2 ng/ml $TGF\beta_1$ in 6-well plates as described for proliferation. After 28 hours, cells were fixed with formaldehyde and stained with DAPI to detect apoptotic nuclei. Apoptosis was quantitated by counting the number of apoptotic nuclei (using morphological parameters of nuclear condensation and fragmentation). Detached cells were counted by collecting the media from each well and adding 100 ul of each supernatant to glass slides, overlayed with coverslips. To measure cleavage of the caspase 3 substrate, Parp, cells were lysed in SDS-PAGE buffer, proteins were resolved on SDS-PAGE and the 116 kDa/80 kDa Parp proteins were detected by Western blotting.

Protein Extraction and Immunoblot

For whole cell lysate preparation, $1 \times 10^7$ cells were harvested and lysed in 1 ml of lysis buffer (50 mM Tris-HCl, pH 7.4, 150 mM NaCl, 1 mM DTT, 4 mM EDTA, 50 mM NaF, 0.1 mM $Na_3VO_4$, 1 mM PMSF, 10 ug/ml leupeptin, 10 ug/ml pepstatin A, 10 ug/ml chymostatin, 1% NP-40 and 0.1% Triton X-100). After incubation at 4° C. for 15 min, the lysate was cleared by micro-centrifugation at 10,000 g for 10 min at 4° C. The protein concentration in each sample was determined with the BioRad Bradford assay. Equal amounts of protein (15 ug) were denatured by heating to 95° C. in Laemmli sample buffer and were resolved by 12% SDS-PAGE, followed by transfer to PVDF membranes. The membranes were probed with the indicated antibodies and detected using an ECL system per manufacturer's recommendation (Amersham Pharmacia Biotech, Buckinghamshire, England). γ-tubulin was used as a loading control and was measured by re-probing the stripped membranes with anti-γ-tubulin antibody (Sigma, St. Louis, Mo.). In some cases, immunoprecipitated protein (M2-Flag antibody) from RIPA lysates was resolved on SDS-PAGE prior to Western blotting.

Electrophoretic Mobility Shift Assays and DNA Precipitation

Nuclear extracts were prepared by hypotonic lysis of cells and extraction of nuclear proteins with high salt buffer (Wang & Passaniti, 1999). Labeled double-stranded oligonucleotide containing the consensus RUNX-binding promoter element TGTGGTT was mixed with nuclear extracts and binding complexes were resolved on 6% TBE polyacrylamide gels. Specific RUNX2 antibody (0-0.4 ug) and non-specific, control (γ-tubulin) antibody were used to verify the presence of RUNX2 in the shifted complex. Cold 100-fold excess specific (RUNX binding site) or 100-fold excess non-specific (Stat binding site) oligonucleotides were used as controls. For DNA precipitation assays (DNAP), wild-type or mutant double-stranded oligonucleotides containing a RUNX-binding site from the p21$^{CIP1}$ promoter were incubated with nuclear extracts expressing Flag.Tag.RUNX2 or Flag.Tag.RUNX2Δ8 and specific complexes were isolated with streptavidin-Agarose beads.

Luciferase Assays

The Dual Luciferase kit from Promega (Madison, Wis.) was used to quantitate repression or activation of the p21-promoter by RUNX2 isoforms or TGFβ, respectively. Briefly, NIH3T3 cells were plated in 6-well plates at a density of $1.2 \times 10^5$ cells/well. After 24 hrs, the cells were transfected with appropriate plasmids (neo control, RUNX2, or RUNX2Δ8, p21-promoter-luciferase, Alk5TD, Smad3) and using the TransIT-LT1 reagent (Mirus Corporation, Madison, Wis.) as suggested by the manufacturer. The TK-*Renilla* vector was used to normalize luciferase units in each transfection. Cells were lysed 48 hrs after transfection with passive lysis buffer supplied in the Dual Luciferase Kit. The lysates were then analyzed following the Dual Luciferase standard protocol and using the Turner Design Model TD-20/20 Luminometer.

Statistical Analysis

Data was expressed as mean±S.D. Statistical differences for cell growth, DNA synthesis, apoptosis, and luciferase measurements were analyzed with Student's t test.

Example 6

RUNX2 association with YAP and p21CIP1-promoter repression. DNA-binding transcription factors regulate gene expression by recruiting corepressors or coactivators to target promoters. Yeast two-hybrid screening has shown that the WW domain of the coactivator YAP binds to the PPxY motif (PPPYP) (SEQ ID NO: 47) of RUNX1. RUNX1 is an activator of the osteocalcin promoter, but the addition of a YAP dominant negative construct strongly inhibited osteocalcin promoter activity suggesting that YAP is a strong transcriptional coactivator of RUNX1. Since RUNX2 contains a PPxY motif that is identical to RUNX1, it was postulated that RUNX2 also binds YAP. To show that RUNX2 and YAP interact, Flag.RUNX2 and HA.YAP were expressed in HEK293 cells. Lysates were separated into cytoplasmic (C) and nuclear (N) fractions to verify the cellular location of each protein. Ectopic RUNX2 was localized to the nucleus, while YAP was observed in both cytoplasmic and nuclear fractions. Immunoprecipitation assays were performed on nuclear lysates with either the Flag.Tag antibody or the HA.Tag antibody and the proteins were immunoblotted. The immunoprecipitations with the Flag.Tag antibody identified Flag.RUNX2 and HA.YAP in the complex, while the complementary immunoprecipitations with the HA.Tag antibody identified HA.YAP and RUNX2 in the complex. The immunodepleted lysates were analyzed for possible unbound Flag.RUNX2 or HA.YAP by Western. Neither protein could be detected in the immunodepleted nuclear lysates. The p21CIP1 promoter was recently identified as a target of RUNX1 repression. Ectopic expression of RUNX2 was also shown to repress p21CIP1 promoter activity in nontransformed NIH3T3 cells. Since YAP may associate with RUNX2, we wanted to assess whether YAP could regulate repression of the p21 CIP1 promoter by RUNX2. Consistent with published results, Flag.RUNX2 was able to repress the p21 CIP1 promoter-luciferase construct in NIH3T3 cells. At a constant input (0.25 ug) of NEO control or Flag.RUNX2 vector, increasing amounts of HA.YAP were added to each sample. HA.YAP in the presence of NEO control had no significant effect on p21 CIP1 promoter activity. As HA.YAP DNA concentration increased in the presence of NEO, there was a slight decrease in promoter activation. However, increasing concentrations of HA.YAP alleviated the RUNX2 repression of p21CIP1 promoter activity in a dose dependent manner, resulting in complete relief of p21 CIP1 promoter repression at 1.0 ug DNA. The distal p21 CIP1 promoter contains three RUNX binding sites (RBS) near the p53 interacting sites. Deletion of site A resulted in almost complete loss of RUNX1 repression of luciferase reporter activity. To determine whether RUNX2 also interacted with this binding site, a 20 nucleotide synthetic oligonucleotide was created containing the consensus RBS and the flanking sequences from the distal site A in the p21CIP1 promoter. Using DNA precipitation assays, RUNX2 was found to bind the wild type p21 CIP1 oligonucleotide but not the mutant oligonucleotide in which the RBS had been altered.

Relief of promoter repression by YAP requires direct RUNX2 binding. To elucidate whether a direct interaction between RUNX2 and YAP was responsible for the relief of RUNX2 repression of the p21CIP1 promoter, a RUNX2 mutant incapable of binding to YAP was engineered. Previous mutational analysis of the YAP binding site of RUNX1 showed that the first two Pro and second Tyr residues in the YAP binding domain (PPYP) (SEQ ID NO: 48) were necessary for transcriptional activation of a (tk) promoter containing a GAL4 binding site (24). Mutation of the first proline to an alanine completely abolished transcriptional activity. We reasoned that if YAP was directly interacting with RUNX2, a mutation of the first proline to an alanine in RUNX2 would reduce YAP binding and not affect the repression of the p21 CIP1 promoter. The mutant RUNX2, designated RUNX2 (P409A), was generated and its ability to interact with YAP was assessed. Co-immunopreciptiation assays with the Flag.RUNX2 or Flag.RUNX2(P409A) and HA.YAP showed that YAP could associate with wild-type RUNX2 but not with the mutant. We expected that the mutant RUNX2 would retain its ability to bind DNA since the P409A mutation was downstream of the Runt DNA binding domain (amino acids 50-177). To measure RUNX2(P409A) DNA binding, DNA precipitation assays using the wild type 20-mer, double-stranded oligonucleotide from the p21 CIP1 promoter site A were performed using nuclear lysates from HEK293 cells transfected with two mutant Flag.RUNX2(P409A) clones. Both RUNX2(P409A) mutant clones retained DNA-binding activity. After verification of DNA binding, the ability of the RUNX2 mutant protein to repress p21CIP1 promoter activity was determined. NIH3T3 cells were transfected with either RUNX2 or RUNX2(P409A) and luciferase activity was measured. Both mutant RUNX2(P409A) clones and the wild-type RUNX2 were strong repressors of the p21CIP1 promoter. However, HA.YAP was unable to relieve p21 CIP1 promoter repression by the mutant Flag.RUNX2(P409A). Since YAP relieved the RUNX2-mediated, but not RUNX2(P409A)-mediated repression of the p21 CIP1 promoter, these data suggest that direct YAP binding to RUNX2 is necessary to relieve RUNX2 repression of the p21 CIP1 promoter.

RUNX2 and YAP Synergistically Increase Oncogenic Transformation.

Overexpression of RUNX2 decreased p21CIP1 protein levels in endothelial cells which could influence cell survival. p21CIP1 interacts with specific cyclin dependent kinases to regulate G1/S cell cycle transition. Expression of a transcriptional repressor of p21CIP1, such as RUNX2, may alter cell cycle progression and lead to changes in cell survival, proliferation, and/or transformation. NIH3T3 cells were transfected with RUNX2 or RUNX2 and YAP with the appropriate control vectors.

Expression of RUNX2 or YAP was verified with antibodies specific for the flag or HAtag. Examination of post-confluent cultures of transfected NIH3T3 cells revealed that RUNX2 and RUNX2+YAP-transfected cells could grow on top of the confluent cell monolayers and form cell foci, indicative of transformation.

Transfected cells were suspended in soft agar to measure anchorage-independent growth, another indicator of transformation. After two weeks in soft agar, the RUNX2 transfected cells formed five times more colonies than the NEO (vector alone) controls. Moreover, the colonies formed by the combination of RUNX2 and YAP were two to five-fold larger than those of RUNX2 expressing cells. The number of colonies formed in the presence of RUNX2+YAP was greater than the number of colonies expected from expression of RUNX2 or YAP separately, indicating that overexpression of RUNX2 and YAP increase oncogenic transformation in a synergistic manner.

To determine whether the increased in cellular transformation was the result of a direct interaction between RUNX2 and YAP, cells transfected with the mutant RUNX2(P409A) and YAP were compared in the soft agar assay. Although RUNX2 (P409A) retained the ability to bind DNA and repress the p21CIP1 promoter, it was incapable of increasing cellular transformation in the absence of YAP and even inhibited growth in soft agar below the levels of the NEO control. The coexpression of YAP and RUNX2(P409A) had no effect on transformation. These results indicate a direct interaction between RUNX2 and YAP is necessary to induce loss of contact inhibition and growth in soft agar, established indicators of cellular transformation in NIH3T3 cells.

Experimental Procedures for Example 6.

Cell Culture and Reagents

NIH3T3 cells were cultured in DMEM (Biofluids) and 10% FBS (Biofluids) and used until passage 20. Stable NIH3T3 cell lines were selected in 1 mg/ml G418 (Invitrogen) and only used for 3 more passages after selection. Monoclonal anti-flag M2 antibody (Sigma) was used to detect or immunoprecipitate the flag-tagged RUNX2 or RUNX2 (P409A) mutant proteins. Monoclonal HA.11 antibody (Covance) was used to detect or immunoprecipitate the HA-tagged YAP.

Plasmids and Transfections pCMV-tag2a (NEO) was purchased from Stratagene. The fall length RUNX2 cDNA was inserted into the BamHI/XhoI sites of the pCMV-tag2a as previously described. The YAP expression vector and the empty vector control (X540-HA) were gifts from Dr. Iain Farrance (University of Maryland, Baltimore, Md.). The p21CIP1 promoter luciferase plasmid (WWP-LUC) was a gift from Dr. Bert Vogelstein (Johns Hopkins University, Baltimore, Md.). Using a site-directed mutanagesis kit (Invitrogen), a point mutation was introduced into the RUNX2 cDNA, which changed the proline at position 409 to an alanine, to create the RUNX2(P409A) mutant. The mutation was verified by sequencing.

Immunoprecipitation and Western Blot Analysis

Nuclear proteins were isolated using NucBuster (Novagen). Protein concentration was determined with the Bio-Rad Protein Assay. 1 mg of protein was diluted into 500 ul of immunoprecipitation buffer (20 mM Tris, pH 7.5, 2 mM $CaCl_2$, 1% Triton X-100, and 1× protease inhibitor cocktail (Roche)) and was precleared with 30 ul of protein G sepharose. For immunoprecipitations, 1 ug of antibody (M2 or HA) pre-bound to 30 ul of Protein G sepharose and was combined with Protein G pre-cleared nuclear extracts and incubated on an orbital shaker for at least 1 hr at 4° C. The mixture was centrifuged, and the pellet was washed 3 times with the IP buffer. All excess fluid was removed and 2.5 ul reducing agent (Invitrogen) and 22.5 ul of 4× Laemmli buffer was added to the pellet. Samples were boiled for 10 min and centrifuged. The supernatant was loaded on a 4-12% Nu-PAGE gel (Invitrogen), and electrotransferred to nitrocellulose membranes (Invitrogen). The blots were incubated with either anti-M2 antibody (1:1000) or anti-HA antibody (1:5000) followed by horseradish peroxidase-conjugated goat anti-mouse IgG (KPL, Gaithersburg, Md.). Specific proteins were detected by enhanced chemiluminescence (ECL, Amersham Pharmcia Biotech, Buckinghamshire, England).

DNA Precipitation Assays

Two single stranded, biotin labeled oligonucleotides corresponding to RUNX binding site A in the distal p21CIP1 promoter were hybridized to generate a double-stranded probe. For the wild-type probe, the specific oligos used were 5'GCTCAGTACCACAAAAATTC-biotin 3' (SEQ ID NO: 19) (sense) and 5' GAATTTTTGTGGTACTGAGC-biotin 3' (SEQ ID NO: 20) (antisense). For the mutant probe, the specific oligos used were 5'GCTCAGTCGAA-CAAAAATTC-biotin 3' (SEQ ID NO: 21) (sense) and 5' GAATTTTTGTTCGACTGAGC-biotin 3' (SEQ ID NO: 22). Equal concentrations of sense oligo and antisense oligo were added in annealing buffer for a final concentration of 3.33 uM of double-stranded oligo in 0.1M Tris, pH 7.6, 0.01M $MgCl_2$, 0.0034M DTT.

The mixture was heated to 95° C. for 10 minutes, allowed to cool slowly to 65° C., then allowed to cool to RT. Nuclear proteins were isolated using NucBuster (Novagen). 1 mg of protein was diluted into 500 ul of DNAP buffer (10 mM Hepes, pH 7.0, 100 mM KCl, 5 mM MgCl2, 10% glycerol, 1 mM DTT, 0.5% NP40, and 1× protease inhibitor cocktail), and samples were pre-cleared with 30 ul streptavidin-agarose beads (Pierce). The biotinylated, double stranded DNA probe (10 ul of a 3.33 uM stock) and 10 ug of poly dI/dC were added to the supernatant and incubated at 4° C. overnight. To the mixture, 30 ul of the streptavidin beads were added and the incubation continued at 4° C. for at least 1 hr. The supernatants were then removed and the beads were washed 3 times with 0.5 ml of the DNA precipitation buffer. Laemmli buffer plus reducing agent were added to the beads and the mixture was boiled for 10 minutes. After centrifugation at 14,000 rpm for 2 min, the supernatant was loaded on a 4-12% NuPage gel to resolve proteins bound to the DNA.

Luciferase Assays

Non-transformed, early passage NIH3T3 cells were plated in 6-well plates at a density of $10^5$ cells per well. Cells were allowed to recover for 24 hrs and then transfected with the indicated combination of plasmids. For all luciferase assays, the WWP-LUC plasmid was used at a concentration of 1 ug per well and the pTK-renilla was used at a concentration of 50 ng per well. Cells were incubated at 37° C. in a 5.0% CO2 incubator for 48 hrs. The cells were lysed with 1× passive lysis buffer (Promega). Lysates were analyzed using the Dual Luciferase Kit (Promega) and a Turner Design TD 20/20 luminometer.

Soft Agar Assays and Foci Formation

DMEM, 10% FBS, and agar (0.5%) mixture (2 ml) were added and allowed to cool and solidify at 25° C. for at least 30 min. Cells (20,000) in 0.5 ml DMEM, 10% FBS, and agar (0.33%) were carefully overlaid on the solidified agar base in each well. This mixture was allowed to solidify at 25° C. for 30 minutes. The plates were then incubated for 10 days in a 37° C., 5.0% CO2. Colony formation was compared and photos of representative regions from each well were taken using a Zeiss microscope, and video camera, and images were processed with Oncor Image software. Each photo contains multiple computer images fitted together to give a larger representative view of the colonies in each well. For measurement of foci formation, NIH3T3 cells and transfectants were cultured in 100 mm dishes and allowed to reach confluence. Cells growing above the fibroblast monolayer were photographed 25 days after culturing.

Example 7

To determine the ability of TGF-beta1 to inhibit HBME proliferation under conditions where RUNX2 expression is low, HBME were pretreated with siRNA vectors targeting RUNX2 for 24 hours prior to treatment with TGF-beta1 (2 ng/ml) under low serum conditions (1% FBS) for an additional 48 hours. Control treated cells (pSupNeo) exhibited a >10-fold increase in cell numbers under these conditions while TGF-beta1 treatment of Neo control cells resulted in only about a 3-fold increase. Expression of siRNA alone inhibited cell proliferation (4-fold increase in cell number) while treatment with TGF-beta1 after RUNX2 knockdown inhibited proliferation even further (2-fold increase in cell number). Since these high levels of TGF-beta1 (2 ng/ml) may overwhelm cell proliferation even in the presence of RUNX2, the experiment was repeated with a lower dose of TGF-beta1 (0.1 ng/ml). Under these conditions, TGF-beta1 inhibited proliferation more dramatically when cells were pretreated with siRNA targeting RUNX2 compared to control treated (pSupNeo) cells.

REFERENCES

Alexandrow, M. G., Kawabata, M., Aakre, M. & Moses, H. L. (1995). *Proc Natl Acad Sci USA,* 92, 3239-43.
Asahara, T., Bauters, C., Zheng, L. P., Takeshita, S., Bunting, S., Ferrara, N., Symes, J. F. & Isner, J. M. (1995). *Circulation,* 92, II365-71.
Baltzinger, M., Mager-Heckel, A. M. & Remy, P. (1999). *Dev Dyn,* 216, 420-33.
Beck, L., Jr. & D'Amore, P. A. (1997). *Faseb J,* 11, 365-73.
Blyth, K., Terry, A., Mackay, N., Vaillant, F., Bell, M., Cameron, E. R., Neil, J. C. & Stewart, M. (2001). *Oncogene,* 20, 295-302.
Bravo, J., Li, Z., Speck, N. A. & Warren, A. J. (2001). *Nat Struct Biol,* 8, 371-378.
Burchardt, M., Burchardt, T., Chen, M. W., Shabsigh, A., de la Taille, A., Buttyan, R. & Shabsigh, R. (1999). *Biol Reprod,* 60, 398-404.
Carmeliet, P. & Collen, D. (2000). *J Pathol,* 190, 387-405.
Claassen, G. F. & Hann, S. R. (2000). *Proc Natl Acad Sci USA,* 97, 9498-503.
Datto, M. B., Li, Y., Panus, J. F., Howe, D. J., Xiong, Y. & Wang, X. F. (1995). *Proc Natl Acad Sci USA,* 92, 5545-9.
Ducy, P., Zhang, R., Geoffroy, V., Ridall, A. L. & Karsenty, G. (1997). *Cell,* 89, 747-54. el-Deiry, W. S., Tokino, T., Velculescu, V. E., Levy, D. B., Parsons, R., Trent, J. M., Lin, D., Mercer, W. E., Kinzler, K. W. & Vogelstein, B. (1993). *Cell,* 75, 817-25.
Ferrara, N. (2000). *Recent Prog Holm Res,* 55, 15-35; discussion 35-6.
Flaumenhaft, R., Abe, M., Mignatti, P. & Rifkin, D. B. (1992). *J Cell Biol,* 118, 901-9.
Folkman, J. (1995). *Nat Med,* 1, 27-31.
Gartel, A. L. & Tyner, A. L. (1999). *Exp Cell Res,* 246, 280-9.
Geoffroy, V., Corral, D. A., Zhou, L., Lee, B. & Karsenty, G. (1998). *Mamm Genome,* 9, 54-7.
Gothie, E., Richard, D. E., Berra, E., Pages, G. & Pouyssegur, J. (2000). *J Biol Chem,* 275, 6922-7.
Hanahan, D. (1997). *Science,* 277, 48-50.
Hata-Sugi, N., Kawase-Kageyama, R. & Wakabayashi, T. (2002). *Biol Pharm Bull,* 25, 446-51.
Hiraoka, N., Allen, E., Apel, I. J., Gyetko, M. R. & Weiss, S. J. (1998). *Cell,* 95, 365-77.
Huang, Y. Q., Li, J. J. & Karpatkin, S. (2000). *Blood,* 95, 1993-9.
Ito, Y. (1999). *Genes Cells,* 4, 685-96.
Ito, Y. & Miyazono, K. (2003). *Curr Opin Genet Dev,* 13, 43-7.
Jakubowiak, A., Pouponnot, C., Berguido, F., Frank, R., Mao, S., Massague, J. & Nimer, S. D. (2000). *J Biol Chem,* 275, 40282-7.
Kalluri, R. & Sukhatme, V. P. (2000). *Curr Opin Nephrol Hypertens,* 9, 413-8.
Kerbel, R. S. (2000). *Carcinogenesis,* 21, 505-15.
Koff, A., Ohtsuki, M., Polyak, K., Roberts, J. M. & Massague, J. (1993). *Science,* 260, 536-9.
Komori, T., Yagi, H., Nomura, S., Yamaguchi, A., Sasaki, K., Deguchi, K., Shimizu, Y., Bronson, R. T., Gao, Y. H., Inada, M., Sato, M., Okamoto, R., Kitamura, Y., Yoshiki, S. & Kishimoto, T. (1997). *Cell,* 89, 755-64.
Kriventseva, E. V., Koch, I., Apweiler, R., Vingron, M., Bork, P., Gelfand, M. S. & Sunyaev, S. (2003). *Trends Genet,* 19, 124-8.
Laiho, M., DeCaprio, J. A., Ludlow, J. W., Livingston, D. M. & Massague, J. (1990). *Cell,* 62, 175-85.
Lehr, J. E. & Pienta, K. J. (1998). *J Natl Cancer Inst,* 90, 118-23.
Li, Q. L., Ito, K., Sakakura, C., Fukamachi, H., Inoue, K. I., Chi, X. Z., Lee, K. Y., Nomura, S., Lee, C. W., Han, S. B., Kim, H. M., Kim, W. J., Yamamoto, H., Yamashita, N., Yano, T., Ikeda, T., Itohara, S., Inazawa, J., Abe, T., Hagiwara, A., Yamagishi, H., Ooe, A., Kaneda, A., Sugimura, T., Ushijima, T., Bae, S. C. & Ito, Y. (2002). *Cell,* 109, 113-124.
Li, W. W. (2000). *Acad Radiol,* 7, 800-11.
Linggi, B., Muller-Tidow, C., van de Locht, L., Hu, M., Nip, J., Serve, H., Berdel, W. E., van der Reijden, B., Quelle, D. E., Rowley, J. D., Cleveland, J., Jansen, J. H., Pandolfi, P. P. & Hiebert, S. W. (2002). *Nat Med,* 8, 743-50.

Lund, A. H. & Van Lohuizen, M. (2002). *Cancer Cell,* 1, 213-215.
Lutterbach, B., Westendorf, J. J., Linggi, B., Isaac, S., Seto, E. & Hiebert, S. W. (2000). *J Biol Chem,* 275, 651-6.
Lyons, R. M. & Moses, H. L. (1990). *Eur J Bioche™,* 187, 467-73.
Maisonpierre, P. C., Suri, C., Jones, P. F., Bartunkova, S., Wiegand, S. J., Radziejewski, C., Compton, D., McClain, J., Aldrich, T. H., Papadopoulos, N., Daly, T. J., Davis, S., Sato, T. N. & Yancopoulos, G. D. (1997). *Science,* 277, 55-60.
Massague, J. & Wotton, D. (2000). *EMBO J,* 19, 1745-1754.
Nagata, K. (1996). *Trends Biochem Sci,* 21, 22-6.
Namba, K., Abe, M., Saito, S., Satake, M., Ohmoto, T., Watanabe, T. & Sato, Y. (2000). *Oncogene,* 19, 106-14.
Newton, L. K., Yung, W. K., Pettigrew, L. C. & Steck, P. A. (1990). *Exp Cell Res,* 190, 127-32.
Ngo, C. V., Gee, M., Akhtar, N., Yu, D., Volpert, 0., Auerbach, R. & Thomas-Tikhonenko, A. (2000). *Cell Growth Differ,* 11, 201-10.
Nicosia, R. F., Nicosia, S. V. & Smith, M. (1994). *Am J Pathol,* 145, 1023-9.
Nicosia, R. F. & Ottinetti, A. (1990). *Lab Invest,* 63, 115-22.
Nicosia, R. F. & Tuszynski, G. P. (1994). *J Cell Biol,* 124, 183-93.
Nor, J. E., Christensen, J., Mooney, D. J. & Polyerini, P. J. (1999). *Am JPathol,* 154, 375-84.
Ogawa, E., Inuzuka, M., Maruyama, M., Satake, M., Naito-Fujimoto, M., Ito, Y. & Shigesada, K. (1993). *Virology,* 194, 314-31.
Otto, F., Thornell, A. P., Crompton, T., Denzel, A., Gilmour, K. C., Rosewell, I. R., Stamp, G. W., Beddington, R. S., Mundlos, S., Olsen, B. R., Selby, P. B. & Owen, M. J. (1997). *Cell,* 89, 765-71.
Pepper, M. S., Belin, D., Montesano, R., Orci, L. & Vassalli, J. D. (1990). *J Cell Biol,* 111, 743-55.
Perry, C., Sklan, E. H., Birikh, K., Shapira, M., Trejo, L., Eldor, A. & Soreq, H. (2002). *Oncogene,* 21, 8428-41.
Poliman, M. J., Naumovski, L. & Gibbons, G. H. (1999). *J Cell Physiol,* 178, 359-70.
Rabbani, S. A. (1998). *In Vivo,* 12, 135-42.
Riccioni, T., Cirielli, C., Wang, X., Passaniti, A. & Capogrossi, M. C. (1998). *Gene Ther,* 5, 747-54.
Risau, W. & Flamme, I. (1995). *Annu Rev Cell Dev Biol,* 11, 73-91.
Roninson, I. B. (2002). *Cancer Lett,* 179, 1-14.
Sato, Y. (2000). *Pharmacol Ther,* 87, 51-60.
Selvamurugan, N., Pulumati, M. R., Tyson, D. R. & Partridge, N. C. (2000). *J Biol Chem,* 275, 5037-42.
Smith, C. W. J. & Valcarcel, J. (2000). *TIBS,* 25, 381-388.
Smith, J. S. (2002). *Trends in Cell Biol,* 12, 404-6.
Sorek, R. & Amitai, M. (2001). *Nature Biotechnol,* 19, 196.
Stewart, M., Terry, A., Hu, M., O'Hara, M., Blyth, K., Baxter, E., Cameron, E., Onions, D. E. & Neil, J. C. (1997). *Proc Natl Acad Sci USA,* 94, 8646-51.
Sun, L., Vitolo, M. & Passaniti, A. (2001). *Cancer Res,* 61, 4994-5001.
Taipale, J. & Keski-Oja, J. (1997). *Faseb J,* 11, 51-9.
Takakura, N., Watanabe, T., Suenobu, S., Yamada, Y., Noda, T., Ito, Y., Satake, M. & Suda, T. (2000). *Cell,* 102, 199-209.
Takeichi, H., Hosokawa, N., Hirayoshi, K. & Nagata, K. (1994). *Mol Cell Biol,* 14, 567-575.
Tischer, E., Mitchell, R., Hartman, T., Silva, M., Gospodarowicz, D., Fiddes, J. C. & Abraham, J. A. (1991). *J Biol Chem,* 266, 11947-54.
Vaillant, F., Blyth, K., Terry, A., Bell, M., Cameron, E. R., Neil, J. & Stewart, M. (1999). *Oncogene,* 18, 7124-34.
Wang, W. & Passaniti, A. (1999). *J Cell Biochem,* 73, 321-31.
Westendorf, J. J. & Hiebert, S. W. (1999). *J Cell Biochem,* 32/33, 51-8.
Westendorf, J. J., Zaidi, S. K., Cassino, J. E., Kahler, R., van Wijnen, A. J., Lian, J. B., Yoshida, M., Stein, G. S. & Li, X. (2002). *Mol Cell Biol,* 22, 7982-92.
Xiao, G., Jiang, D., Thomas, P., Benson, M. D., Guan, K., Karsenty, G. & Franceschi, R. T. (2000). *J Biol Chem,* 275, 4453-9.
Xiao, Z. S., Thomas, R., Hinson, T. K. & Quarles, L. D. (1998). *Gene,* 214, 187-97.
Yang, C., Chang, J., Gorospe, M. & Passaniti, A. (1996). *Cell Growth Differ,* 7, 161-71.
Zelzer, E., Glotzer, D. J., Hartmann, C., Thomas, D., Fukai, N., Soker, S. & Olsen, B. R. (2001). *Mech Dev,* 106, 97-106.
Zhang, Y. W., Bae, S. C., Takahashi, E. & Ito, Y. (1997). *Oncogene,* 15, 367-71.

TABLE I

| DESCRIPTION | AMINO ACID SEQUENCE |
|---|---|
| RUNX1 | |
| RUNX1 | GSIASPSVHPATPISPGRASGMTTLSAELSSRLSTAPDLTA (SEQ ID NO: 23) |
| RUNX2 | |
| RUNX2 | MRIPVDPSTSRRFSPPS (SEQ ID NO: 24) |
| Exon 8 | DDDTATSDFCLWPSTLSKKSQA (SEQ ID NO: 25) |
| Exon 8 | CLWPSTLSKKSQ (SEQ ID NO: 26) |
| Exon 8 | CLSPSTLSKKSQ (SEQ ID NO: 27) |
| RUNX2 | QMTSPSIHSTTPLSSTRGTGLPAITDVPRRIS (SEQ ID NO: 28) |
| RUNX2 | GASELGP (SEQ ID NO: 29) |
| RUNX2Δ8 | ISGA (SEQ ID NO: 4) |
| RUNX2Δ8 | QMTSPSIHSTTPLSSTRGTGLPAITDVPRRISGASELGP (SEQ ID NO: 30) |
| RUNX2Δ8 | CGGGPRRISGASE (SEQ ID NO: 31) |
| RUNX2Δ8 | TDVPRRISGASELGP (SEQ ID NO: 32) |
| RUNX3 | |
| RUNX3 | FDRSFPTLPTLTESRFPDPRMHYPGAMSAAFPYSATPSGT (SEQ ID NO: 33) |

What we claim:

1. A method for reducing angiogenesis in a subject in need thereof, comprising administering to the subject a therapeutically effective amount of an agent that reduces the expression or biological activity of RUNX2 polypeptide identified by amino acid SEQ ID NO: 35 or a biologically active fragment thereof, or by administering to the subject a therapeutically effective amount of a nucleic acid encoding RUNX2delta8 polypeptide identified by amino acid SEQ ID NO: 3 or a biologically active fragment thereof, or RUNX2delta8 polypeptide or a biologically active fragment thereof.

2. The method of claim 1, wherein the agent is selected from the group consisting of anti-sense RNA and siRNA that specifically binds to a gene identified by nucleotide SEQ ID NO: 34 that encodes RUNX2 polypeptide identified by amino acid SEQ ID NO: 35 or mRNA encoding the RUNX2 polypeptide thereby reducing its expression, or an antibody or antibody fragment that specifically binds to the RUNX2 polypeptide or a biologically active fragment thereof, thereby reducing RUNX2 polypeptide biological activity.

3. The method of claim 1, wherein the subject has a disorder or condition associated with neovascularization or excessive vascularization, or cancer or other cell proliferation disorder associated with excessive angiogenesis.

4. A method of reducing angiogenesis in a system comprising cells capable of forming blood vessels, comprising contacting the system with an effective amount of an agent that reduces the expression or biological activity of RUNX2 polypeptide identified by amino acid SEQ ID NO: 35 or with an effective amount of a nucleic acid encoding RUNX2delta8 polypeptide or a biologically active fragment thereof, or by administering to the subject a therapeutically effective amount of a nucleic acid encoding RUNX2delta8 polypeptide identified by amino acid SEQ ID NO: 3 or a biologically active fragment thereof, or RUNX2delta8 polypeptide or a biologically active fragment thereof.

5. The method of claim 4, wherein the agent is selected from the group consisting of anti-sense RNA and siRNA that specifically binds to a gene identified by nucleotide SEQ ID NO: 34 that encodes RUNX2 polypeptide identified by amino acid SEQ ID NO: 35 or mRNA encoding the RUNX2 polypeptide identified by amino acid SEQ ID NO: 35, or an antibody or antibody fragment that specifically binds to the RUNX2 polypeptide or a biologically active fragment thereof, thereby reducing RUNX2 biological activity.

* * * * *

SEQUENCE LISTING

<160> NUMBER OF SEQ ID NOS: 48

<210> SEQ ID NO 1
<211> LENGTH: 480
<212> TYPE: PRT
<213> ORGANISM: Homo sapiens

<400> SEQUENCE: 1

```
Met Ala Ser Asp Ser Ile Phe Glu Ser Phe Pro Ser Tyr Pro Gln Cys
 1               5                  10                  15

Phe Met Arg Glu Cys Ile Leu Gly Met Asn Pro Ser Arg Asp Val His
             20                  25                  30

Asp Ala Ser Thr Ser Arg Arg Phe Thr Pro Pro Ser Thr Ala Leu Ser
         35                  40                  45

Pro Gly Lys Met Ser Glu Ala Leu Pro Leu Gly Ala Pro Asp Ala Gly
     50                  55                  60

Ala Ala Leu Ala Gly Lys Leu Arg Ser Gly Asp Arg Ser Met Val Glu
 65                  70                  75                  80

Val Leu Ala Asp His Pro Gly Glu Leu Val Arg Thr Asp Ser Pro Asn
                 85                  90                  95

Phe Leu Cys Ser Val Leu Pro Thr His Trp Arg Cys Asn Lys Thr Leu
            100                 105                 110

Pro Ile Ala Phe Lys Val Val Ala Leu Gly Asp Val Pro Asp Gly Thr
        115                 120                 125

Leu Val Thr Val Met Ala Gly Asn Asp Glu Asn Tyr Ser Ala Glu Leu
    130                 135                 140

Arg Asn Ala Thr Ala Ala Met Lys Asn Gln Val Ala Arg Phe Asn Asp
145                 150                 155                 160

Leu Arg Phe Val Gly Arg Ser Gly Arg Gly Lys Ser Phe Thr Leu Thr
                165                 170                 175

Ile Thr Val Phe Thr Asn Pro Pro Gln Val Ala Thr Tyr His Arg Ala
            180                 185                 190

Ile Lys Ile Thr Val Asp Gly Pro Arg Glu Pro Arg Arg His Arg Gln
        195                 200                 205

Lys Leu Asp Asp Gln Thr Lys Pro Gly Ser Leu Ser Phe Ser Glu Arg
    210                 215                 220

Leu Ser Glu Leu Glu Gln Leu Arg Arg Thr Ala Met Arg Val Ser Pro
225                 230                 235                 240

His His Pro Ala Pro Thr Pro Asn Pro Arg Ala Ser Leu Asn His Ser
                245                 250                 255

Thr Ala Phe Asn Pro Gln Pro Gln Ser Gln Met Gln Asp Thr Arg Gln
            260                 265                 270

Ile Gln Pro Ser Pro Pro Trp Ser Tyr Asp Gln Ser Tyr Gln Tyr Leu
        275                 280                 285

Gly Ser Ile Ala Ser Pro Ser Val His Pro Ala Thr Pro Ile Ser Pro
    290                 295                 300

Gly Arg Ala Ser Gly Met Thr Thr Leu Ser Ala Glu Leu Ser Ser Arg
305                 310                 315                 320

Leu Ser Thr Ala Pro Asp Leu Thr Ala Phe Ser Asp Pro Arg Gln Phe
                325                 330                 335

Pro Ala Leu Pro Ser Ile Ser Asp Pro Arg Met His Tyr Pro Gly Ala
            340                 345                 350

Phe Thr Tyr Ser Pro Thr Pro Val Thr Ser Gly Ile Gly Ile Gly Met
        355                 360                 365
```

```
Ser Ala Met Gly Ser Ala Thr Arg Tyr His Thr Tyr Leu Pro Pro
    370                 375                 380

Tyr Pro Gly Ser Ser Gln Ala Gln Gly Gly Pro Phe Gln Ala Ser Ser
385                 390                 395                 400

Pro Ser Tyr His Leu Tyr Tyr Gly Ala Ser Ala Gly Ser Tyr Gln Phe
                405                 410                 415

Ser Met Val Gly Gly Glu Arg Ser Pro Pro Arg Ile Leu Pro Pro Cys
            420                 425                 430

Thr Asn Ala Ser Thr Gly Ser Ala Leu Leu Asn Pro Ser Leu Pro Asn
        435                 440                 445

Gln Ser Asp Val Val Glu Ala Glu Gly Ser His Ser Asn Ser Pro Thr
    450                 455                 460

Asn Met Ala Pro Ser Ala Arg Leu Glu Glu Ala Val Trp Arg Pro Tyr
465                 470                 475                 480

<210> SEQ ID NO 2
<211> LENGTH: 415
<212> TYPE: PRT
<213> ORGANISM: Homo sapiens

<400> SEQUENCE: 2

Met Arg Ile Pro Val Asp Pro Ser Thr Ser Arg Arg Phe Thr Pro Pro
  1               5                  10                  15

Ser Pro Ala Phe Pro Cys Gly Gly Gly Gly Lys Met Gly Glu Asn
                20                  25                  30

Ser Gly Ala Leu Ser Ala Gln Ala Ala Val Gly Pro Gly Gly Arg Ala
            35                  40                  45

Arg Pro Glu Val Arg Ser Met Val Asp Val Leu Ala Asp His Ala Gly
        50                  55                  60

Glu Leu Val Arg Thr Asp Ser Pro Asn Phe Leu Cys Ser Val Leu Pro
 65                  70                  75                  80

Ser His Trp Arg Cys Asn Lys Thr Leu Pro Val Ala Phe Lys Val Val
                    85                  90                  95

Ala Leu Gly Asp Val Pro Asp Gly Thr Val Val Thr Val Met Ala Gly
                100                 105                 110

Asn Asp Glu Asn Tyr Ser Ala Glu Leu Arg Asn Ala Ser Ala Val Met
            115                 120                 125

Lys Asn Gln Val Ala Arg Phe Asn Asp Leu Arg Phe Val Gly Arg Ser
130                 135                 140

Gly Arg Gly Lys Ser Phe Thr Leu Thr Ile Thr Val Phe Thr Asn Pro
145                 150                 155                 160

Thr Gln Val Ala Thr Tyr His Arg Ala Ile Lys Val Thr Val Asp Gly
                165                 170                 175

Pro Arg Glu Pro Arg Arg His Arg Gln Lys Leu Glu Asp Gln Thr Lys
            180                 185                 190

Pro Phe Pro Asp Arg Phe Gly Asp Leu Glu Arg Leu Arg Met Arg Val
        195                 200                 205

Thr Pro Ser Thr Pro Ser Pro Arg Gly Ser Leu Ser Thr Thr Ser His
    210                 215                 220

Phe Ser Ser Gln Pro Gln Thr Pro Ile Gln Gly Thr Ser Glu Leu Asn
225                 230                 235                 240

Pro Phe Ser Asp Pro Arg Gln Phe Asp Arg Ser Phe Pro Thr Leu Pro
                245                 250                 255

Thr Leu Thr Glu Ser Arg Phe Pro Asp Pro Arg Met His Tyr Pro Gly
            260                 265                 270
```

```
Ala Met Ser Ala Ala Phe Pro Tyr Ser Ala Thr Pro Ser Gly Thr Ser
        275                 280                 285

Ile Ser Ser Leu Ser Val Ala Gly Met Pro Ala Thr Ser Arg Phe His
        290                 295                 300

His Thr Tyr Leu Pro Pro Tyr Pro Gly Ala Pro Gln Asn Gln Ser
305                 310                 315                 320

Gly Pro Phe Gln Ala Asn Pro Ser Pro Tyr His Leu Tyr Tyr Gly Thr
                325                 330                 335

Ser Ser Gly Ser Tyr Gln Phe Ser Met Val Ala Gly Ser Ser Ser Gly
            340                 345                 350

Gly Asp Arg Ser Pro Thr Arg Met Leu Ala Ser Cys Thr Ser Ser Ala
        355                 360                 365

Ala Ser Val Ala Ala Gly Asn Leu Met Asn Pro Ser Leu Gly Gly Gln
        370                 375                 380

Ser Asp Gly Val Glu Ala Asp Gly Ser His Ser Asn Ser Pro Thr Ala
385                 390                 395                 400

Leu Ser Thr Pro Gly Arg Met Asp Glu Ala Val Trp Arg Pro Tyr
                405                 410                 415

<210> SEQ ID NO 3
<211> LENGTH: 485
<212> TYPE: PRT
<213> ORGANISM: Homo sapiens

<400> SEQUENCE: 3

Met Arg Ile Pro Val Asp Pro Ser Thr Ser Arg Phe Ser Pro Pro
  1               5                  10                  15

Ser Ser Ser Leu Gln Pro Gly Lys Met Ser Asp Val Ser Pro Val Val
                20                  25                  30

Ala Ala Gln Gln Gln Gln Gln Gln Gln Gln Gln Gln Gln Gln Gln
            35                  40                  45

Gln Gln Gln Gln Gln Gln Gln Gln Glu Ala Ala Ala Ala Ala
        50                  55                  60

Ala Ala Ala Ala Ala Ala Ala Ala Ala Val Pro Arg Leu Arg
 65                  70                  75                  80

Pro Pro His Asp Asn Arg Thr Met Val Glu Ile Ala Asp His Pro
                 85                  90                  95

Ala Glu Leu Val Arg Thr Asp Ser Pro Asn Phe Leu Cys Ser Val Leu
            100                 105                 110

Pro Ser His Trp Arg Cys Asn Lys Thr Leu Pro Val Ala Phe Lys Val
        115                 120                 125

Val Ala Leu Gly Glu Val Pro Asp Gly Thr Val Val Thr Val Met Ala
130                 135                 140

Gly Asn Asp Glu Asn Tyr Ser Ala Glu Leu Arg Asn Ala Ser Ala Val
145                 150                 155                 160

Met Lys Asn Gln Val Ala Arg Phe Asn Asp Leu Arg Phe Val Gly Arg
                165                 170                 175

Ser Gly Arg Gly Lys Ser Phe Thr Leu Thr Ile Thr Val Phe Thr Asn
            180                 185                 190

Pro Pro Gln Val Ala Thr Tyr His Arg Ala Ile Lys Val Thr Val Asp
        195                 200                 205

Gly Pro Arg Glu Pro Arg Arg His Arg Gln Lys Leu Asp Asp Ser Lys
210                 215                 220

Pro Ser Leu Phe Ser Asp Arg Leu Ser Asp Leu Gly Arg Ile Pro His
225                 230                 235                 240
```

```
Pro Ser Met Arg Val Gly Val Pro Pro Gln Asn Pro Arg Pro Ser Leu
            245                 250                 255

Asn Ser Ala Pro Ser Pro Phe Asn Pro Gln Gly Gln Ser Gln Ile Thr
        260                 265                 270

Asp Pro Arg Gln Ala Gln Ser Ser Pro Pro Trp Ser Tyr Asp Gln Ser
    275                 280                 285

Tyr Pro Ser Tyr Leu Ser Gln Met Thr Ser Pro Ser Ile His Ser Thr
290                 295                 300

Thr Pro Leu Ser Ser Thr Arg Gly Thr Gly Leu Pro Ala Ile Thr Asp
305                 310                 315                 320

Val Pro Arg Arg Ile Ser Gly Ala Ser Glu Leu Gly Pro Phe Ser Asp
                325                 330                 335

Pro Arg Gln Phe Pro Ser Ile Ser Ser Leu Thr Glu Ser Arg Phe Ser
            340                 345                 350

Asn Pro Arg Met His Tyr Pro Ala Thr Phe Thr Tyr Thr Pro Pro Val
        355                 360                 365

Thr Ser Gly Met Ser Leu Gly Met Ser Ala Thr Thr His Tyr His Thr
    370                 375                 380

Tyr Leu Pro Pro Pro Tyr Pro Gly Ser Ser Gln Ser Gln Ser Gly Pro
385                 390                 395                 400

Phe Gln Thr Ser Ser Thr Pro Tyr Leu Tyr Tyr Gly Thr Ser Ser Gly
                405                 410                 415

Ser Tyr Gln Phe Pro Met Val Pro Gly Gly Asp Arg Ser Pro Ser Arg
            420                 425                 430

Met Leu Pro Pro Cys Thr Thr Thr Ser Asn Gly Ser Thr Leu Leu Asn
        435                 440                 445

Pro Asn Leu Pro Asn Gln Asn Asp Gly Val Asp Ala Asp Gly Ser His
    450                 455                 460

Ser Ser Ser Pro Thr Val Leu Asn Ser Ser Gly Arg Met Asp Glu Ser
465                 470                 475                 480

Val Trp Arg Pro Tyr
                485

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ile Ser Gly Ala
  1

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcacagacag aagcttgat                                                    19

<210> SEQ ID NO 6
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 6
cccagttctg aagcacct                                                       18

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ccggactata cagaccatct                                                     20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agtgtgagac tctcgtgtag                                                     20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcattgggtg tttgatgagg                                                     20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gttctacctt cagcttctgg                                                     20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgcacccatg gcagaaggag g                                                   21

<210> SEQ ID NO 12
<211> LENGTH: 21
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 12
tcaccgcctc ggcttgtcac a                                               21

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
catcctgaag catacaggtc                                                 20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cagaaggaat ggtttgatgg                                                 20

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
agatctgatg cgtattcctg tagatccg                                        28

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ctctcgagtc aatatggtcg ccaaacag                                        28

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cagtatgaga gtaggtgtcc                                                 20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 18
aagggtccac tctggctttg                                                   20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gctcagtacc acaaaaattc                                                   20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20 gaattttttgt ggtactgagc                                                  20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gctcagtcga acaaaaattc                                                   20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gaatttttgt tcgactgagc                                                   20

<210> SEQ ID NO 23
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Ser Ile Ala Ser Pro Ser Val His Pro Ala Thr Pro Ile Ser Pro
 1               5                  10                  15

Gly Arg Ala Ser Gly Met Thr Thr Leu Ser Ala Glu Leu Ser Ser Arg
            20                  25                  30

Leu Ser Thr Ala Pro Asp Leu Thr Ala
        35                  40

<210> SEQ ID NO 24
<211> LENGTH: 17

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Met Arg Ile Pro Val Asp Pro Ser Thr Ser Arg Arg Phe Ser Pro Pro
 1               5                  10                  15

Ser

<210> SEQ ID NO 25
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asp Asp Asp Thr Ala Thr Ser Asp Phe Cys Leu Trp Pro Ser Thr Leu
 1               5                  10                  15

Ser Lys Lys Ser Gln Ala
            20

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Cys Leu Trp Pro Ser Thr Leu Ser Lys Lys Ser Gln
 1               5                  10

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Cys Leu Ser Pro Ser Thr Leu Ser Lys Lys Ser Gln
 1               5                  10

<210> SEQ ID NO 28
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gln Met Thr Ser Pro Ser Ile His Ser Thr Thr Pro Leu Ser Ser Thr
 1               5                  10                  15

Arg Gly Thr Gly Leu Pro Ala Ile Thr Asp Val Pro Arg Arg Ile Ser
            20                  25                  30

<210> SEQ ID NO 29
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 29

Gly Ala Ser Glu Leu Gly Pro
  1               5

<210> SEQ ID NO 30
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gln Met Thr Ser Pro Ser Ile His Ser Thr Thr Pro Leu Ser Ser Thr
  1               5                  10                  15

Arg Gly Thr Gly Leu Pro Ala Ile Thr Asp Val Pro Arg Arg Ile Ser
             20                  25                  30

Gly Ala Ser Glu Leu Gly Pro
         35

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Cys Gly Gly Gly Pro Arg Arg Ile Ser Gly Ala Ser Glu
  1               5                  10

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Thr Asp Val Pro Arg Arg Ile Ser Gly Ala Ser Glu Leu Gly Pro
  1               5                  10                  15

<210> SEQ ID NO 33
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Phe Asp Arg Ser Phe Pro Thr Leu Pro Thr Leu Thr Glu Ser Arg Phe
  1               5                  10                  15

Pro Asp Pro Arg Met His Tyr Pro Gly Ala Met Ser Ala Ala Phe Pro
             20                  25                  30

Tyr Ser Ala Thr Pro Ser Gly Thr
         35                  40

<210> SEQ ID NO 34
<211> LENGTH: 1524
```

```
<212> TYPE: DNA
<213> ORGANISM: Homo sapiens
<220> FEATURE:
<221> NAME/KEY: CDS
<222> LOCATION: (1)..(1521)

<400> SEQUENCE: 34 atg cgt att cct gta gat ccg agc acc agc cgg cgc ttc agc ccc ccc      48
Met Arg Ile Pro Val Asp Pro Ser Thr Ser Arg Arg Phe Ser Pro Pro
 1               5                  10                  15 tcc agc agc ctg cag ccc ggc aaa atg agc gac gtg agc ccg gtg gtg      96
Ser Ser Ser Leu Gln Pro Gly Lys Met Ser Asp Val Ser Pro Val Val
             20                  25                  30 gct gcg caa cag cag cag caa cag cag cag caa cag cag cag cag          144
Ala Ala Gln Gln Gln Gln Gln Gln Gln Gln Gln Gln Gln Gln Gln
         35                  40                  45 cag cag caa cag cag cag cag cag gag gcg gcg gcg gcg gct gcg          192
Gln Gln Gln Gln Gln Gln Gln Gln Glu Ala Ala Ala Ala Ala Ala
 50                  55                  60 gcg gca gcg gcg gct gcg gcg gcg gca gct gca gtg ccc cgg ttg cgg      240
Ala Ala Ala Ala Ala Ala Ala Ala Ala Ala Ala Val Pro Arg Leu Arg
 65                  70                  75                  80 ccg ccc cac gac aac cgc acc atg gtg gag atc atc gcc gac cac ccg      288
Pro Pro His Asp Asn Arg Thr Met Val Glu Ile Ile Ala Asp His Pro
                 85                  90                  95 gcc gaa ctc gtc cga acc gac agc ccc aac ttc ctg tgc tcg gtg ctg      336
Ala Glu Leu Val Arg Thr Asp Ser Pro Asn Phe Leu Cys Ser Val Leu
            100                 105                 110 ccc tcg cac tgg cgc tgc aac aag acc ctg ccc gtg gcc ttc aag gtg      384
Pro Ser His Trp Arg Cys Asn Lys Thr Leu Pro Val Ala Phe Lys Val
        115                 120                 125 gta gcc ctc gga gag gta cca gat ggg act gtg gtt act gtc atg gcg      432
Val Ala Leu Gly Glu Val Pro Asp Gly Thr Val Val Thr Val Met Ala
    130                 135                 140 ggt aac gat gaa aat tat tct gct gag ctc cgg aat gcc tct gct gtt      480
Gly Asn Asp Glu Asn Tyr Ser Ala Glu Leu Arg Asn Ala Ser Ala Val
145                 150                 155                 160 atg aaa aac caa gta gca agg ttc aac gat ctg aga ttt gtg ggc cgg      528
Met Lys Asn Gln Val Ala Arg Phe Asn Asp Leu Arg Phe Val Gly Arg
                165                 170                 175 agt gga cga ggc aag agt ttc acc ttg acc ata acc gtc ttc aca aat      576
Ser Gly Arg Gly Lys Ser Phe Thr Leu Thr Ile Thr Val Phe Thr Asn
            180                 185                 190 cct ccc caa gta gct acc tat cac aga gca att aaa gtt aca gta gat      624
Pro Pro Gln Val Ala Thr Tyr His Arg Ala Ile Lys Val Thr Val Asp
        195                 200                 205 gga cct cgg gaa ccc aga agg cac aga cag aag ctt gat gac tct aaa      672
Gly Pro Arg Glu Pro Arg Arg His Arg Gln Lys Leu Asp Asp Ser Lys
    210                 215                 220 cct agt ttg ttc tct gac cgc ctc agt gat tta ggg cgc att cct cat      720
Pro Ser Leu Phe Ser Asp Arg Leu Ser Asp Leu Gly Arg Ile Pro His
225                 230                 235                 240 ccc agt atg aga gta ggt gtc ccg cct cag aac cca cgg ccc tcc ctg      768
Pro Ser Met Arg Val Gly Val Pro Pro Gln Asn Pro Arg Pro Ser Leu
                245                 250                 255 aac tct gca cca agt cct ttt aat cca caa gga cag agt cag att aca      816
Asn Ser Ala Pro Ser Pro Phe Asn Pro Gln Gly Gln Ser Gln Ile Thr
            260                 265                 270 gac ccc agg cag gca cag tct tcc ccg ccg tgg tcc tat gac cag tct      864
Asp Pro Arg Gln Ala Gln Ser Ser Pro Pro Trp Ser Tyr Asp Gln Ser
        275                 280                 285
```

| | | | | | | | | | | | | | | | | |
|---|---|---|---|---|---|---|---|---|---|---|---|---|---|---|---|---|
| tac | ccc | tcc | tac | ctg | agc | cag | atg | acg | tcc | ccg | tcc | atc | cac | tct | acc | 912 |
| Tyr | Pro | Ser | Tyr | Leu | Ser | Gln | Met | Thr | Ser | Pro | Ser | Ile | His | Ser | Thr | |
| | 290 | | | | 295 | | | | 300 | | | | | | | |
| acc | ccg | ctg | tct | tcc | aca | cgg | ggc | act | ggg | ctt | cct | gcc | atc | acc | gat | 960 |
| Thr | Pro | Leu | Ser | Ser | Thr | Arg | Gly | Thr | Gly | Leu | Pro | Ala | Ile | Thr | Asp | |
| 305 | | | | | 310 | | | | | 315 | | | | | 320 | |
| gtg | cct | agg | cgc | att | tca | gat | gat | gac | act | gcc | acc | tct | gac | ttc | tgc | 1008 |
| Val | Pro | Arg | Arg | Ile | Ser | Asp | Asp | Asp | Thr | Ala | Thr | Ser | Asp | Phe | Cys | |
| | | | | 325 | | | | | 330 | | | | | 335 | | |
| ctc | tgg | cct | tcc | act | ctc | agt | aag | aag | agc | cag | gca | ggt | gct | tca | gaa | 1056 |
| Leu | Trp | Pro | Ser | Thr | Leu | Ser | Lys | Lys | Ser | Gln | Ala | Gly | Ala | Ser | Glu | |
| | | | 340 | | | | | 345 | | | | | 350 | | | |
| ctg | ggc | cct | ttt | tca | gac | ccc | agg | cag | ttc | cca | agc | att | tca | tcc | ctc | 1104 |
| Leu | Gly | Pro | Phe | Ser | Asp | Pro | Arg | Gln | Phe | Pro | Ser | Ile | Ser | Ser | Leu | |
| | | 355 | | | | | 360 | | | | | 365 | | | | |
| act | gag | agc | cgc | ttc | tcc | aac | cca | cga | atg | cac | tat | cca | gcc | acc | ttt | 1152 |
| Thr | Glu | Ser | Arg | Phe | Ser | Asn | Pro | Arg | Met | His | Tyr | Pro | Ala | Thr | Phe | |
| | 370 | | | | | 375 | | | | | 380 | | | | | |
| act | tac | acc | ccg | cca | gtc | acc | tca | ggc | atg | tcc | ctc | ggt | atg | tcc | gcc | 1200 |
| Thr | Tyr | Thr | Pro | Pro | Val | Thr | Ser | Gly | Met | Ser | Leu | Gly | Met | Ser | Ala | |
| 385 | | | | | 390 | | | | | 395 | | | | | 400 | |
| acc | act | cac | tac | cac | acc | tac | ctg | cca | cca | ccc | tac | ccc | ggc | tct | tcc | 1248 |
| Thr | Thr | His | Tyr | His | Thr | Tyr | Leu | Pro | Pro | Pro | Tyr | Pro | Gly | Ser | Ser | |
| | | | | 405 | | | | | 410 | | | | | 415 | | |
| caa | agc | cag | agt | gga | ccc | ttc | cag | acc | agc | agc | act | cca | tat | ctc | tac | 1296 |
| Gln | Ser | Gln | Ser | Gly | Pro | Phe | Gln | Thr | Ser | Ser | Thr | Pro | Tyr | Leu | Tyr | |
| | | | 420 | | | | | 425 | | | | | 430 | | | |
| tat | ggc | act | tcg | tca | gga | tcc | tat | cag | ttt | ccc | atg | gtg | ccg | ggg | gga | 1344 |
| Tyr | Gly | Thr | Ser | Ser | Gly | Ser | Tyr | Gln | Phe | Pro | Met | Val | Pro | Gly | Gly | |
| | | 435 | | | | | 440 | | | | | 445 | | | | |
| gac | cgg | tct | cct | tcc | aga | atg | ctt | ccg | cca | tgc | acc | acc | acc | tcg | aat | 1392 |
| Asp | Arg | Ser | Pro | Ser | Arg | Met | Leu | Pro | Pro | Cys | Thr | Thr | Thr | Ser | Asn | |
| | 450 | | | | | 455 | | | | | 460 | | | | | |
| ggc | agc | acg | cta | tta | aat | cca | aat | ttg | cct | aac | cag | aat | gat | ggt | gtt | 1440 |
| Gly | Ser | Thr | Leu | Leu | Asn | Pro | Asn | Leu | Pro | Asn | Gln | Asn | Asp | Gly | Val | |
| 465 | | | | | 470 | | | | | 475 | | | | | 480 | |
| gac | gct | gat | gga | agc | cac | agc | agt | tcc | cca | act | gtt | ttg | aat | tct | agt | 1488 |
| Asp | Ala | Asp | Gly | Ser | His | Ser | Ser | Ser | Pro | Thr | Val | Leu | Asn | Ser | Ser | |
| | | | | 485 | | | | | 490 | | | | | 495 | | |
| ggc | aga | atg | gat | gaa | tct | gtt | tgg | cga | cca | tat | tga | | | | | 1524 |
| Gly | Arg | Met | Asp | Glu | Ser | Val | Trp | Arg | Pro | Tyr | | | | | | |
| | | | 500 | | | | | 505 | | | | | | | | |

<210> SEQ ID NO 35
<211> LENGTH: 507
<212> TYPE: PRT
<213> ORGANISM: Homo sapiens

<400> SEQUENCE: 35

Met Arg Ile Pro Val Asp Pro Ser Thr Ser Arg Arg Phe Ser Pro Pro
1               5                   10                  15

Ser Ser Ser Leu Gln Pro Gly Lys Met Ser Asp Val Ser Pro Val Val
            20                  25                  30

Ala Ala Gln Gln Gln Gln Gln Gln Gln Gln Gln Gln Gln Gln Gln Gln
        35                  40                  45

Gln Gln Gln Gln Gln Gln Gln Gln Glu Ala Ala Ala Ala Ala
    50                  55                  60

Ala Ala Ala Ala Ala Ala Ala Ala Ala Ala Val Pro Arg Leu Arg
65                  70                  75                  80

Pro Pro His Asp Asn Arg Thr Met Val Glu Ile Ile Ala Asp His Pro

-continued

```
                85                  90                  95
Ala Glu Leu Val Arg Thr Asp Ser Pro Asn Phe Leu Cys Ser Val Leu
                100                 105                 110
Pro Ser His Trp Arg Cys Asn Lys Thr Leu Pro Val Ala Phe Lys Val
                115                 120                 125
Val Ala Leu Gly Glu Val Pro Asp Gly Thr Val Val Thr Val Met Ala
                130                 135                 140
Gly Asn Asp Glu Asn Tyr Ser Ala Glu Leu Arg Asn Ala Ser Ala Val
145                 150                 155                 160
Met Lys Asn Gln Val Ala Arg Phe Asn Asp Leu Arg Phe Val Gly Arg
                165                 170                 175
Ser Gly Arg Gly Lys Ser Phe Thr Leu Thr Ile Thr Val Phe Thr Asn
                180                 185                 190
Pro Pro Gln Val Ala Thr Tyr His Arg Ala Ile Lys Val Thr Val Asp
                195                 200                 205
Gly Pro Arg Glu Pro Arg Arg His Arg Gln Lys Leu Asp Asp Ser Lys
                210                 215                 220
Pro Ser Leu Phe Ser Asp Arg Leu Ser Asp Leu Gly Arg Ile Pro His
225                 230                 235                 240
Pro Ser Met Arg Val Gly Val Pro Gln Asn Pro Arg Pro Ser Leu
                245                 250                 255
Asn Ser Ala Pro Ser Pro Phe Asn Pro Gln Gly Gln Ser Gln Ile Thr
                260                 265                 270
Asp Pro Arg Gln Ala Gln Ser Ser Pro Pro Trp Ser Tyr Asp Gln Ser
                275                 280                 285
Tyr Pro Ser Tyr Leu Ser Gln Met Thr Ser Pro Ser Ile His Ser Thr
                290                 295                 300
Thr Pro Leu Ser Ser Thr Arg Gly Thr Gly Leu Pro Ala Ile Thr Asp
305                 310                 315                 320
Val Pro Arg Arg Ile Ser Asp Asp Thr Ala Thr Ser Asp Phe Cys
                325                 330                 335
Leu Trp Pro Ser Thr Leu Ser Lys Lys Ser Gln Ala Gly Ala Ser Glu
                340                 345                 350
Leu Gly Pro Phe Ser Asp Pro Arg Gln Phe Pro Ser Ile Ser Ser Leu
                355                 360                 365
Thr Glu Ser Arg Phe Ser Asn Pro Arg Met His Tyr Pro Ala Thr Phe
                370                 375                 380
Thr Tyr Thr Pro Pro Val Thr Ser Gly Met Ser Leu Gly Met Ser Ala
385                 390                 395                 400
Thr Thr His Tyr His Thr Tyr Leu Pro Pro Pro Tyr Pro Gly Ser Ser
                405                 410                 415
Gln Ser Gln Ser Gly Pro Phe Gln Thr Ser Ser Thr Pro Tyr Leu Tyr
                420                 425                 430
Tyr Gly Thr Ser Ser Gly Ser Tyr Gln Phe Pro Met Val Pro Gly Gly
                435                 440                 445
Asp Arg Ser Pro Ser Arg Met Leu Pro Pro Cys Thr Thr Thr Ser Asn
450                 455                 460
Gly Ser Thr Leu Leu Asn Pro Asn Leu Pro Asn Gln Asn Asp Gly Val
465                 470                 475                 480
Asp Ala Asp Gly Ser His Ser Ser Ser Pro Thr Val Leu Asn Ser Ser
                485                 490                 495
Gly Arg Met Asp Glu Ser Val Trp Arg Pro Tyr
                500                 505
```

```
<210> SEQ ID NO 36
<211> LENGTH: 1365
<212> TYPE: DNA
<213> ORGANISM: Homo sapiens
<220> FEATURE:
<221> NAME/KEY: CDS
<222> LOCATION: (1)..(1362)

<400> SEQUENCE: 36 atg gat ccc ggg cag cag ccg ccg cct caa ccg gcc ccc cag ggc caa      48
Met Asp Pro Gly Gln Gln Pro Pro Pro Gln Pro Ala Pro Gln Gly Gln
  1               5                  10                  15 ggg cag ccg cct tcg cag ccc ccg cag ggg cag ggc ccg ccg tcc gga      96
Gly Gln Pro Pro Ser Gln Pro Pro Gln Gly Gln Gly Pro Pro Ser Gly
             20                  25                  30 ccc ggg caa ccg gca ccc gcg gcg acc cag gcg gcg ccg cag gca ccc     144
Pro Gly Gln Pro Ala Pro Ala Ala Thr Gln Ala Ala Pro Gln Ala Pro
         35                  40                  45 ccc gcc ggg cat cag atc gtg cac gtc cgc ggg gac tcg gag acc gac     192
Pro Ala Gly His Gln Ile Val His Val Arg Gly Asp Ser Glu Thr Asp
     50                  55                  60 ctg gag gcg ctc ttc aac gcc gtc atg aac ccc aag acg gcc aac gtg     240
Leu Glu Ala Leu Phe Asn Ala Val Met Asn Pro Lys Thr Ala Asn Val
 65                  70                  75                  80 ccc cag acc gtg ccc atg agg ctc cgg aag ctg ccc gac tcc ttc ttc     288
Pro Gln Thr Val Pro Met Arg Leu Arg Lys Leu Pro Asp Ser Phe Phe
                 85                  90                  95 aag ccg ccg gag ccc aaa tcc cac tcc cga cag gcc agt act gat gca     336
Lys Pro Pro Glu Pro Lys Ser His Ser Arg Gln Ala Ser Thr Asp Ala
            100                 105                 110 ggc act gca gga gcc ctg act cca cag cat gtt cga gct cat tcc tct     384
Gly Thr Ala Gly Ala Leu Thr Pro Gln His Val Arg Ala His Ser Ser
        115                 120                 125 cca gct tct ctg cag ttg gga gct gtt tct cct ggg aca ctg acc ccc     432
Pro Ala Ser Leu Gln Leu Gly Ala Val Ser Pro Gly Thr Leu Thr Pro
    130                 135                 140 act gga gta gtc tct ggc cca gca gct aca ccc aca gct cag cat ctt     480
Thr Gly Val Val Ser Gly Pro Ala Ala Thr Pro Thr Ala Gln His Leu
145                 150                 155                 160 cga cag tct tct ttt gag ata cct gat gat gta cct ctg cca gca ggt     528
Arg Gln Ser Ser Phe Glu Ile Pro Asp Asp Val Pro Leu Pro Ala Gly
                165                 170                 175 tgg gag atg gca aag aca tct tct ggt cag aga tac ttc tta aat cac     576
Trp Glu Met Ala Lys Thr Ser Ser Gly Gln Arg Tyr Phe Leu Asn His
            180                 185                 190 atc gat cag aca aca aca tgg cag gac ccc agg aag gcc atg ctg tcc     624
Ile Asp Gln Thr Thr Thr Trp Gln Asp Pro Arg Lys Ala Met Leu Ser
        195                 200                 205 cag atg aac gtc aca gcc ccc acc agt cca cca gtg cag cag aat atg     672
Gln Met Asn Val Thr Ala Pro Thr Ser Pro Pro Val Gln Gln Asn Met
    210                 215                 220 atg aac tcg gct tca gcc atg aac cag aga atc agt cag agt gct cca     720
Met Asn Ser Ala Ser Ala Met Asn Gln Arg Ile Ser Gln Ser Ala Pro
225                 230                 235                 240 gtg aaa cag cca cca ccc ctg gct ccc cag agc cca cag gga ggc gtc     768
Val Lys Gln Pro Pro Pro Leu Ala Pro Gln Ser Pro Gln Gly Gly Val
                245                 250                 255 atg ggt ggc agc aac tcc aac cag cag caa cag atg cga ctg cag caa     816
Met Gly Gly Ser Asn Ser Asn Gln Gln Gln Gln Met Arg Leu Gln Gln
            260                 265                 270 ctg cag atg gag aag gag agg ctg cgg ctg aaa cag caa gaa ctg ctt     864
```

-continued

| | | | | | | | | | | | | | | |
|---|---|---|---|---|---|---|---|---|---|---|---|---|---|---|
| Leu | Gln | Met | Glu | Lys | Glu | Arg | Leu | Arg | Leu | Lys | Gln | Gln | Glu | Leu | Leu |
| | | 275 | | | | 280 | | | | 285 | | | | | |

```
cgg cag gtg agg cca cag gag tta gcc ctg cgt agc cag tta cca aca    912
Arg Gln Val Arg Pro Gln Glu Leu Ala Leu Arg Ser Gln Leu Pro Thr
    290             295                 300 ctg gag cag gat ggt ggg act caa aat cca gtg tct tct ccc ggg atg    960
Leu Glu Gln Asp Gly Gly Thr Gln Asn Pro Val Ser Ser Pro Gly Met
305             310                 315                 320 tct cag gaa ttg aga aca atg acg acc aat agc tca gat cct ttc ctt   1008
Ser Gln Glu Leu Arg Thr Met Thr Thr Asn Ser Ser Asp Pro Phe Leu
            325                 330                 335 aac agt ggc acc tat cac tct cga gat gag agt aca gac agt gga cta   1056
Asn Ser Gly Thr Tyr His Ser Arg Asp Glu Ser Thr Asp Ser Gly Leu
                340                 345                 350 agc atg agc agc tac agt gtc cct cga acc cca gat gac ttc ctg aac   1104
Ser Met Ser Ser Tyr Ser Val Pro Arg Thr Pro Asp Asp Phe Leu Asn
                355                 360                 365 agt gtg gat gag atg gat aca ggt gat act atc aac caa agc acc ctg   1152
Ser Val Asp Glu Met Asp Thr Gly Asp Thr Ile Asn Gln Ser Thr Leu
            370                 375                 380 ccc tca cag cag aac cgt ttc cca gac tac ctt gaa gcc att cct ggg   1200
Pro Ser Gln Gln Asn Arg Phe Pro Asp Tyr Leu Glu Ala Ile Pro Gly
385                 390                 395                 400 aca aat gtg gac ctt gga aca ctg gaa gga gat gga atg aac ata gaa   1248
Thr Asn Val Asp Leu Gly Thr Leu Glu Gly Asp Gly Met Asn Ile Glu
                405                 410                 415 gga gag gag ctg atg cca agt ctg cag gaa gct ttg agt tct gac atc   1296
Gly Glu Glu Leu Met Pro Ser Leu Gln Glu Ala Leu Ser Ser Asp Ile
                420                 425                 430 ctt aat gac atg gag tct gtt ttg gct gcc acc aag cta gat aaa gaa   1344
Leu Asn Asp Met Glu Ser Val Leu Ala Ala Thr Lys Leu Asp Lys Glu
            435                 440                 445 agc ttt ctt aca tgg tta tag                                       1365
Ser Phe Leu Thr Trp Leu
    450

<210> SEQ ID NO 37
<211> LENGTH: 454
<212> TYPE: PRT
<213> ORGANISM: Homo sapiens

<400> SEQUENCE: 37

Met Asp Pro Gly Gln Gln Pro Pro Gln Pro Ala Pro Gln Gly Gln
1               5                   10                  15

Gly Gln Pro Pro Ser Gln Pro Pro Gln Gly Gln Gly Pro Pro Ser Gly
                20                  25                  30

Pro Gly Gln Pro Ala Pro Ala Ala Thr Gln Ala Ala Pro Gln Ala Pro
            35                  40                  45

Pro Ala Gly His Gln Ile Val His Val Arg Gly Asp Ser Glu Thr Asp
    50                  55                  60

Leu Glu Ala Leu Phe Asn Ala Val Met Asn Pro Lys Thr Ala Asn Val
65                  70                  75                  80

Pro Gln Thr Val Pro Met Arg Leu Arg Lys Leu Pro Asp Ser Phe Phe
                85                  90                  95

Lys Pro Pro Glu Pro Lys Ser His Ser Arg Gln Ala Ser Thr Asp Ala
            100                 105                 110

Gly Thr Ala Gly Ala Leu Thr Pro Gln His Val Arg Ala His Ser Ser
    115                 120                 125

Pro Ala Ser Leu Gln Leu Gly Ala Val Ser Pro Gly Thr Leu Thr Pro
```

```
      130                 135                 140
Thr Gly Val Val Ser Gly Pro Ala Ala Thr Pro Thr Ala Gln His Leu
145                 150                 155                 160

Arg Gln Ser Ser Phe Glu Ile Pro Asp Asp Val Pro Leu Pro Ala Gly
                165                 170                 175

Trp Glu Met Ala Lys Thr Ser Ser Gly Gln Arg Tyr Phe Leu Asn His
            180                 185                 190

Ile Asp Gln Thr Thr Thr Trp Gln Asp Pro Arg Lys Ala Met Leu Ser
        195                 200                 205

Gln Met Asn Val Thr Ala Pro Thr Ser Pro Pro Val Gln Gln Asn Met
    210                 215                 220

Met Asn Ser Ala Ser Ala Met Asn Gln Arg Ile Ser Gln Ser Ala Pro
225                 230                 235                 240

Val Lys Gln Pro Pro Pro Leu Ala Pro Gln Ser Pro Gln Gly Gly Val
                245                 250                 255

Met Gly Gly Ser Asn Ser Asn Gln Gln Gln Gln Met Arg Leu Gln Gln
            260                 265                 270

Leu Gln Met Glu Lys Glu Arg Leu Arg Leu Lys Gln Gln Glu Leu Leu
        275                 280                 285

Arg Gln Val Arg Pro Gln Glu Leu Ala Leu Arg Ser Gln Leu Pro Thr
    290                 295                 300

Leu Glu Gln Asp Gly Gly Thr Gln Asn Pro Val Ser Ser Pro Gly Met
305                 310                 315                 320

Ser Gln Glu Leu Arg Thr Met Thr Thr Asn Ser Ser Asp Pro Phe Leu
                325                 330                 335

Asn Ser Gly Thr Tyr His Ser Arg Asp Glu Ser Thr Asp Ser Gly Leu
            340                 345                 350

Ser Met Ser Ser Tyr Ser Val Pro Arg Thr Pro Asp Asp Phe Leu Asn
        355                 360                 365

Ser Val Asp Glu Met Asp Thr Gly Asp Thr Ile Asn Gln Ser Thr Leu
    370                 375                 380

Pro Ser Gln Gln Asn Arg Phe Pro Asp Tyr Leu Glu Ala Ile Pro Gly
385                 390                 395                 400

Thr Asn Val Asp Leu Gly Thr Leu Glu Gly Asp Gly Met Asn Ile Glu
                405                 410                 415

Gly Glu Glu Leu Met Pro Ser Leu Gln Ala Leu Ser Ser Asp Ile
            420                 425                 430

Leu Asn Asp Met Glu Ser Val Leu Ala Ala Thr Lys Leu Asp Lys Glu
        435                 440                 445

Ser Phe Leu Thr Trp Leu
    450

<210> SEQ ID NO 38
<211> LENGTH: 351
<212> TYPE: DNA
<213> ORGANISM: Homo sapiens

<400> SEQUENCE: 38
gcacagacag aagcttgatg actctaaacc tagtttgttc tctgaccgcc tcagtgattt      60
agggcgcatt cctcatccca gtatgagagt aggtgtcccg cctcagaacc cacgccctc     120 cctgaactct gcaccaagtc cttttaatcc acaaggacag agtcagatta cagaccccag     180
acaggcacag tcttccccgc cgtggtccta tgaccagtct tacccgtcct acctgagcca     240
gatgacatcc ccgtccattc actccaccac cccgctgtct tccacgcggg gcacggggct     300
```
tcctgccatc accgacgtgc ccaggcgcat ttcaggtgct tcagaactgg g        351

<210> SEQ ID NO 39
<211> LENGTH: 116
<212> TYPE: PRT
<213> ORGANISM: Homo sapiens

<400> SEQUENCE: 39

His Arg Gln Lys Leu Asp Asp Ser Lys Pro Ser Leu Phe Ser Asp Arg
 1               5                  10                  15

Leu Ser Asp Leu Gly Arg Ile Pro His Pro Ser Met Arg Val Gly Val
            20                  25                  30

Pro Pro Gln Asn Pro Arg Pro Ser Leu Asn Ser Ala Pro Ser Pro Phe
        35                  40                  45

Asn Pro Gln Gly Gln Ser Gln Ile Thr Asp Pro Arg Gln Ala Gln Ser
    50                  55                  60

Ser Pro Pro Trp Ser Tyr Asp Gln Ser Tyr Pro Ser Tyr Leu Ser Gln
65                  70                  75                  80

Met Thr Ser Pro Ser Ile His Ser Thr Thr Pro Leu Ser Ser Thr Arg
                85                  90                  95

Gly Thr Gly Leu Pro Ala Ile Thr Asp Val Pro Arg Arg Ile Ser Gly
            100                 105                 110

Ala Ser Glu Leu
        115

<210> SEQ ID NO 40
<211> LENGTH: 417
<212> TYPE: DNA
<213> ORGANISM: Homo sapiens
<220> FEATURE:
<221> NAME/KEY: modified_base
<222> LOCATION: (297)
<223> OTHER INFORMATION: a, c, g, t, unknown or other

<400> SEQUENCE: 40
gcacagacag aagcttgatg actctaaacc tagtttgttc tctgaccgcc tcagtgattt     60
agggcgcatt cctcatccca gtatgagagt aggtgtcccg cctcagaacc cacggccctc   120
cctgaactct gcaccaagtc cttttaatcc acaaggacag agtcagatta cagaccccag   180
acaggcacag tcttccccgc cgtggtccta tgaccagtct tacccgtcct acctgagcca   240
gatgacatcc ccgtccattc actccaccac cccgctgtct tccacgcggg gcacggngct   300
tcctgccatc accgacgtgc ccaggcgcat ttcagatgat gacactgcca cctctgactt   360
ctgcctctgg ccttccactc tcagtaagaa gagccaggca ggtgcttcag aactggg      417

<210> SEQ ID NO 41
<211> LENGTH: 138
<212> TYPE: PRT
<213> ORGANISM: Homo sapiens

<400> SEQUENCE: 41

His Arg Gln Lys Leu Asp Asp Ser Lys Pro Ser Leu Phe Ser Asp Arg
 1               5                  10                  15

Leu Ser Asp Leu Gly Arg Ile Pro His Pro Ser Met Arg Val Gly Val
            20                  25                  30

Pro Pro Gln Asn Pro Arg Pro Ser Leu Asn Ser Ala Pro Ser Pro Phe
        35                  40                  45

Asn Pro Gln Gly Gln Ser Gln Ile Thr Asp Pro Arg Gln Ala Gln Ser
    50                  55                  60

-continued

Ser Pro Pro Trp Ser Tyr Asp Gln Ser Tyr Pro Ser Tyr Leu Ser Gln
65                  70                  75                  80

Met Thr Ser Pro Ser Ile His Ser Thr Thr Pro Leu Ser Ser Thr Arg
                85                  90                  95

Gly Thr Gly Leu Pro Ala Ile Thr Asp Val Pro Arg Arg Ile Ser Asp
            100                 105                 110

Asp Asp Thr Ala Thr Ser Asp Phe Cys Leu Trp Pro Ser Thr Leu Ser
        115                 120                 125

Lys Lys Ser Gln Ala Gly Ala Ser Glu Leu
    130                 135

<210> SEQ ID NO 42
<211> LENGTH: 22
<212> TYPE: PRT
<213> ORGANISM: Homo sapiens

<400> SEQUENCE: 42

Asp Asp Asp Thr Ala Thr Ser Asp Phe Cys Leu Trp Pro Ser Thr Leu
1               5                   10                  15

Ser Lys Lys Ser Gln Ala
            20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
cgtattaacc acaatactcg                                              20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
cgtacgagta ttgtggttaa                                              20

<210> SEQ ID NO 45
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Trp Arg Pro Tyr
1

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 46

-continued

```
His His His His His His
  1               5

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Pro Pro Pro Tyr Pro
  1               5

<210> SEQ ID NO 48
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Pro Pro Tyr Pro
  1
```